United States Patent [19]

Payne et al.

[11] Patent Number: 5,616,495

[45] Date of Patent: Apr. 1, 1997

[54] BACILLUS THURINGIENSIS GENE ENCODING HYMENOPTERAN-ACTIVE TOXINS

[75] Inventors: Jewel M. Payne, San Diego, Calif.; M. Keith Kennedy, Racine, Wis.; John B. Randall, Racine, Wis.; Henry Meier, Racine, Wis.; Heidi J. Uick, Racine, Wis.; Luis Foncerrada; Harry E. Schnepf, both of San Diego, Calif.; George E. Schwab, Encinitas, Calif.

[73] Assignee: Mycogen Corporation, San Diego, Calif.

[21] Appl. No.: 304,626

[22] Filed: Sep. 12, 1994

Related U.S. Application Data

[63] Continuation of Ser. No. 887,980, May 22, 1992, abandoned, which is a continuation-in-part of Ser. No. 703,977, May 22, 1991, Pat. No. 5,260,058, and a continuation-in-part of Ser. No. 797,645, Nov. 25, 1991, Pat. No. 5,268,297.

[51] Int. Cl.$^6$ .............................. C12N 1/21; C12N 15/32
[52] U.S. Cl. ...................................... 435/252.3; 536/23.71
[58] Field of Search ........................... 435/252.31, 252.5, 435/252.3; 536/23.71

[56] References Cited

U.S. PATENT DOCUMENTS

| | | | |
|---|---|---|---|
| 4,771,131 | 9/1988 | Hermstadt et al. | 536/23.71 |
| 4,966,765 | 10/1990 | Payne et al. | 424/93 |
| 5,196,342 | 3/1993 | Donovan | 435/320.1 |
| 5,208,017 | 5/1993 | Bradfisch et al. | 424/84 |
| 5,229,112 | 7/1993 | Obukowicz et al. | 424/93 A |

FOREIGN PATENT DOCUMENTS

| | | |
|---|---|---|
| 0202739 | 11/1986 | European Pat. Off. . |
| 0200344 | 12/1986 | European Pat. Off. . |
| 0303426 | 2/1989 | European Pat. Off. . |
| 0462721 | 12/1991 | European Pat. Off. . |
| 0471564 | 2/1992 | European Pat. Off. . |

OTHER PUBLICATIONS

Vankova, J.E. et al. (1975) "The control Monomorium pharaonis (Hymenoptera; Formicidae) with *Bacillus thuringiensis*" J. Invertebr. Pathol. 26(2):156–163. *abstract* Biological abstracts vol. 61, 1 Jan. 1976, Philadelphia, PA, US; abstract No. 1666.

Wisniewski, J. (1975) "Controlling Pharaoh ants in the zoo with *Bacillus thuringiensis*" Angew. Parasital. 16(1):43–49. *abstract* Biological abstracts vol. 60, 1975, Philadelphia, PA, US; abstract No. 36681.

Krieg, Von A., et al. (1983) "*Bacillus thuringiensis* var. tenebrionis: ein neuer, gegenuber Larven von Coleopteran wirksamer Pathotyp", Z. ang. Ent. 96:500–508.

Habermehl, G.G. *Venomous Animals and Their Toxins*, Springer–Verlag, NY: 1981: 81–83.

Holldobler, Bert and Edward O. Wilson. *The Ants*. Cambridge, MA: The Belknap Press of Harvard University Press. 609–617 (Chapter 18).

Couch, T.L. (1980) "Mosquito Pathogenicity of *Bacillus thuringiensis* var. *israelensis*," Develoments in Industrial Microbiology 22:61–76.

Beegle, C.C., (1978) "Use of entomogenous Bacteria in Agroecosystems," Developments in Industrial Microbiology 20:97–104.

Ebeling, Walter. (Professor of Entomology and Entomologist in the Experiment Station, University of California, Los Angeles, CA) *Urban Entomology*. 1978. 267–269.

Beatson, Susan H. (1972). "Pharaoh's Ants as Pathogen Vectors in Hospitals" The Lancet, Feb. 19, 1972.

Akre, R.D., L.D. Hansen and A.L. Antonelli, (1989). "Carpenter Ants: Their Biology and Control" USDA–ARS Ext. Bull. Washington State University. Coop. Ext. Serv. 1989 rev. No. EB 0818, 6 pp.

Wahl et al. (1987) in Methods in Enzymology (Academic Press, N.Y.), vol. 152, pp. 399–407.

Maniatis et al. (1982) Molecular Cloning: A Laboratory Manual (Cold Spring Harbor Laboratory, Cold Spring Harbor), pp. 324–325.

George et al. (1988) in Macromolecular Sequencing and Synthesis (Alan R. Liss, New York) pp. 127–149.

Vobrazkova et al. (1976) Angew–Parasitol., vol. 17, No. 2, pp. 94–99.

Prefontaine et al. (1987) Applied and Environmental Microbiology, vol. 53, No. 12, pp. 2808–2814.

Haider et al. (1987) Gene, vol. 52, pp. 285–290.

*Primary Examiner*—George C. Elliott
*Attorney, Agent, or Firm*—Saliwanchik, Lloyd & Saliwanchik

[57] ABSTRACT

Novel *Bacillus thuringiensis* isolates with hymenopteran activity are described. Also described are toxins having the advantageous hymenopteran activity.

This invention further concerns genes or gene fragments which have been cloned from the novel *Bacillus thuringiensis* isolates which have formicidal activity. These genes or gene fragments can be used to transform suitable hosts for controlling ants.

4 Claims, 5 Drawing Sheets

FIG. 2

1. *Bacillus thuringiensis* PS211B2
2. Protein Standard

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 4155 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: PS17
        ( C ) INDIVIDUAL ISOLATE: PS17a ( v i i ) IMMEDIATE SOURCE:
        ( B ) CLONE: E. coli NM522(pMYC1627) NRRL B-18651

( x i ) SEQUENCE DESCRIPTION: SEQ ID NO:1:

```
ATGGCAATTT   TAAATGAATT   ATATCCATCT   GTACCTTATA   ATGTATTGGC   GTATACGCCA       60
CCCTCTTTTT   TACCTGATGC   GGGTACACAA   GCTACACCTG   CTGACTTAAC   AGCTTATGAA      120
CAATTGTTGA   AAAATTTAGA   AAAAGGGATA   AATGCTGGAA   CTTATTCGAA   AGCAATAGCT      180
GATGTACTTA   AAGGTATTTT   TATAGATGAT   ACAATAAATT   ATCAAACATA   TGTAAATATT      240
GGTTTAAGTT   TAATTACATT   AGCTGTACCG   GAAATTGGTA   TTTTACACC    TTTCATCGGT      300
TTGTTTTTTG   CTGCATTGAA   TAAACATGAT   GCTCCACCTC   CTCCTAATGC   AAAAGATATA      360
TTTGAGGCTA   TGAAACCAGC   GATTCAAGAG   ATGATTGATA   GAACTTTAAC   TGCGGATGAG      420
CAAACATTTT   TAAATGGGGA   AATAAGTGGT   TTACAAAATT   TAGCAGCAAG   ATACCAGTCT      480
ACAATGGATG   ATATTCAAAG   CCATGGAGGA   TTTAATAAGG   TAGATTCTGG   ATTAATTAAA      540
AAGTTTACAG   ATGAGGTACT   ATCTTTAAAT   AGTTTTATA    CAGATCGTTT   ACCTGTATTT      600
ATTACAGATA   ATACAGCGGA   TCGAACTTTG   TTAGGTCTTC   CTTATTATGC   TATACTTGCG      660
```

```
AGCATGCATC TTATGTTATT AAGAGATATC ATTACTAAGG GTCCGACATG GGATTCTAAA    720
ATTAATTTCA CACCAGATGC AATTGATTCC TTTAAAACCG ATATTAAAAA TAATATAAAG    780
CTTTACTCTA AAACTATTTA TGACGTATTT CAGAAGGGAC TTGCTTCATA CGGAACGCCT    840
TCTGATTTAG AGTCCTTTGC AAAAAAACAA AAATATATTG AAATTATGAC AACACATTGT    900
TTAGATTTTG CAAGATTGTT TCCTACTTTT GATCCAGATC TTTATCCAAC AGGATCAGGT    960
GATATAAGTT TACAAAAAAC ACGTAGAATT CTTTCTCCTT TTATCCCTAT ACGTACTGCA   1020
GATGGGTTAA CATTAAATAA TACTTCAATT GATACTTCAA ATTGGCCTAA TTATGAAAAT   1080
GGGAATGGCG CGTTTCCAAA CCCAAAAGAA AGAATATTAA AACAATTCAA ACTGTATCCT   1140
AGTTGGAGAG CGGGACAGTA CGGTGGGCTT TTACAACCTT ATTTATGGGC AATAGAAGTC   1200
CAAGATTCTG TAGAGACTCG TTTGTATGGG CAGCTTCCAG CTGTAGATCC ACAGGCAGGG   1260
CCTAATTATG TTTCCATAGA TTCTTCTAAT CCAATCATAC AAATAAATAT GGATACTTGG   1320
AAAACACCAC CACAAGGTGC GAGTGGGTGG AATACAAATT TAATGAGAGG AAGTGTAAGC   1380
GGGTTAAGTT TTTTACAACG AGATGGTACG AGACTTAGTG CTGGTATGGG TGGTGGTTTT   1440
GCTGATACAA TATATAGTCT CCCTGCAACT CATTATCTTT CTTATCTCTA TGGAACTCCT   1500
TATCAAACTT CTGATAACTA TTCTGGTCAC GTTGGTGCAT GGTAGGTGT GAGTACGCCT    1560
CAAGAGGCTA CTCTTCCTAA TATTATAGGT CAACCAGATG AACAGGGAAA TGTATCTACA   1620
ATGGGATTTC CGTTTGAAAA AGCTTCTTAT GGAGGTACAG TTGTTAAAGA ATGGTAAAT    1680
GGTGCGAATG CGATGAAGCT TTCTCCTGGG CAATCTATAG GTATTCCTAT TACAAATGTA   1740
ACAAGTGGAG AATATCAAAT TCGTTGTCGT TATGCAAGTA ATGATAATAC TAACGTTTTC   1800
TTTAATGTAG ATACTGGTGG AGCAAATCCA ATTTTCCAAC AGATAAACTT TGCATCTACT   1860
GTAGATAATA ATACGGGAGT ACAAGGAGCA AATGGTGTCT ATGTAGTCAA ATCTATTGCT   1920
ACAACTGATA ATTCTTTTAC AGAAATTCCT GCGAAGACGA TTAATGTTCA TTTAACCAAC   1980
CAAGGTTCTT CTGATGTCTT TTTAGACCGT ATTGAATTTA TACCTTTTTC TCTACCTCTT   2040
ATATATCATG GAAGTTATAA TACTTCATCA GGTGCAGATG ATGTTTTATG GTCTTCTTCA   2100
AATATGAATT ACTACGATAT AATAGTAAAT GGTCAGGCCA ATAGTAGTAG TATCGCTAGT   2160
TCTATGCATT TGCTTAATAA AGGAAAAGTG ATAAAAACAA TTGATATTCC AGGGCATTCG   2220
GAAACCTTCT TTGCTACGTT CCCAGTTCCA GAAGGATTTA ATGAAGTTAG AATTCTTGCT   2280
GGCCTTCCAG AAGTTAGTGG AAATATTACC GTACAATCTA ATAATCCGCC TCAACCTAGT   2340
AATAATGGTG GTGGTGATGG TGGTGGTAAT GGTGGTGGTG ATGGTGGTCA ATACAATTTT   2400
TCTTTAAGCG GATCTGATCA TACGACTATT TATCATGGAA AACTTGAAAC TGGGATTCAT   2460
GTACAAGGTA ATTATACCTA TACAGGTACT CCCGTATTAA TACTGAATGC TTACAGAAAT   2520
AATACTGTAG TATCAAGCAT TCCAGTATAT TCTCCTTTTG ATATAACTAT ACAGACAGAA   2580
GCTGATAGCC TTGAGCTTGA ACTACAACCT AGATATGGTT TTGCCACAGT GAATGGTACT   2640
GCAACAGTAA AAAGTCCTAA TGTAAATTAC GATAGATCAT TTAAACTCCC AATAGACTTA   2700
CAAAATATCA CAACACAAGT AAATGCATTA TTCGCATCTG AACACAAAA TATGCTTGCT   2760
CATAATGTAA GTGATCATGA TATTGAAGAA GTTGTATTAA AAGTGGATGC CTTATCAGAT   2820
GAAGTATTTG GAGATGAGAA GAAGGCTTTA CGTAAATTGG TGAATCAAGC AAAACGTTTG   2880
AGTAGAGCAA GAAATCTTCT GATAGGTGGG AGTTTTGAAA ATTGGGATGC ATGGTATAAA   2940
GGAAGAAATG TAGTAACTGT ATCTGATCAT GAACTATTTA AGAGTGATCA TGTATTATTA   3000
CCACCACCAG GATTGTCTCC ATCTTATATT TTCCAAAAAG TGGAGGAATC TAAATTAAAA   3060
```

-continued

```
CCAAATACAC GTTATATTGT TTCTGGATTC ATCGCACATG GAAAAGACCT AGAAATTGTT  3120
GTTTCACGTT ATGGGCAAGA AGTGCAAAAG GTCGTGCAAG TTCCTTATGG AGAAGCATTC  3180
CCGTTAACAT CAAATGGACC AGTTTGTTGT CCCCCACGTT CTACAAGTAA TGGAACCTTA  3240
GGAGATCCAC ATTTCTTTAG TTACAGTATC GATGTAGGTG CACTAGATTT ACAAGCAAAC  3300
CCTGGTATTG AATTTGGTCT TCGTATTGTA AATCCAACTG GAATGGCACG CGTAAGCAAT  3360
TTGGAAATTC GTGAAGATCG TCCATTAGCA GCAAATGAAA TACGACAAGT ACAACGTGTC  3420
GCAAGAAATT GGAGAACCGA GTATGAGAAA GAACGTGCGG AAGTAACAAG TTTAATTCAA  3480
CCTGTTATCA ATCGAATCAA CGGATTGTAT GAAAATGGAA ATTGGAACGG TTCTATTCGT  3540
TCAGATATTT CGTATCAGAA TATAGACGCG ATTGTATTAC CAACGTTACC AAAGTTACGC  3600
CATTGGTTTA TGTCAGATAG ATTCAGTGAA CAAGGAGATA TAATGGCTAA ATTCCAAGGT  3660
GCATTAAATC GTGCGTATGC ACAACTGGAA CAAAGTACGC TTCTGCATAA TGGTCATTTT  3720
ACAAAAGATG CAGCTAATTG GACAATAGAA GGCGATGCAC ATCAGATAAC ACTAGAAGAT  3780
GGTAGACGTG TATTGCGACT TCCAGATTGG TCTTCGAGTG TATCTCAAAT GATTGAAATC  3840
GAGAATTTTA ATCCAGATAA AGAATACAAC TTAGTATTCC ATGGGCAAGG AGAAGGAACG  3900
GTTACGTTGG AGCATGGAGA AGAAACAAAA TATATAGAAA CGCATACACA TCATTTTGCG  3960
AATTTTACAA CTTCTCAACG TCAAGGACTC ACGTTTGAAT CAAATAAAGT GACAGTGACC  4020
ATTTCTTCAG AAGATGGAGA ATTCTTAGTG GATAATATTG CGCTTGTGGA AGCTCCTCTT  4080
CCTACAGATG ACCAAAATTC TGAGGGAAAT ACGGCTTCCA GTACGAATAG CGATACAAGT  4140
ATGAACAACA ATCAA                                                    4155
```

( 2 ) INFORMATION FOR SEQ ID NO:2:

( i ) SEQUENCE CHARACTERISTICS:
( A ) LENGTH: 1385 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( B ) STRAIN: PS17
( C ) INDIVIDUAL ISOLATE: PS17a ( v i i ) IMMEDIATE SOURCE:
( B ) CLONE: E. coli NM522(pMYC1627) NRRL B-18651

( x i ) SEQUENCE DESCRIPTION: SEQ ID NO:2:

```
Met Ala Ile Leu Asn Glu Leu Tyr Pro Ser Val Pro Tyr Asn Val Leu
1               5                   10                  15

Ala Tyr Thr Pro Pro Ser Phe Leu Pro Asp Ala Gly Thr Gln Ala Thr
            20                  25                  30

Pro Ala Asp Leu Thr Ala Tyr Glu Gln Leu Leu Lys Asn Leu Glu Lys
        35                  40                  45

Gly Ile Asn Ala Gly Thr Tyr Ser Lys Ala Ile Ala Asp Val Leu Lys
    50                  55                  60

Gly Ile Phe Ile Asp Asp Thr Ile Asn Tyr Gln Thr Tyr Val Asn Ile
65                  70                  75                  80

Gly Leu Ser Leu Ile Thr Leu Ala Val Pro Glu Ile Gly Ile Phe Thr
                85                  90                  95
```

```
Pro  Phe  Ile  Gly  Leu  Phe  Phe  Ala  Ala  Leu  Asn  Lys  His  Asp  Ala  Pro
          100                      105                      110
Pro  Pro  Pro  Asn  Ala  Lys  Asp  Ile  Phe  Glu  Ala  Met  Lys  Pro  Ala  Ile
     115                      120                      125
Gln  Glu  Met  Ile  Asp  Arg  Thr  Leu  Thr  Ala  Asp  Glu  Gln  Thr  Phe  Leu
130                      135                      140
Asn  Gly  Glu  Ile  Ser  Gly  Leu  Gln  Asn  Leu  Ala  Ala  Arg  Tyr  Gln  Ser
145                      150                      155                      160
Thr  Met  Asp  Asp  Ile  Gln  Ser  His  Gly  Gly  Phe  Asn  Lys  Val  Asp  Ser
               165                      170                      175
Gly  Leu  Ile  Lys  Lys  Phe  Thr  Asp  Glu  Val  Leu  Ser  Leu  Asn  Ser  Phe
          180                      185                      190
Tyr  Thr  Asp  Arg  Leu  Pro  Val  Phe  Ile  Thr  Asp  Asn  Thr  Ala  Asp  Arg
          195                      200                      205
Thr  Leu  Leu  Gly  Leu  Pro  Tyr  Tyr  Ala  Ile  Leu  Ala  Ser  Met  His  Leu
     210                      215                      220
Met  Leu  Leu  Arg  Asp  Ile  Ile  Thr  Lys  Gly  Pro  Thr  Trp  Asp  Ser  Lys
225                      230                      235                      240
Ile  Asn  Phe  Thr  Pro  Asp  Ala  Ile  Asp  Ser  Phe  Lys  Thr  Asp  Ile  Lys
               245                      250                      255
Asn  Asn  Ile  Lys  Leu  Tyr  Ser  Lys  Thr  Ile  Tyr  Asp  Val  Phe  Gln  Lys
          260                      265                      270
Gly  Leu  Ala  Ser  Tyr  Gly  Thr  Pro  Ser  Asp  Leu  Glu  Ser  Phe  Ala  Lys
          275                      280                      285
Lys  Gln  Lys  Tyr  Ile  Glu  Ile  Met  Thr  Thr  His  Cys  Leu  Asp  Phe  Ala
     290                      295                      300
Arg  Leu  Phe  Pro  Thr  Phe  Asp  Pro  Asp  Leu  Tyr  Pro  Thr  Gly  Ser  Gly
305                      310                      315                      320
Asp  Ile  Ser  Leu  Gln  Lys  Thr  Arg  Arg  Ile  Leu  Ser  Pro  Phe  Ile  Pro
               325                      330                      335
Ile  Arg  Thr  Ala  Asp  Gly  Leu  Thr  Leu  Asn  Asn  Thr  Ser  Ile  Asp  Thr
               340                      345                      350
Ser  Asn  Trp  Pro  Asn  Tyr  Glu  Asn  Gly  Asn  Gly  Ala  Phe  Pro  Asn  Pro
          355                      360                      365
Lys  Glu  Arg  Ile  Leu  Lys  Gln  Phe  Lys  Leu  Tyr  Pro  Ser  Trp  Arg  Ala
     370                      375                      380
Gly  Gln  Tyr  Gly  Gly  Leu  Leu  Gln  Pro  Tyr  Leu  Trp  Ala  Ile  Glu  Val
385                      390                      395                      400
Gln  Asp  Ser  Val  Glu  Thr  Arg  Leu  Tyr  Gly  Gln  Leu  Pro  Ala  Val  Asp
               405                      410                      415
Pro  Gln  Ala  Gly  Pro  Asn  Tyr  Val  Ser  Ile  Asp  Ser  Ser  Asn  Pro  Ile
               420                      425                      430
Ile  Gln  Ile  Asn  Met  Asp  Thr  Trp  Lys  Thr  Pro  Pro  Gln  Gly  Ala  Ser
          435                      440                      445
Gly  Trp  Asn  Thr  Asn  Leu  Met  Arg  Gly  Ser  Val  Ser  Gly  Leu  Ser  Phe
     450                      455                      460
Leu  Gln  Arg  Asp  Gly  Thr  Arg  Leu  Ser  Ala  Gly  Met  Gly  Gly  Gly  Phe
465                      470                      475                      480
Ala  Asp  Thr  Ile  Tyr  Ser  Leu  Pro  Ala  Thr  His  Tyr  Leu  Ser  Tyr  Leu
               485                      490                      495
Tyr  Gly  Thr  Pro  Tyr  Gln  Thr  Ser  Asp  Asn  Tyr  Ser  Gly  His  Val  Gly
               500                      505                      510
Ala  Leu  Val  Gly  Val  Ser  Thr  Pro  Gln  Glu  Ala  Thr  Leu  Pro  Asn  Ile
```

|     |     |     | 515 |     |     |     | 520 |     |     |     | 525 |     |     |     |
|-----|-----|-----|-----|-----|-----|-----|-----|-----|-----|-----|-----|-----|-----|-----|
| Ile | Gly | Gln | Pro | Asp | Glu | Gln | Gly | Asn | Val | Ser | Thr | Met | Gly | Phe | Pro |
|     | 530 |     |     |     | 535 |     |     |     |     | 540 |     |     |     |     |

| Phe | Glu | Lys | Ala | Ser | Tyr | Gly | Gly | Thr | Val | Val | Lys | Glu | Trp | Leu | Asn |
| 545 |     |     |     |     | 550 |     |     |     |     | 555 |     |     |     |     | 560 |

| Gly | Ala | Asn | Ala | Met | Lys | Leu | Ser | Pro | Gly | Gln | Ser | Ile | Gly | Ile | Pro |
|     |     |     |     | 565 |     |     |     |     | 570 |     |     |     |     | 575 |     |

| Ile | Thr | Asn | Val | Thr | Ser | Gly | Glu | Tyr | Gln | Ile | Arg | Cys | Arg | Tyr | Ala |
|     |     |     |     | 580 |     |     |     | 585 |     |     |     |     | 590 |     |     |

| Ser | Asn | Asp | Asn | Thr | Asn | Val | Phe | Phe | Asn | Val | Asp | Thr | Gly | Gly | Ala |
|     |     |     | 595 |     |     |     | 600 |     |     |     |     | 605 |     |     |     |

| Asn | Pro | Ile | Phe | Gln | Gln | Ile | Asn | Phe | Ala | Ser | Thr | Val | Asp | Asn | Asn |
|     | 610 |     |     |     |     | 615 |     |     |     |     | 620 |     |     |     |     |

| Thr | Gly | Val | Gln | Gly | Ala | Asn | Gly | Val | Tyr | Val | Val | Lys | Ser | Ile | Ala |
| 625 |     |     |     |     | 630 |     |     |     |     | 635 |     |     |     |     | 640 |

| Thr | Thr | Asp | Asn | Ser | Phe | Thr | Glu | Ile | Pro | Ala | Lys | Thr | Ile | Asn | Val |
|     |     |     |     | 645 |     |     |     |     | 650 |     |     |     |     | 655 |     |

| His | Leu | Thr | Asn | Gln | Gly | Ser | Ser | Asp | Val | Phe | Leu | Asp | Arg | Ile | Glu |
|     |     |     | 660 |     |     |     |     | 665 |     |     |     |     | 670 |     |     |

| Phe | Ile | Pro | Phe | Ser | Leu | Pro | Leu | Ile | Tyr | His | Gly | Ser | Tyr | Asn | Thr |
|     |     | 675 |     |     |     |     | 680 |     |     |     |     | 685 |     |     |     |

| Ser | Ser | Gly | Ala | Asp | Asp | Val | Leu | Trp | Ser | Ser | Ser | Asn | Met | Asn | Tyr |
|     | 690 |     |     |     |     | 695 |     |     |     |     | 700 |     |     |     |     |

| Tyr | Asp | Ile | Ile | Val | Asn | Gly | Gln | Ala | Asn | Ser | Ser | Ser | Ile | Ala | Ser |
| 705 |     |     |     |     | 710 |     |     |     |     | 715 |     |     |     |     | 720 |

| Ser | Met | His | Leu | Leu | Asn | Lys | Gly | Lys | Val | Ile | Lys | Thr | Ile | Asp | Ile |
|     |     |     |     | 725 |     |     |     |     | 730 |     |     |     |     | 735 |     |

| Pro | Gly | His | Ser | Glu | Thr | Phe | Phe | Ala | Thr | Phe | Pro | Val | Pro | Glu | Gly |
|     |     |     | 740 |     |     |     |     | 745 |     |     |     |     | 750 |     |     |

| Phe | Asn | Glu | Val | Arg | Ile | Leu | Ala | Gly | Leu | Pro | Glu | Val | Ser | Gly | Asn |
|     |     | 755 |     |     |     |     | 760 |     |     |     |     | 765 |     |     |     |

| Ile | Thr | Val | Gln | Ser | Asn | Asn | Pro | Pro | Gln | Pro | Ser | Asn | Asn | Gly | Gly |
|     | 770 |     |     |     |     | 775 |     |     |     |     | 780 |     |     |     |     |

| Gly | Asp | Gly | Gly | Gly | Asn | Gly | Gly | Asp | Gly | Gly | Gln | Tyr | Asn | Phe |
| 785 |     |     |     |     | 790 |     |     |     |     | 795 |     |     |     | 800 |

| Ser | Leu | Ser | Gly | Ser | Asp | His | Thr | Thr | Ile | Tyr | His | Gly | Lys | Leu | Glu |
|     |     |     |     | 805 |     |     |     |     | 810 |     |     |     |     | 815 |     |

| Thr | Gly | Ile | His | Val | Gln | Gly | Asn | Tyr | Thr | Tyr | Thr | Gly | Thr | Pro | Val |
|     |     |     | 820 |     |     |     |     | 825 |     |     |     |     | 830 |     |     |

| Leu | Ile | Leu | Asn | Ala | Tyr | Arg | Asn | Asn | Thr | Val | Val | Ser | Ser | Ile | Pro |
|     |     | 835 |     |     |     |     | 840 |     |     |     |     | 845 |     |     |     |

| Val | Tyr | Ser | Pro | Phe | Asp | Ile | Thr | Ile | Gln | Thr | Glu | Ala | Asp | Ser | Leu |
|     | 850 |     |     |     |     | 855 |     |     |     |     | 860 |     |     |     |     |

| Glu | Leu | Glu | Leu | Gln | Pro | Arg | Tyr | Gly | Phe | Ala | Thr | Val | Asn | Gly | Thr |
| 865 |     |     |     |     | 870 |     |     |     |     | 875 |     |     |     |     | 880 |

| Ala | Thr | Val | Lys | Ser | Pro | Asn | Val | Asn | Tyr | Asp | Arg | Ser | Phe | Lys | Leu |
|     |     |     |     | 885 |     |     |     |     | 890 |     |     |     |     | 895 |     |

| Pro | Ile | Asp | Leu | Gln | Asn | Ile | Thr | Thr | Gln | Val | Asn | Ala | Leu | Phe | Ala |
|     |     |     |     | 900 |     |     |     |     | 905 |     |     |     |     | 910 |     |

| Ser | Gly | Thr | Gln | Asn | Met | Leu | Ala | His | Asn | Val | Ser | Asp | His | Asp | Ile |
|     |     |     |     | 915 |     |     |     |     | 920 |     |     |     |     | 925 |     |

| Glu | Glu | Val | Val | Leu | Lys | Val | Asp | Ala | Leu | Ser | Asp | Glu | Val | Phe | Gly |
|     |     |     | 930 |     |     |     |     | 935 |     |     |     |     | 940 |     |     |

```
Asp Glu Lys Lys Ala Leu Arg Lys Leu Val Asn Gln Ala Lys Arg Leu
945                 950                 955                 960

Ser Arg Ala Arg Asn Leu Leu Ile Gly Gly Ser Phe Glu Asn Trp Asp
                965                 970                 975

Ala Trp Tyr Lys Gly Arg Asn Val Val Thr Val Ser Asp His Glu Leu
            980                 985                 990

Phe Lys Ser Asp His Val Leu Leu Pro Pro Gly Leu Ser Pro Ser
        995                 1000                1005

Tyr Ile Phe Gln Lys Val Glu Glu Ser Lys Leu Lys Pro Asn Thr Arg
1010                1015                1020

Tyr Ile Val Ser Gly Phe Ile Ala His Gly Lys Asp Leu Glu Ile Val
1025                1030                1035                1040

Val Ser Arg Tyr Gly Gln Glu Val Gln Lys Val Val Gln Val Pro Tyr
                1045                1050                1055

Gly Glu Ala Phe Pro Leu Thr Ser Asn Gly Pro Val Cys Cys Pro Pro
                1060                1065                1070

Arg Ser Thr Ser Asn Gly Thr Leu Gly Asp Pro His Phe Phe Ser Tyr
                1075                1080                1085

Ser Ile Asp Val Gly Ala Leu Asp Leu Gln Ala Asn Pro Gly Ile Glu
                1090                1095                1100

Phe Gly Leu Arg Ile Val Asn Pro Thr Gly Met Ala Arg Val Ser Asn
1105                1110                1115                1120

Leu Glu Ile Arg Glu Asp Arg Pro Leu Ala Ala Asn Glu Ile Arg Gln
                1125                1130                1135

Val Gln Arg Val Ala Arg Asn Trp Arg Thr Glu Tyr Glu Lys Glu Arg
                1140                1145                1150

Ala Glu Val Thr Ser Leu Ile Gln Pro Val Ile Asn Arg Ile Asn Gly
                1155                1160                1165

Leu Tyr Glu Asn Gly Asn Trp Asn Gly Ser Ile Arg Ser Asp Ile Ser
                1170                1175                1180

Tyr Gln Asn Ile Asp Ala Ile Val Leu Pro Thr Leu Pro Lys Leu Arg
1185                1190                1195                1200

His Trp Phe Met Ser Asp Arg Phe Ser Glu Gln Gly Asp Ile Met Ala
                1205                1210                1215

Lys Phe Gln Gly Ala Leu Asn Arg Ala Tyr Ala Gln Leu Glu Gln Ser
                1220                1225                1230

Thr Leu Leu His Asn Gly His Phe Thr Lys Asp Ala Ala Asn Trp Thr
                1235                1240                1245

Ile Glu Gly Asp Ala His Gln Ile Thr Leu Glu Asp Gly Arg Arg Val
                1250                1255                1260

Leu Arg Leu Pro Asp Trp Ser Ser Ser Val Ser Gln Met Ile Glu Ile
1265                1270                1275                1280

Glu Asn Phe Asn Pro Asp Lys Glu Tyr Asn Leu Val Phe His Gly Gln
                1285                1290                1295

Gly Glu Gly Thr Val Thr Leu Glu His Gly Glu Glu Thr Lys Tyr Ile
                1300                1305                1310

Glu Thr His Thr His His Phe Ala Asn Phe Thr Thr Ser Gln Arg Gln
                1315                1320                1325

Gly Leu Thr Phe Glu Ser Asn Lys Val Thr Val Thr Ile Ser Ser Glu
                1330                1335                1340

Asp Gly Glu Phe Leu Val Asp Asn Ile Ala Leu Val Glu Ala Pro Leu
1345                1350                1355                1360

Pro Thr Asp Asp Gln Asn Ser Glu Gly Asn Thr Ala Ser Ser Thr Asn
                1365                1370                1375
```

Ser Asp Thr Ser Met Asn Asn Asn Gln
          1380                    1385

( 2 ) INFORMATION FOR SEQ ID NO:3:

( i ) SEQUENCE CHARACTERISTICS:
        ( A ) LENGTH: 3867 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis
        ( B ) STRAIN: PS17
        ( C ) INDIVIDUAL ISOLATE: PS17b ( v i i ) IMMEDIATE SOURCE:
        ( B ) CLONE: E. coli NM522(pMYC1628) NRRL B-18652

( x i ) SEQUENCE DESCRIPTION: SEQ ID NO:3:

ATGGCAATTT TAAATGAATT ATATCCATCT GTACCTTATA ATGTATTGGC GTATACGCCA 60

CCCTCTTTTT TACCTGATGC GGGTACACAA GCTACACCTG CTGACTTAAC AGCTTATGAA 120

CAATTGTTGA AAAATTTAGA AAAAGGGATA AATGCTGGAA CTTATTCGAA AGCAATAGCT 180

GATGTACTTA AAGGTATTTT TATAGATGAT ACAATAAATT ATCAAACATA TGTAAATATT 240

GGTTTAAGTT TAATTACATT AGCTGTACCG GAAATTGGTA TTTTTACACC TTTCATCGGT 300

TTGTTTTTTG CTGCATTGAA TAAACATGAT GCTCCACCTC CTCCTAATGC AAAAGATATA 360

TTTGAGGCTA TGAAACCAGC GATTCAAGAG ATGATTGATA GAACTTTAAC TGCGGATGAG 420

CAAACATTTT TAAATGGGGA AATAAGTGGT TTACAAAATT TAGCAGCAAG ATACCAGTCT 480

ACAATGGATG ATATTCAAAG CCATGGAGGA TTTAATAAGG TAGATTCTGG ATTAATTAAA 540

AAGTTTACAG ATGAGGTACT ATCTTTAAAT AGTTTTTATA CAGATCGTTT ACCTGTATTT 600

ATTACAGATA ATACAGCGGA TCGAACTTTG TTAGGTCTTC CTTATTATGC TATACTTGCG 660

AGCATGCATC TTATGTTATT AAGAGATATC ATTACTAAGG GTCCGACATG GGATTCTAAA 720

ATTAATTTCA CACCAGATGC AATTGATTCC TTTAAAACCG ATATTAAAAA TAATATAAAG 780

CTTTACTCTA AAACTATTTA TGACGTATTT CAGAAGGGAC TTGCTTCATA CGGAACGCCT 840

TCTGATTTAG AGTCCTTTGC AAAAAAACAA AAATATATTG AAATTATGAC AACACATTGT 900

TTAGATTTTG CAAGATTGTT TCCTACTTTT GATCCAGATC TTTATCCAAC AGGATCAGGT 960

GATATAAGTT TACAAAAAAC ACGTAGAATT CTTTCTCCTT TTATCCCTAT ACGTACTGCA 1020

GATGGGTTAA CATTAAATAA TACTTCAATT GATACTTCAA ATTGGCCTAA TTATGAAAAT 1080

GGGAATGGCG CGTTTCCAAA CCCAAAAGAA AGAATATTAA AACAATTCAA ACTGTATCCT 1140

AGTTGGAGAG CGGCACAGTA CGGTGGGCTT TTACAACCTT ATTTATGGGC AATAGAAGTC 1200

CAAGATTCTG TAGAGACTCG TTTGTATGGG CAGCTTCCAG CTGTAGATCC ACAGGCAGGG 1260

CCTAATTATG TTTCCATAGA TTCTTCTAAT CCAATCATAC AAATAAATAT GGATACTTGG 1320

AAAACACCAC CACAAGGTGC GAGTGGGTGG AATACAAATT TAATGAGAGG AAGTGTAAGC 1380

GGGTTAAGTT TTTTACAACG AGATGGTACG AGACTTAGTG CTGGTATGGG TGGTGGTTTT 1440

GCTGATACAA TATATAGTCT CCCTGCAACT CATTATCTTT CTTATCTCTA TGGAACTCCT 1500

TATCAAACTT CTGATAACTA TTCTGGTCAC GTTGGTGCAT TGGTAGGTGT GAGTACGCCT 1560

| | | | | | |
|---|---|---|---|---|---|
| CAAGAGGCTA | CTCTTCCTAA | TATTATAGGT | CAACCAGATG | AACAGGGAAA | TGTATCTACA | 1620 |
| ATGGGATTTC | CGTTTGAAAA | AGCTTCTTAT | GGAGGTACAG | TTGTTAAAGA | ATGGTAAAT | 1680 |
| GGTGCGAATG | CGATGAAGCT | TTCTCCTGGG | CAATCTATAG | GTATTCCTAT | TACAAATGTA | 1740 |
| ACAAGTGGAG | AATATCAAAT | TCGTTGTCGT | TATGCAAGTA | ATGATAATAC | TAACGTTTTC | 1800 |
| TTTAATGTAG | ATACTGGTGG | AGCAAATCCA | ATTTTCCAAC | AGATAAACTT | TGCATCTACT | 1860 |
| GTAGATAATA | ATACGGGAGT | ACAAGGAGCA | AATGGTGTCT | ATGTAGTCAA | ATCTATTGCT | 1920 |
| ACAACTGATA | ATTCTTTTAC | AGTAAAAATT | CCTGCGAAGA | CGATTAATGT | TCATTTAACC | 1980 |
| AACCAAGGTT | CTTCTGATGT | CTTTTTAGAT | CGTATTGAGT | TTGTTCCAAT | TCTAGAATCA | 2040 |
| AATACTGTAA | CTATATTCAA | CAATTCATAT | ACTACAGGTT | CAGCAAATCT | TATACCAGCA | 2100 |
| ATAGCTCCTC | TTTGGAGTAC | TAGTTCAGAT | AAAGCCCTTA | CAGGTTCTAT | GTCAATAACA | 2160 |
| GGTCGAACTA | CCCCTAACAG | TGATGATGCT | TTGCTTCGAT | TTTTAAAAC | TAATTATGAT | 2220 |
| ACACAAACCA | TTCCTATTCC | GGGTTCCGGA | AAAGATTTTA | CAAATACTCT | AGAAATACAA | 2280 |
| GACATAGTTT | CTATTGATAT | TTTTGTCGGA | TCTGGTCTAC | ATGGATCCGA | TGGATCTATA | 2340 |
| AAATTAGATT | TTACCAATAA | TAATAGTGGT | AGTGGTGGCT | CTCCAAAGAG | TTTCACCGAG | 2400 |
| CAAAATGATT | TAGAGAATAT | CACAACACAA | GTGAATGCTC | TATTCACATC | TAATACACAA | 2460 |
| GATGCACTTG | CAACAGATGT | GAGTGATCAT | GATATTGAAG | AAGTGGTTCT | AAAAGTAGAT | 2520 |
| GCATTATCTG | ATGAAGTGTT | TGGAAAAGAG | AAAAAAACAT | TGCGTAAATT | TGTAAATCAA | 2580 |
| GCGAAGCGCT | TAAGCAAGGC | GCGTAATCTC | CTGGTAGGAG | GCAATTTTGA | TAACTTGGAT | 2640 |
| GCTTGGTATA | GAGGAAGAAA | TGTAGTAAAC | GTATCTAATC | ACGAACTGTT | GAAGAGTGAT | 2700 |
| CATGTATTAT | TACCACCACC | AGGATTGTCT | CCATCTTATA | TTTTCCAAAA | AGTGGAGGAA | 2760 |
| TCTAAATTAA | AACGAAATAC | ACGTTATACG | GTTTCTGGAT | TTATTGCGCA | TGCAACAGAT | 2820 |
| TTAGAAATTG | TGGTTTCTCG | TTATGGGCAA | GAAATAAAGA | AAGTGGTGCA | AGTTCCTTAT | 2880 |
| GGAGAAGCAT | TCCCATTAAC | ATCAAGTGGA | CCAGTTTGTT | GTATCCCACA | TTCTACAAGT | 2940 |
| AATGGAACTT | TAGGCAATCC | ACATTTCTTT | AGTTACAGTA | TTGATGTAGG | TGCATTAGAT | 3000 |
| GTAGACACAA | ACCCTGGTAT | TGAATTCGGT | CTTCGTATTG | TAAATCCAAC | TGGAATGGCA | 3060 |
| CGCGTAAGCA | ATTTGGAAAT | TCGTGAAGAT | CGTCCATTAG | CAGCAAATGA | AATACGACAA | 3120 |
| GTACAACGTG | TCGCAAGAAA | TTGGAGAACC | GAGTATGAGA | AAGAACGTGC | GGAAGTAACA | 3180 |
| AGTTTAATTC | AACCTGTTAT | CAATCGAATC | AATGGATTGT | ATGACAATGG | AAATTGGAAC | 3240 |
| GGTTCTATTC | GTTCAGATAT | TTCGTATCAG | AATATAGACG | CGATTGTATT | ACCAACGTTA | 3300 |
| CCAAAGTTAC | GCCATTGGTT | TATGTCAGAT | AGATTTAGTG | AACAAGGAGA | TATCATGGCT | 3360 |
| AAATTCCAAG | GTGCATTAAA | TCGTGCGTAT | GCACAACTGG | AACAAAATAC | GCTTCTGCAT | 3420 |
| AATGGTCATT | TTACAAAAGA | TGCAGCCAAT | GGACGGTAG | AAGGCGATGC | ACATCAGGTA | 3480 |
| GTATTAGAAG | ATGGTAAACG | TGTATTACGA | TTGCCAGATT | GGTCTTCGAG | TGTGTCTCAA | 3540 |
| ACGATTGAAA | TCGAGAATTT | TGATCCAGAT | AAAGAATATC | AATTAGTATT | TCATGGGCAA | 3600 |
| GGAGAAGGAA | CGGTTACGTT | GGAGCATGGA | GAAGAAACAA | AATATATAGA | AACGCATACA | 3660 |
| CATCATTTTG | CGAATTTTAC | AACTTCTCAA | CGTCAAGGAC | TCACGTTTGA | ATCAAATAAA | 3720 |
| GTGACAGTGA | CCATTTCTTC | AGAAGATGGA | GAATTCTTAG | TGGATAATAT | TGCGCTTGTG | 3780 |
| GAAGCTCCTC | TTCCTACAGA | TGACCAAAAT | TCTGAGGGAA | ATACGGCTTC | CAGTACGAAT | 3840 |
| AGCGATACAA | GTATGAACAA | CAATCAA | | | | 3867 |

-continued ( 2 ) INFORMATION FOR SEQ ID NO:4:

( i ) SEQUENCE CHARACTERISTICS:
( A ) LENGTH: 1289 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( B ) STRAIN: PS17
( C ) INDIVIDUAL ISOLATE: PS17b ( v i i ) IMMEDIATE SOURCE:
( B ) CLONE: E. coli NM522(pMYC1628) NRRL B-18652

( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ala | Ile | Leu | Asn | Glu | Leu | Tyr | Pro | Ser | Val | Pro | Tyr | Asn | Val | Leu |
| 1 | | | | 5 | | | | | 10 | | | | | 15 | |
| Ala | Tyr | Thr | Pro | Pro | Ser | Phe | Leu | Pro | Asp | Ala | Gly | Thr | Gln | Ala | Thr |
| | | | 20 | | | | | 25 | | | | | 30 | | |
| Pro | Ala | Asp | Leu | Thr | Ala | Tyr | Glu | Gln | Leu | Leu | Lys | Asn | Leu | Glu | Lys |
| | | 35 | | | | | 40 | | | | | 45 | | | |
| Gly | Ile | Asn | Ala | Gly | Thr | Tyr | Ser | Lys | Ala | Ile | Ala | Asp | Val | Leu | Lys |
| | 50 | | | | | 55 | | | | | 60 | | | | |
| Gly | Ile | Phe | Ile | Asp | Asp | Thr | Ile | Asn | Tyr | Gln | Thr | Tyr | Val | Asn | Ile |
| 65 | | | | | 70 | | | | | 75 | | | | | 80 |
| Gly | Leu | Ser | Leu | Ile | Thr | Leu | Ala | Val | Pro | Glu | Ile | Gly | Ile | Phe | Thr |
| | | | | 85 | | | | | 90 | | | | | 95 | |
| Pro | Phe | Ile | Gly | Leu | Phe | Phe | Ala | Ala | Leu | Asn | Lys | His | Asp | Ala | Pro |
| | | | 100 | | | | | 105 | | | | | 110 | | |
| Pro | Pro | Pro | Asn | Ala | Lys | Asp | Ile | Phe | Glu | Ala | Met | Lys | Pro | Ala | Ile |
| | | 115 | | | | | 120 | | | | | 125 | | | |
| Gln | Glu | Met | Ile | Asp | Arg | Thr | Leu | Thr | Ala | Asp | Glu | Gln | Thr | Phe | Leu |
| | 130 | | | | | 135 | | | | | 140 | | | | |
| Asn | Gly | Glu | Ile | Ser | Gly | Leu | Gln | Asn | Leu | Ala | Ala | Arg | Tyr | Gln | Ser |
| 145 | | | | | 150 | | | | | 155 | | | | | 160 |
| Thr | Met | Asp | Asp | Ile | Gln | Ser | His | Gly | Gly | Phe | Asn | Lys | Val | Asp | Ser |
| | | | | 165 | | | | | 170 | | | | | 175 | |
| Gly | Leu | Ile | Lys | Lys | Phe | Thr | Asp | Glu | Val | Leu | Ser | Leu | Asn | Ser | Phe |
| | | | 180 | | | | | 185 | | | | | 190 | | |
| Tyr | Thr | Asp | Arg | Leu | Pro | Val | Phe | Ile | Thr | Asp | Asn | Thr | Ala | Asp | Arg |
| | | 195 | | | | | 200 | | | | | 205 | | | |
| Thr | Leu | Leu | Gly | Leu | Pro | Tyr | Tyr | Ala | Ile | Leu | Ala | Ser | Met | His | Leu |
| | 210 | | | | | 215 | | | | | 220 | | | | |
| Met | Leu | Leu | Arg | Asp | Ile | Ile | Thr | Lys | Gly | Pro | Thr | Trp | Asp | Ser | Lys |
| 225 | | | | | 230 | | | | | 235 | | | | | 240 |
| Ile | Asn | Phe | Thr | Pro | Asp | Ala | Ile | Asp | Ser | Phe | Lys | Thr | Asp | Ile | Lys |
| | | | | 245 | | | | | 250 | | | | | 255 | |
| Asn | Asn | Ile | Lys | Leu | Tyr | Ser | Lys | Thr | Ile | Tyr | Asp | Val | Phe | Gln | Lys |
| | | | 260 | | | | | 265 | | | | | 270 | | |
| Gly | Leu | Ala | Ser | Tyr | Gly | Thr | Pro | Ser | Asp | Leu | Glu | Ser | Phe | Ala | Lys |
| | | 275 | | | | | 280 | | | | | 285 | | | |
| Lys | Gln | Lys | Tyr | Ile | Glu | Ile | Met | Thr | Thr | His | Cys | Leu | Asp | Phe | Ala |
| | 290 | | | | | 295 | | | | | 300 | | | | |

```
Arg  Leu  Phe  Pro  Thr  Phe  Asp  Pro  Asp  Leu  Tyr  Pro  Thr  Gly  Ser  Gly
305                 310                 315                 320

Asp  Ile  Ser  Leu  Gln  Lys  Thr  Arg  Arg  Ile  Leu  Ser  Pro  Phe  Ile  Pro
                    325                 330                 335

Ile  Arg  Thr  Ala  Asp  Gly  Leu  Thr  Leu  Asn  Asn  Thr  Ser  Ile  Asp  Thr
               340                 345                 350

Ser  Asn  Trp  Pro  Asn  Tyr  Glu  Asn  Gly  Asn  Gly  Ala  Phe  Pro  Asn  Pro
          355                 360                 365

Lys  Glu  Arg  Ile  Leu  Lys  Gln  Phe  Lys  Leu  Tyr  Pro  Ser  Trp  Arg  Ala
     370                 375                 380

Ala  Gln  Tyr  Gly  Gly  Leu  Leu  Gln  Pro  Tyr  Leu  Trp  Ala  Ile  Glu  Val
385                 390                 395                 400

Gln  Asp  Ser  Val  Glu  Thr  Arg  Leu  Tyr  Gly  Gln  Leu  Pro  Ala  Val  Asp
               405                 410                 415

Pro  Gln  Ala  Gly  Pro  Asn  Tyr  Val  Ser  Ile  Asp  Ser  Ser  Asn  Pro  Ile
               420                 425                 430

Ile  Gln  Ile  Asn  Met  Asp  Thr  Trp  Lys  Thr  Pro  Pro  Gln  Gly  Ala  Ser
          435                 440                 445

Gly  Trp  Asn  Thr  Asn  Leu  Met  Arg  Gly  Ser  Val  Ser  Gly  Leu  Ser  Phe
450                 455                 460

Leu  Gln  Arg  Asp  Gly  Thr  Arg  Leu  Ser  Ala  Gly  Met  Gly  Gly  Gly  Phe
465                 470                 475                 480

Ala  Asp  Thr  Ile  Tyr  Ser  Leu  Pro  Ala  Thr  His  Tyr  Leu  Ser  Tyr  Leu
               485                 490                 495

Tyr  Gly  Thr  Pro  Tyr  Gln  Thr  Ser  Asp  Asn  Tyr  Ser  Gly  His  Val  Gly
               500                 505                 510

Ala  Leu  Val  Gly  Val  Ser  Thr  Pro  Gln  Glu  Ala  Thr  Leu  Pro  Asn  Ile
          515                 520                 525

Ile  Gly  Gln  Pro  Asp  Glu  Gln  Gly  Asn  Val  Ser  Thr  Met  Gly  Phe  Pro
     530                 535                 540

Phe  Glu  Lys  Ala  Ser  Tyr  Gly  Gly  Thr  Val  Val  Lys  Glu  Trp  Leu  Asn
545                 550                 555                 560

Gly  Ala  Asn  Ala  Met  Lys  Leu  Ser  Pro  Gly  Gln  Ser  Ile  Gly  Ile  Pro
               565                 570                 575

Ile  Thr  Asn  Val  Thr  Ser  Gly  Glu  Tyr  Gln  Ile  Arg  Cys  Arg  Tyr  Ala
               580                 585                 590

Ser  Asn  Asp  Asn  Thr  Asn  Val  Phe  Phe  Asn  Val  Asp  Thr  Gly  Gly  Ala
          595                 600                 605

Asn  Pro  Ile  Phe  Gln  Gln  Ile  Asn  Phe  Ala  Ser  Thr  Val  Asp  Asn  Asn
     610                 615                 620

Thr  Gly  Val  Gln  Gly  Ala  Asn  Gly  Val  Tyr  Val  Val  Lys  Ser  Ile  Ala
625                 630                 635                 640

Thr  Thr  Asp  Asn  Ser  Phe  Thr  Val  Lys  Ile  Pro  Ala  Lys  Thr  Ile  Asn
               645                 650                 655

Val  His  Leu  Thr  Asn  Gln  Gly  Ser  Ser  Asp  Val  Phe  Leu  Asp  Arg  Ile
               660                 665                 670

Glu  Phe  Val  Pro  Ile  Leu  Glu  Ser  Asn  Thr  Val  Thr  Ile  Phe  Asn  Asn
          675                 680                 685

Ser  Tyr  Thr  Thr  Gly  Ser  Ala  Asn  Leu  Ile  Pro  Ala  Ile  Ala  Pro  Leu
     690                 695                 700

Trp  Ser  Thr  Ser  Ser  Asp  Lys  Ala  Leu  Thr  Gly  Ser  Met  Ser  Ile  Thr
705                 710                 715                 720

Gly  Arg  Thr  Thr  Pro  Asn  Ser  Asp  Asp  Ala  Leu  Leu  Arg  Phe  Phe  Lys
```

```
                              725                        730                        735
Thr   Asn   Tyr   Asp   Thr   Gln   Thr   Ile   Pro   Ile   Pro   Gly   Ser   Gly   Lys   Asp
                  740                     745                     750
Phe   Thr   Asn   Thr   Leu   Glu   Ile   Gln   Asp   Ile   Val   Ser   Ile   Asp   Ile   Phe
            755                           760                           765
Val   Gly   Ser   Gly   Leu   His   Gly   Ser   Asp   Gly   Ser   Ile   Lys   Leu   Asp   Phe
      770                           775                           780
Thr   Asn   Asn   Asn   Ser   Gly   Ser   Gly   Gly   Ser   Pro   Lys   Ser   Phe   Thr   Glu
785                           790                           795                           800
Gln   Asn   Asp   Leu   Glu   Asn   Ile   Thr   Thr   Gln   Val   Asn   Ala   Leu   Phe   Thr
                        805                           810                           815
Ser   Asn   Thr   Gln   Asp   Ala   Leu   Ala   Thr   Asp   Val   Ser   Asp   His   Asp   Ile
                  820                           825                           830
Glu   Glu   Val   Val   Leu   Lys   Val   Asp   Ala   Leu   Ser   Asp   Glu   Val   Phe   Gly
                  835                           840                           845
Lys   Glu   Lys   Lys   Thr   Leu   Arg   Lys   Phe   Val   Asn   Gln   Ala   Lys   Arg   Leu
            850                           855                           860
Ser   Lys   Ala   Arg   Asn   Leu   Leu   Val   Gly   Gly   Asn   Phe   Asp   Asn   Leu   Asp
865                           870                           875                           880
Ala   Trp   Tyr   Arg   Gly   Arg   Asn   Val   Val   Asn   Val   Ser   Asn   His   Glu   Leu
                        885                           890                           895
Leu   Lys   Ser   Asp   His   Val   Leu   Leu   Pro   Pro   Gly   Leu   Ser   Pro   Ser
                  900                           905                           910
Tyr   Ile   Phe   Gln   Lys   Val   Glu   Glu   Ser   Lys   Leu   Lys   Arg   Asn   Thr   Arg
            915                           920                           925
Tyr   Thr   Val   Ser   Gly   Phe   Ile   Ala   His   Ala   Thr   Asp   Leu   Glu   Ile   Val
      930                           935                           940
Val   Ser   Arg   Tyr   Gly   Gln   Glu   Ile   Lys   Lys   Val   Val   Gln   Val   Pro   Tyr
945                           950                           955                           960
Gly   Glu   Ala   Phe   Pro   Leu   Thr   Ser   Ser   Gly   Pro   Val   Cys   Cys   Ile   Pro
                        965                           970                           975
His   Ser   Thr   Ser   Asn   Gly   Thr   Leu   Gly   Asn   Pro   His   Phe   Phe   Ser   Tyr
                  980                           985                           990
Ser   Ile   Asp   Val   Gly   Ala   Leu   Asp   Val   Asp   Thr   Asn   Pro   Gly   Ile   Glu
            995                          1000                          1005
Phe   Gly   Leu   Arg   Ile   Val   Asn   Pro   Thr   Gly   Met   Ala   Arg   Val   Ser   Asn
      1010                          1015                          1020
Leu   Glu   Ile   Arg   Glu   Asp   Arg   Pro   Leu   Ala   Ala   Asn   Glu   Ile   Arg   Gln
1025                          1030                          1035                          1040
Val   Gln   Arg   Val   Ala   Arg   Asn   Trp   Arg   Thr   Glu   Tyr   Glu   Lys   Glu   Arg
                        1045                          1050                          1055
Ala   Glu   Val   Thr   Ser   Leu   Ile   Gln   Pro   Val   Ile   Asn   Arg   Ile   Asn   Gly
                  1060                          1065                          1070
Leu   Tyr   Asp   Asn   Gly   Asn   Trp   Asn   Gly   Ser   Ile   Arg   Ser   Asp   Ile   Ser
            1075                          1080                          1085
Tyr   Gln   Asn   Ile   Asp   Ala   Ile   Val   Leu   Pro   Thr   Leu   Pro   Lys   Leu   Arg
      1090                          1095                          1100
His   Trp   Phe   Met   Ser   Asp   Arg   Phe   Ser   Glu   Gln   Gly   Asp   Ile   Met   Ala
1105                          1110                          1115                          1120
Lys   Phe   Gln   Gly   Ala   Leu   Asn   Arg   Ala   Tyr   Ala   Gln   Leu   Glu   Gln   Asn
                        1125                          1130                          1135
Thr   Leu   Leu   His   Asn   Gly   His   Phe   Thr   Lys   Asp   Ala   Ala   Asn   Trp   Thr
                  1140                          1145                          1150
```

|     | Val | Glu | Gly | Asp      | Ala | His | Gln | Val | Val      | Leu | Glu | Asp | Gly      | Lys | Arg | Val |
|-----|-----|-----|-----|----------|-----|-----|-----|-----|----------|-----|-----|-----|----------|-----|-----|-----|
|     |     |     |     | 1155     |     |     |     |     | 1160     |     |     |     | 1165     |     |     |     |

|     | Leu | Arg | Leu | Pro      | Asp | Trp | Ser | Ser | Ser      | Val | Ser | Gln | Thr      | Ile | Glu | Ile |
|     |     |     |     | 1170     |     |     | 1175 |     |          |     |     |     | 1180     |     |     |     |

|     | Glu | Asn | Phe | Asp      | Pro | Asp | Lys | Glu | Tyr      | Gln | Leu | Val | Phe      | His | Gly | Gln |
|     | 1185 |    |     |          |     | 1190 |     |     |          |     | 1195 |    |          |     |     | 1200 |

|     | Gly | Glu | Gly | Thr      | Val | Thr | Leu | Glu | His      | Gly | Glu | Glu | Thr      | Lys | Tyr | Ile |
|     |     |     |     | 1205     |     |     |     |     | 1210     |     |     |     |          |     | 1215 |    |

|     | Glu | Thr | His | Thr      | His | His | Phe | Ala | Asn      | Phe | Thr | Thr | Ser      | Gln | Arg | Gln |
|     |     |     |     | 1220     |     |     |     |     | 1225     |     |     |     | 1230     |     |     |     |

|     | Gly | Leu | Thr | Phe      | Glu | Ser | Asn | Lys | Val      | Thr | Val | Thr | Ile      | Ser | Ser | Glu |
|     |     |     |     | 1235     |     |     |     |     | 1240     |     |     |     | 1245     |     |     |     |

|     | Asp | Gly | Glu | Phe      | Leu | Val | Asp | Asn | Ile      | Ala | Leu | Val | Glu      | Ala | Pro | Leu |
|     |     |     |     | 1250     |     |     |     |     | 1255     |     |     |     | 1260     |     |     |     |

|     | Pro | Thr | Asp | Asp      | Gln | Asn | Ser | Glu | Gly      | Asn | Thr | Ala | Ser      | Ser | Thr | Asn |
|     | 1265 |    |     |          |     | 1270 |    |     |          |     | 1275 |    |          |     |     | 1280 |

|     | Ser | Asp | Thr | Ser      | Met | Asn | Asn | Asn | Gln      |
|     |     |     |     | 1285     |     |     |     |     |          |

(2) INFORMATION FOR SEQ ID NO:5:

(i) SEQUENCE CHARACTERISTICS:
        (A) LENGTH: 3771 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus thuringiensis
        (C) INDIVIDUAL ISOLATE: 33F2

(vii) IMMEDIATE SOURCE:

```
AAAATATTTG GAGATAAACC AAATGCAAAA AATATATTTG AAGAGCTCAA GCCTCAAATT    360
GAAGCATTAA TTCAACAAGA TATAACAAAC TATCAAGATG CAATTAATCA AAAAAAATTT    420
GACAGTCTTC AGAAAACAAT TAATCTATAT ACAGTAGCTA TAGATAACAA TGATTACGTA    480
ACAGCAAAAA CGCAACTCGA AAATCTAAAT TCTATACTTA CCTCAGATAT CTCCATATTT    540
ATTCCAGAAG GATATGAAAC TGGAGGTTTA CCTTATTATG CTATGGTTGC TAATGCTCAT    600
ATATTATTGT TAAGAGACGC TATAGTTAAT GCAGAGAAAT TAGGCTTTAG TGATAAAGAA    660
GTAGACACAC ATAAAAAATA TATCAAAATG ACAATACACA ATCATACTGA AGCAGTAATA    720
AAAGCATTCT TAAATGGACT TGACAAATTT AAGAGTTTAG ATGTAAATAG CTATAATAAA    780
AAAGCAAATT ATATTAAGG TATGACAGAA ATGGTTCTTG ATCTAGTTGC TCTATGGCCA    840
ACTTTCGATC CAGATCATTA TCAAAAGAA GTAGAAATTG AATTTACAAG AACTATTTCT    900
TCTCCAATTT ACCAACCTGT ACCTAAAAAC ATGCAAAATA CCTCTAGCTC TATTGTACCT    960
AGCGATCTAT TTCACTATCA AGGAGATCTT GTAAAATTAG AATTTTCTAC AAGAACGGAC   1020
AACGATGGTC TTGCAAAAAT TTTTACTGGT ATTCGAAACA CATTCTACAA ATCGCCTAAT   1080
ACTCATGAAA CATACCATGT AGATTTTAGT TATAATACCC AATCTAGTGG TAATATTTCA   1140
AGAGGCTCTT CAAATCCGAT TCCAATTGAT CTTAATAATC CCATTATTTC AACTTGTATT   1200
AGAAATTCAT TTTATAAGGC AATAGCGGGA TCTTCTGTTT TAGTTAATTT TAAAGATGGC   1260
ACTCAAGGGT ATGCATTTGC CCAAGCACCA ACAGGAGGTG CCTGGGACCA TTCTTTTATT   1320
GAATCTGATG GTGCCCCAGA AGGGCATAAA TTAAACTATA TTTATACTTC TCCAGGTGAT   1380
ACATTAAGAG ATTTCATCAA TGTATATACT CTTATAAGTA CTCCAACTAT AAATGAACTA   1440
TCAACAGAAA AAATCAAAGG CTTTCCTGCG GAAAAAGGAT ATATCAAAAA TCAAGGGATC   1500
ATGAAATATT ACGGTAAACC AGAATATATT AATGGAGCTC AACCAGTTAA TCTGGAAAAC   1560
CAGCAAACAT TAATATTCGA ATTTCATGCT TCAAAAACAG CTCAATATAC CATTCGTATA   1620
CGTTATGCCA GTACCCAAGG AACAAAAGGT TATTTTCGTT TAGATAATCA GGAACTGCAA   1680
ACGCTTAATA TACCTACTTC ACACAACGGT TATGTAACCG GTAATATTGG TGAAAATTAT   1740
GATTTATATA CAATAGGTTC ATATACAATT ACAGAAGGTA ACCATACTCT TCAAATCCAA   1800
CATAATGATA AAAATGGAAT GGTTTTAGAT CGTATTGAAT TTGTTCCTAA AGATTCACTT   1860
CAAGATTCAC CTCAAGATTC ACCTCCAGAA GTTCACGAAT CAACAATTAT TTTTGATAAA   1920
TCATCTCCAA CTATATGGTC TTCTAACAAA CACTCATATA GCCATATACA TTTAGAAGGA   1980
TCATATACAA GTCAGGGAAG TTATCCACAC AATTTATTAA TTAATTTATT TCATCCTACA   2040
GACCCTAACA GAAATCATAC TATTCATGTT AACAATGGTG ATATGAATGT TGATTATGGA   2100
AAAGATTCTG TAGCCGATGG GTTAAATTTT AATAAAATAA CTGCTACGAT ACCAAGTGAT   2160
GCTTGGTATA GCGGTACTAT TACTTCTATG CACTTATTTA ATGATAATAA TTTTAAAACA   2220
ATAACTCCTA AATTTGAACT TTCTAATGAA TTAGAAAACA TCACAACTCA AGTAAATGCT   2280
TTATTCGCAT CTAGTGCACA AGATACTCTC GCAAGTAATG TAAGTGATTA CTGGATTGAA   2340
CAGGTCGTTA TGAAAGTCGA TGCCTTATCA GATGAAGTAT TTGGAAAAGA GAAAAAGCA   2400
TTACGTAAAT TGGTAAATCA AGCAAAACGT CTCAGTAAAA TACGAAATCT TCTCATAGGT   2460
GGTAATTTTG ACAATTTAGT CGCTTGGTAT ATGGGAAAAG ATGTAGTAAA AGAATCGGAT   2520
CATGAATTAT TTAAAAGTGA TCATGTCTTA CTACCTCCCC CAACATTCCA TCCTTCTTAT   2580
ATTTTCCAAA AGGTGGAAGA ATCAAAACTA AAACCAAATA CACGTTATAC TATTTCTGGT   2640
TTTATCGCAC ATGGAGAAGA TGTAGAGCTT GTTGTCTCTC GTTATGGGCA AGAAATACAA   2700
```

-continued

| | | | | | | |
|---|---|---|---|---|---|---|
| AAAGTGATGC | AAGTGCCATA | TGAAGAAGCA | CTTCCTCTTA | CATCTGAATC | TAATTCTAGT | 2760 |
| TGTTGTGTTC | CAAATTTAAA | TATAAATGAA | ACACTAGCTG | ATCCACATTT | CTTTAGTTAT | 2820 |
| AGCATCGATG | TTGGTTCTCT | GGAAATGGAA | GCGAATCCTG | GTATTGAATT | TGGTCTCCGT | 2880 |
| ATTGTCAAAC | CAACAGGTAT | GGCACGTGTA | AGTAATTTAG | AAATTCGAGA | AGACCGTCCA | 2940 |
| TTAACAGCAA | AAGAAATTCG | TCAAGTACAA | CGTGCAGCAA | GAGATTGGAA | ACAAAACTAT | 3000 |
| GAACAAGAAC | GAACAGAGAT | CACAGCTATA | ATTCAACCTG | TTCTTAATCA | AATTAATGCG | 3060 |
| TTATACGAAA | ATGAAGATTG | GAATGGTTCT | ATTCGTTCAA | ATGTTTCCTA | TCATGATCTA | 3120 |
| GAGCAAATTA | TGCTTCCTAC | TTTATTAAAA | ACTGAGGAAA | TAAATTGTAA | TTATGATCAT | 3180 |
| CCAGCTTTTT | TATTAAAAGT | ATATCATTGG | TTTATGACAG | ATCGTATAGG | AGAACATGGT | 3240 |
| ACTATTTTAG | CACGTTTCCA | AGAAGCATTA | GATCGTGCAT | ATACACAATT | AGAAAGTCGT | 3300 |
| AATCTCCTGC | ATAACGGTCA | TTTTACAACT | GATACAGCGA | ATTGGACAAT | AGAAGGAGAT | 3360 |
| GCCCATCATA | CAATCTTAGA | AGATGGTAGA | CGTGTGTTAC | GTTTACCAGA | TTGGTCTTCT | 3420 |
| AATGCAACTC | AAACAATTGA | AATTGAAGAT | TTTGACTTAG | ATCAAGAATA | CCAATTGCTC | 3480 |
| ATTCATGCAA | AAGGAAAAGG | TTCCATTACT | TTACAACATG | GAGAAGAAAA | CGAATATGTG | 3540 |
| GAAACACATA | CTCATCATAC | AAATGATTTT | ATAACATCCC | AAAATATTCC | TTTCACTTTT | 3600 |
| AAAGGAAATC | AAATTGAAGT | CCATATTACT | TCAGAAGATG | GAGAGTTTTT | AATCGATCAC | 3660 |
| ATTACAGTAA | TAGAAGTTTC | TAAAACAGAC | ACAAATACAA | ATATTATTGA | AAATTCACCA | 3720 |
| ATCAATACAA | GTATGAATAG | TAATGTAAGA | GTAGATATAC | CAAGAAGTCT | C | 3771 |

( 2 ) INFORMATION FOR SEQ ID NO:6:

( i ) SEQUENCE CHARACTERISTICS:
( A ) LENGTH: 1257 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( C ) INDIVIDUAL ISOLATE: PS33F2

( v i i ) IMMEDIATE SOURCE:
( B ) CLONE: E. coli NM522(pMYC2316) B- 18785

( i x ) FEATURE:
( A ) NAME/KEY: Protein
( B ) LOCATION: 1..1257

( x i ) SEQUENCE DESCRIPTION: SEQ ID NO:6:

```
Met Ala Thr Leu Asn Glu Val Tyr Pro Val Asn Tyr Asn Val Leu Ser
1               5                   10                  15

Ser Asp Ala Phe Gln Gln Leu Asp Thr Thr Gly Phe Lys Ser Lys Tyr
            20                  25                  30

Asp Glu Met Ile Lys Ala Phe Glu Lys Lys Trp Lys Lys Gly Ala Lys
        35                  40                  45

Gly Lys Asp Leu Leu Asp Val Ala Trp Thr Tyr Ile Thr Thr Gly Glu
    50                  55                  60

Ile Asp Pro Leu Asn Val Ile Lys Gly Val Leu Ser Val Leu Thr Leu
65                  70                  75                  80

Ile Pro Glu Val Gly Thr Val Ala Ser Ala Ala Ser Thr Ile Val Ser
```

|   |   |   |   |   | 85 |   |   |   |   | 90 |   |   |   |   | 95 |   |   |
|---|---|---|---|---|---|---|---|---|---|---|---|---|---|---|---|---|---|
| Phe | Ile | Trp | Pro 100 | Lys | Ile | Phe | Gly | Asp 105 | Lys | Pro | Asn | Ala | Lys 110 | Asn | Ile |
| Phe | Glu | Glu 115 | Leu | Lys | Pro | Gln | Ile 120 | Glu | Ala | Leu | Ile | Gln 125 | Gln | Asp | Ile |
| Thr | Asn 130 | Tyr | Gln | Asp | Ala | Ile 135 | Asn | Gln | Lys | Lys | Phe 140 | Asp | Ser | Leu | Gln |
| Lys 145 | Thr | Ile | Asn | Leu | Tyr 150 | Thr | Val | Ala | Ile | Asp 155 | Asn | Asn | Asp | Tyr | Val 160 |
| Thr | Ala | Lys | Thr | Gln 165 | Leu | Glu | Asn | Leu | Asn 170 | Ser | Ile | Leu | Thr | Ser 175 | Asp |
| Ile | Ser | Ile | Phe 180 | Ile | Pro | Glu | Gly | Tyr 185 | Glu | Thr | Gly | Gly | Leu 190 | Pro | Tyr |
| Tyr | Ala | Met 195 | Val | Ala | Asn | Ala | His 200 | Ile | Leu | Leu | Leu | Arg 205 | Asp | Ala | Ile |
| Val | Asn 210 | Ala | Glu | Lys | Leu | Gly 215 | Phe | Ser | Asp | Lys | Glu 220 | Val | Asp | Thr | His |
| Lys 225 | Lys | Tyr | Ile | Lys | Met 230 | Thr | Ile | His | Asn | His 235 | Thr | Glu | Ala | Val | Ile 240 |
| Lys | Ala | Phe | Leu | Asn 245 | Gly | Leu | Asp | Lys | Phe 250 | Lys | Ser | Leu | Asp | Val 255 | Asn |
| Ser | Tyr | Asn | Lys 260 | Lys | Ala | Asn | Tyr | Ile 265 | Lys | Gly | Met | Thr | Glu 270 | Met | Val |
| Leu | Asp | Leu 275 | Val | Ala | Leu | Trp | Pro 280 | Thr | Phe | Asp | Pro | Asp 285 | His | Tyr | Gln |
| Lys | Glu 290 | Val | Glu | Ile | Glu | Phe 295 | Thr | Arg | Thr | Ile | Ser 300 | Ser | Pro | Ile | Tyr |
| Gln 305 | Pro | Val | Pro | Lys | Asn 310 | Met | Gln | Asn | Thr | Ser 315 | Ser | Ser | Ile | Val | Pro 320 |
| Ser | Asp | Leu | Phe | His 325 | Tyr | Gln | Gly | Asp | Leu 330 | Val | Lys | Leu | Glu | Phe 335 | Ser |
| Thr | Arg | Thr | Asp 340 | Asn | Asp | Gly | Leu | Ala 345 | Lys | Ile | Phe | Thr | Gly 350 | Ile | Arg |
| Asn | Thr | Phe 355 | Tyr | Lys | Ser | Pro | Asn 360 | Thr | His | Glu | Thr | Tyr 365 | His | Val | Asp |
| Phe | Ser 370 | Tyr | Asn | Thr | Gln | Ser 375 | Ser | Gly | Asn | Ile | Ser 380 | Arg | Gly | Ser | Ser |
| Asn 385 | Pro | Ile | Pro | Ile | Asp 390 | Leu | Asn | Asn | Pro | Ile 395 | Ile | Ser | Thr | Cys | Ile 400 |
| Arg | Asn | Ser | Phe | Tyr 405 | Lys | Ala | Ile | Ala | Gly 410 | Ser | Ser | Val | Leu | Val 415 | Asn |
| Phe | Lys | Asp | Gly 420 | Thr | Gln | Gly | Tyr | Ala 425 | Phe | Ala | Gln | Ala | Pro 430 | Thr | Gly |
| Gly | Ala | Trp 435 | Asp | His | Ser | Phe | Ile 440 | Glu | Ser | Asp | Gly | Ala 445 | Pro | Glu | Gly |
| His | Lys 450 | Leu | Asn | Tyr | Ile | Tyr 455 | Thr | Ser | Pro | Gly | Asp 460 | Thr | Leu | Arg | Asp |
| Phe 465 | Ile | Asn | Val | Tyr | Thr 470 | Leu | Ile | Ser | Thr | Pro 475 | Thr | Ile | Asn | Glu | Leu 480 |
| Ser | Thr | Glu | Lys | Ile 485 | Lys | Gly | Phe | Pro | Ala 490 | Glu | Lys | Gly | Tyr | Ile 495 | Lys |
| Asn | Gln | Gly | Ile 500 | Met | Lys | Tyr | Tyr | Gly 505 | Lys | Pro | Glu | Tyr | Ile 510 | Asn | Gly |

| | | | | | | | | | | | | | | |
|---|---|---|---|---|---|---|---|---|---|---|---|---|---|---|
| Ala | Gln | Pro 515 | Val | Asn | Leu | Glu | Asn 520 | Gln | Gln | Thr | Leu | Ile 525 | Phe | Glu | Phe |
| His | Ala 530 | Ser | Lys | Thr | Ala | Gln 535 | Tyr | Thr | Ile | Arg | Ile 540 | Arg | Tyr | Ala | Ser |
| Thr 545 | Gln | Gly | Thr | Lys | Gly 550 | Tyr | Phe | Arg | Leu | Asp 555 | Asn | Gln | Glu | Leu | Gln 560 |
| Thr | Leu | Asn | Ile | Pro 565 | Thr | Ser | His | Asn | Gly 570 | Tyr | Val | Thr | Gly | Asn 575 | Ile |
| Gly | Glu | Asn | Tyr 580 | Asp | Leu | Tyr | Thr | Ile 585 | Gly | Ser | Tyr | Thr | Ile 590 | Thr | Glu |
| Gly | Asn | His 595 | Thr | Leu | Gln | Ile 600 | Gln | His | Asn | Asp | Lys 605 | Asn | Gly | Met | Val |
| Leu | Asp 610 | Arg | Ile | Glu | Phe | Val 615 | Pro | Lys | Asp | Ser | Leu 620 | Gln | Asp | Ser | Pro |
| Gln 625 | Asp | Ser | Pro | Pro | Glu 630 | Val | His | Glu | Ser | Thr 635 | Ile | Ile | Phe | Asp | Lys 640 |
| Ser | Ser | Pro | Thr | Ile 645 | Trp | Ser | Ser | Asn | Lys 650 | His | Ser | Tyr | Ser | His 655 | Ile |
| His | Leu | Glu | Gly 660 | Ser | Tyr | Thr | Ser | Gln 665 | Gly | Ser | Tyr | Pro | His 670 | Asn | Leu |
| Leu | Ile 675 | Asn | Leu | Phe | His | Pro 680 | Thr | Asp | Pro | Asn | Arg 685 | Asn | His | Thr | Ile |
| His | Val 690 | Asn | Asn | Gly | Asp | Met 695 | Asn | Val | Asp | Tyr | Gly 700 | Lys | Asp | Ser | Val |
| Ala 705 | Asp | Gly | Leu | Asn | Phe 710 | Asn | Lys | Ile | Thr | Ala 715 | Thr | Ile | Pro | Ser | Asp 720 |
| Ala | Trp | Tyr | Ser | Gly 725 | Thr | Ile | Thr | Ser | Met 730 | His | Leu | Phe | Asn | Asp 735 | Asn |
| Asn | Phe | Lys | Thr 740 | Ile | Thr | Pro | Lys | Phe 745 | Glu | Leu | Ser | Asn | Glu 750 | Leu | Glu |
| Asn | Ile | Thr 755 | Thr | Gln | Val | Asn | Ala 760 | Leu | Phe | Ala | Ser | Ser 765 | Ala | Gln | Asp |
| Thr | Leu 770 | Ala | Ser | Asn | Val | Ser 775 | Asp | Tyr | Trp | Ile | Glu 780 | Gln | Val | Val | Met |
| Lys 785 | Val | Asp | Ala | Leu | Ser 790 | Asp | Glu | Val | Phe | Gly 795 | Lys | Glu | Lys | Lys | Ala 800 |
| Leu | Arg | Lys | Leu | Val 805 | Asn | Gln | Ala | Lys | Arg 810 | Leu | Ser | Lys | Ile | Arg 815 | Asn |
| Leu | Leu | Ile | Gly 820 | Gly | Asn | Phe | Asp | Asn 825 | Leu | Val | Ala | Trp | Tyr 830 | Met | Gly |
| Lys | Asp | Val 835 | Val | Lys | Glu | Ser | Asp 840 | His | Glu | Leu | Phe | Lys 845 | Ser | Asp | His |
| Val | Leu 850 | Leu | Pro | Pro | Pro | Thr 855 | Phe | His | Pro | Ser | Tyr 860 | Ile | Phe | Gln | Lys |
| Val 865 | Glu | Glu | Ser | Lys | Leu 870 | Lys | Pro | Asn | Thr | Arg 875 | Tyr | Thr | Ile | Ser | Gly 880 |
| Phe | Ile | Ala | His | Gly 885 | Glu | Asp | Val | Glu | Leu 890 | Val | Val | Ser | Arg | Tyr 895 | Gly |
| Gln | Glu | Ile | Gln 900 | Lys | Val | Met | Gln | Val 905 | Pro | Tyr | Glu | Glu | Ala 910 | Leu | Pro |
| Leu | Thr | Ser 915 | Glu | Ser | Asn | Ser | Ser 920 | Cys | Cys | Val | Pro | Asn 925 | Leu | Asn | Ile |
| Asn | Glu 930 | Thr | Leu | Ala | Asp | Pro 935 | His | Phe | Phe | Ser | Tyr 940 | Ser | Ile | Asp | Val |

```
Gly Ser Leu Glu Met Glu Ala Asn Pro Gly Ile Glu Phe Gly Leu Arg
945                 950                 955                     960

Ile Val Lys Pro Thr Gly Met Ala Arg Val Ser Asn Leu Glu Ile Arg
                965                 970                     975

Glu Asp Arg Pro Leu Thr Ala Lys Glu Ile Arg Gln Val Gln Arg Ala
            980                 985                 990

Ala Arg Asp Trp Lys Gln Asn Tyr Glu Gln Glu Arg Thr Glu Ile Thr
        995                 1000                1005

Ala Ile Ile Gln Pro Val Leu Asn Gln Ile Asn Ala Leu Tyr Glu Asn
    1010                1015                1020

Glu Asp Trp Asn Gly Ser Ile Arg Ser Asn Val Ser Tyr His Asp Leu
1025                1030                1035                1040

Glu Gln Ile Met Leu Pro Thr Leu Leu Lys Thr Glu Glu Ile Asn Cys
                1045                1050                1055

Asn Tyr Asp His Pro Ala Phe Leu Leu Lys Val Tyr His Trp Phe Met
            1060                1065                1070

Thr Asp Arg Ile Gly Glu His Gly Thr Ile Leu Ala Arg Phe Gln Glu
            1075                1080                1085

Ala Leu Asp Arg Ala Tyr Thr Gln Leu Glu Ser Arg Asn Leu Leu His
    1090                1095                1100

Asn Gly His Phe Thr Thr Asp Thr Ala Asn Trp Thr Ile Glu Gly Asp
1105                1110                1115                1120

Ala His His Thr Ile Leu Glu Asp Gly Arg Arg Val Leu Arg Leu Pro
            1125                1130                1135

Asp Trp Ser Ser Asn Ala Thr Gln Thr Ile Glu Ile Glu Asp Phe Asp
            1140                1145                1150

Leu Asp Gln Glu Tyr Gln Leu Leu Ile His Ala Lys Gly Lys Gly Ser
        1155                1160                1165

Ile Thr Leu Gln His Gly Glu Glu Asn Glu Tyr Val Glu Thr His Thr
    1170                1175                1180

His His Thr Asn Asp Phe Ile Thr Ser Gln Asn Ile Pro Phe Thr Phe
1185                1190                1195                1200

Lys Gly Asn Gln Ile Glu Val His Ile Thr Ser Glu Asp Gly Glu Phe
            1205                1210                1215

Leu Ile Asp His Ile Thr Val Ile Glu Val Ser Lys Thr Asp Thr Asn
            1220                1225                1230

Thr Asn Ile Ile Glu Asn Ser Pro Ile Asn Thr Ser Met Asn Ser Asn
        1235                1240                1245

Val Arg Val Asp Ile Pro Arg Ser Leu
1250                1255
```

( 2 ) INFORMATION FOR SEQ ID NO:7:

( i ) SEQUENCE CHARACTERISTICS:
        ( A ) LENGTH: 3738 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus thuringiensis ( v i i ) IMMEDIATE SOURCE:
    ( A ) LIBRARY: Lambdagem (TM) - 11 LIBRARY
    ( B ) CLONE: 86Q3a ( x i ) SEQUENCE DESCRIPTION: SEQ ID NO:7:

| | | | | | | |
|---|---|---|---|---|---|---|
| ATGGCAACAA | TTAATGAGTT | GTATCCAGTT | CCTTATAATG | TGCTAGCTCA | TCCAATTAAA | 60 |
| GAAGTCGATG | ATCCTTATTC | TTGGTCAAAT | TTATTAAAGG | GTATACAAGA | AGGTTGGGAA | 120 |
| GAATGGGGAA | AAACAGGACA | AAAAAAACTT | TTTGAAGACC | ATCTTACGAT | TGCATGGAAT | 180 |
| CTTTATAAAA | CAGGAAAATT | AGATTATTTC | GCTTTGACAA | AAGCATCAAT | ATCATTGATT | 240 |
| GGATTTATTC | CAGGGGCAGA | AGCAGCAGTT | CCCTTTATTA | ATATGTTTGT | AGACTTTGTT | 300 |
| TGGCCTAAAT | TATTTGGTGC | GAATACAGAA | GGAAAAGATC | AACAGTTGTT | TAATGCTATC | 360 |
| ATGGATGCAG | TTAATAAAAT | GGTAGATAAT | AAGTTCTTAA | GTTATAATCT | TAGTACACTT | 420 |
| AATAAAACAA | TTGAAGGACT | TCAAGGTAAT | TTAGGCCTAT | TTCAAAATGC | TATACAAGTA | 480 |
| GCCATTTGTC | AAGGCAGTAC | ACCAGAAAGA | GTAAATTTTG | ATCAAAATTG | TACACCATGT | 540 |
| AATCCAAATC | AACCTTGTAA | AGATGATTTG | GATAGAGTTG | CTTCACGTTT | TGATACGGCT | 600 |
| AATTCTCAAT | TCACACAGCA | TTTACCAGAA | TTTAAAAATC | CTTGGTCGGA | TGAAAACTCT | 660 |
| ACTCAGGAAT | TTAAAAGAAC | ATCTGTTGAA | TTAACTTTAC | CAATGTATAC | AACAGTAGCT | 720 |
| ACGTTACATC | TTTTATTATA | TGAAGGATAT | ATAGAATTTA | TGACAAAATG | GAATTTTCAC | 780 |
| AATGAACAAT | ATTTAAATAA | TTTAAAGGTA | GAATTACAAC | AATTGATACA | CTCATATTCA | 840 |
| GAAACTGTTC | GTACAAGTTT | CCTTCAATTT | TTACCTACCT | TGAATAATCG | TTCAAAATCA | 900 |
| TCCGTAAATG | CTTATAACCG | TTATGTCCGC | AATATGACTG | TTAACTGTTT | AGATATTGCT | 960 |
| GCTACATGGC | CTACATTTGA | TACACATAAT | TATCATCAAG | GTGGTAAATT | AGATTTAACT | 1020 |
| CGTATTATTC | TTTCAGATAC | AGCAGGACCA | ATAGAAGAAT | ATACTACTGG | CGACAAAACT | 1080 |
| TCAGGACCTG | AACATAGTAA | CATTACACCA | AATAATATTC | TAGATACACC | ATCTCCAACA | 1140 |
| TATCAGCACT | CATTTGTATC | TGTTGATTCT | ATTGTATATT | CTAGAAAAGA | ATTACAACAA | 1200 |
| TTAGACATAG | CTACTTATAG | TACAAATAAT | AGTAATAATT | GTCACCCTTA | TGGATTACGA | 1260 |
| CTTTCATATA | CAGATGGAAG | CAGATATGAT | TATGGAGATA | ATCAACCTGA | TTTTACTACT | 1320 |
| TCCAATAACA | ATTATTGTCA | TAATAGCTAT | ACTGCCCCTA | TTACACTTGT | GAATGCACGA | 1380 |
| CATTTATATA | ATGCAAAAGG | CTCTTTACAA | AATGTAGAAT | CTTTAGTGGT | TAGTACTGTA | 1440 |
| AATGGTGGAA | GTGGTTCATG | CATTTGTGAT | GCATGGATTA | ATTATTTACG | TCCTCCTCAA | 1500 |
| ACAAGTAAAA | ATGAATCACG | TCCTGATCAA | AAAATTAATG | TTTTGTATCC | AATAACAGAA | 1560 |
| ACTGTAAATA | AGGGGACTGG | AGGAAATTTA | GGAGTTATTT | CTGCCTATGT | TCCAATGGAA | 1620 |
| CTTGTACCAG | AAAACGTTAT | TGGAGATGTT | AATGCTGATA | CTAAATTGCC | ACTTACACAA | 1680 |
| TTAAAGGGCT | TTCCATTTGA | AAAATATGGT | TCTGAGTATA | ATAATCGGGG | TATCTCTCTT | 1740 |
| GTTCGCGAAT | GGATAAATGG | TAACAATGCA | GTTAAACTTT | CTAATAGTCA | ATCTGTTGGC | 1800 |
| ATACAAATTA | CGAATCAAAC | CAAACAAAAA | TATGAAATAC | GTTGCCGTTA | TGCGAGTAAA | 1860 |
| GGAGATAATA | ATGTTTATTT | TAATGTGGAT | TTAAGTGAAA | ATCCATTTAG | AAATTCCATT | 1920 |
| TCTTTTGGAT | CTACTGAAAG | TTCTGTTGTA | GGAGTACAAG | GTGAAATGG | AAAGTATATA | 1980 |
| TTGAAATCAA | TCACAACGGT | AGAAATACCT | GCTGGAAGTT | TCTATGTTCA | TATAACAAAC | 2040 |
| CAAGGTTCTT | CAGATCTCTT | TTTAGATCGT | ATTGAGTTTG | TTCCAAAAAT | CCAATTCCAA | 2100 |
| TTCTGTGATA | ATAATAATCT | TCACTGTGAT | TGTAATAACC | CTGTTGACAC | CGATTGTACA | 2160 |
| TTTTGTTGCG | TTTGCACTAG | TCTTACTGAT | TGTGATTGTA | ATAACCCTCG | TGGCCTAGAT | 2220 |

| | | | | | |
|---|---|---|---|---|---|
| TGTACGCTAT | GTTGTCAGGT | AGAAAATCAG | CTACCTTCTT | TTGTGACACT | TACAGATTTA | 2280 |
| CAAAATATTA | CGACACAAGT | AAATGCATTA | GTTGCATCGA | GCGAACATGA | TACACTTGCA | 2340 |
| ACAGACGTGA | GTGATTATGA | GATTGAAGAA | GTTGTACTGA | AAGTAGATGC | ATTATCTGGT | 2400 |
| GAAGTGTTTG | GAAAAGAGAA | AAAAGCATTG | CGTAAATTGG | TAAATCACAC | AAAACGTTTA | 2460 |
| AGCAAAGCGC | GTAACCTCTT | GATAGGAGGA | AATTTTGATA | ACTTGGATGC | TTGGTACAGA | 2520 |
| GGCCGAAATG | TAGTAAACGT | ATCTGATCAT | GAACTATTTA | AGAGTGATCA | TGTATTATTG | 2580 |
| CCACCACCAA | CACTGTACTC | ATCTTATATG | TTCCAAAAAG | TAGAGGAATC | GAAATTAAAA | 2640 |
| GCGAATACAC | GTTATACTGT | GTCTGGTTTT | ATTGCACATG | CAGAAGATTT | AGAAATTGTT | 2700 |
| GTGTCTCGTT | ATGGGCAAGA | AGTGAAGAAA | GTGGTTCAAG | TTCCATATGG | AGAAGCATTC | 2760 |
| CCATTGACAT | CGAGGGGAGC | GATTTGTTGC | CCTCCACGTT | CTACAAGTAA | TGGAAAACCT | 2820 |
| GCTGATCCAC | ATTTCTTTAG | TTACAGTATT | GATGTGGGAA | CATTAGATGT | AGAAGCAAAC | 2880 |
| CCTGGTATCG | AATTGGGTCT | TCGTATTGTA | GAACGAACTG | GAATGGCACG | TGTAAGTAAT | 2940 |
| TTAGAAATTC | GTGAAGATCG | TCCATTAAAG | AAAAATGAAC | TCCGCAATGT | ACAACGTGCA | 3000 |
| GCAAGAAATT | GGAGAACAGC | ATATGACCAA | GAACGTGCAG | AAGTAACGGC | CTTGATTCAA | 3060 |
| CCTGTATTAA | ATCAAATCAA | TGCGTTGTAT | GAAAATGAAG | ATTGGAATGG | AGCAATTCGT | 3120 |
| TCTGGAGTTT | CTTATCATGA | CTTAGAAGCA | ATTGTTTTAC | CAACATTACC | AAAATTAAAT | 3180 |
| CATTGGTTTA | TGTCTGATAT | GTTAGGGGAA | CAAGGTTCCA | TTTTAGCTCA | ATTTCAAGAA | 3240 |
| GCATTAGATC | GTGCGTATAC | GCAACTCGAA | GAAAGTACAA | TTCTGCATAA | TGGTCATTTC | 3300 |
| ACAACAGATG | CAGCAAATTG | GACGATAGAA | GGCGATGCAC | ATCATGCGAT | ATTAGAAGAT | 3360 |
| GGTAGACGCG | TATTACGTCT | TCCAGATTGG | TCTTCTAGCG | TTTCACAAAC | CATTGAAATA | 3420 |
| GAAAATTTTG | ATCCAGATAA | AGAATATCAG | TTAGTTTTCC | ATGCACAAGG | AGAAGGAACG | 3480 |
| GTCTCCCTTC | AACATGGTGA | AGAAGGAGAA | TATGTGGAAA | CACACCCGCA | TAAGTCTGCG | 3540 |
| AATTTTACAA | CTTCACACCG | TCAAGGAGTC | ACATTTGAAA | CAAATAAAGT | AACAGTTGAA | 3600 |
| ATTACCTCAG | AAGATGGAGA | ATTCCTAGTC | GATCATATTG | CTCTTGTGGA | AGCTCCTCTT | 3660 |
| CCTACAGATG | ACCAAAGTTC | AGATGGAAAT | ACGACTTCCA | ATACGAATAG | CAATACAAGT | 3720 |
| ATGAATAATA | ATCAATAA | | | | | 3738 |

( 2 ) INFORMATION FOR SEQ ID NO:8:

( i ) SEQUENCE CHARACTERISTICS:
    ( A ) LENGTH: 1245 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
    ( A ) ORGANISM: BACILLUS THURINGIENSIS
    ( C ) INDIVIDUAL ISOLATE: PS86Q3

( v i i ) IMMEDIATE SOURCE:
( A ) LIBRARY: LAMBDAGEM (tm) - 11 library
( B ) CLONE: 86Q3A ( x i ) SEQUENCE DESCRIPTION: SEQ ID NO:8:

Met Ala Thr Ile Asn Glu Leu Tyr Pro Val Pro Tyr Asn Val Leu Ala
1 5 10 15

| | | | | | | | | | | | | | | |
|---|---|---|---|---|---|---|---|---|---|---|---|---|---|---|
| His | Pro | Ile | Lys 20 | Glu | Val | Asp | Asp | Pro 25 | Tyr | Ser | Trp | Ser | Asn 30 | Leu | Leu |
| Lys | Gly | Ile | Gln 35 | Glu | Gly | Trp | Glu | Trp 40 | Gly | Lys | Thr | Gly 45 | Gln | Lys |
| Lys | Leu 50 | Phe | Glu | Asp | His | Leu 55 | Thr | Ile | Ala | Trp | Asn 60 | Leu | Tyr | Lys | Thr |
| Gly 65 | Lys | Leu | Asp | Tyr | Phe 70 | Ala | Leu | Thr | Lys | Ala 75 | Ser | Ile | Ser | Leu | Ile 80 |
| Gly | Phe | Ile | Pro | Gly 85 | Ala | Glu | Ala | Ala | Val 90 | Pro | Phe | Ile | Asn | Met 95 | Phe |
| Val | Asp | Phe | Val 100 | Trp | Pro | Lys | Leu | Phe 105 | Gly | Ala | Asn | Thr | Glu 110 | Gly | Lys |
| Asp | Gln | Gln 115 | Leu | Phe | Asn | Ala | Ile 120 | Met | Asp | Ala | Val | Asn 125 | Lys | Met | Val |
| Asp | Asn 130 | Lys | Phe | Leu | Ser | Tyr 135 | Asn | Leu | Ser | Thr | Leu 140 | Asn | Lys | Thr | Ile |
| Glu 145 | Gly | Leu | Gln | Gly | Asn 150 | Leu | Gly | Leu | Phe | Gln 155 | Asn | Ala | Ile | Gln | Val 160 |
| Ala | Ile | Cys | Gln | Gly 165 | Ser | Thr | Pro | Glu | Arg 170 | Val | Asn | Phe | Asp | Gln 175 | Asn |
| Cys | Thr | Pro | Cys 180 | Asn | Pro | Asn | Gln | Pro 185 | Cys | Lys | Asp | Asp | Leu 190 | Asp | Arg |
| Val | Ala | Ser 195 | Arg | Phe | Asp | Thr | Ala 200 | Asn | Ser | Gln | Phe | Thr 205 | Gln | His | Leu |
| Pro | Glu 210 | Phe | Lys | Asn | Pro | Trp 215 | Ser | Asp | Glu | Asn | Ser 220 | Thr | Gln | Glu | Phe |
| Lys 225 | Arg | Thr | Ser | Val | Glu 230 | Leu | Thr | Leu | Pro | Met 235 | Tyr | Thr | Thr | Val | Ala 240 |
| Thr | Leu | His | Leu | Leu 245 | Leu | Tyr | Glu | Gly | Tyr 250 | Ile | Glu | Phe | Met | Thr 255 | Lys |
| Trp | Asn | Phe | His 260 | Asn | Glu | Gln | Tyr | Leu 265 | Asn | Asn | Leu | Lys | Val 270 | Glu | Leu |
| Gln | Gln | Leu 275 | Ile | His | Ser | Tyr | Ser 280 | Glu | Thr | Val | Arg | Thr 285 | Ser | Phe | Leu |
| Gln | Phe 290 | Leu | Pro | Thr | Leu | Asn 295 | Asn | Arg | Ser | Lys | Ser 300 | Ser | Val | Asn | Ala |
| Tyr 305 | Asn | Arg | Tyr | Val | Arg 310 | Asn | Met | Thr | Val | Asn 315 | Cys | Leu | Asp | Ile | Ala 320 |
| Ala | Thr | Trp | Pro | Thr 325 | Phe | Asp | Thr | His | Asn 330 | Tyr | His | Gln | Gly | Gly 335 | Lys |
| Leu | Asp | Leu | Thr 340 | Arg | Ile | Ile | Leu | Ser 345 | Asp | Thr | Ala | Gly | Pro 350 | Ile | Glu |
| Glu | Tyr | Thr 355 | Thr | Gly | Asp | Lys | Thr 360 | Ser | Gly | Pro | Glu | His 365 | Ser | Asn | Ile |
| Thr | Pro 370 | Asn | Asn | Ile | Leu | Asp 375 | Thr | Pro | Ser | Pro | Thr 380 | Tyr | Gln | His | Ser |
| Phe 385 | Val | Ser | Val | Asp | Ser 390 | Ile | Val | Tyr | Ser | Arg 395 | Lys | Glu | Leu | Gln | Gln 400 |
| Leu | Asp | Ile | Ala | Thr 405 | Tyr | Ser | Thr | Asn | Asn 410 | Ser | Asn | Asn | Cys | His 415 | Pro |
| Tyr | Gly | Leu | Arg 420 | Leu | Ser | Tyr | Thr | Asp 425 | Gly | Ser | Arg | Tyr | Asp 430 | Tyr | Gly |
| Asp | Asn | Gln 435 | Pro | Asp | Phe | Thr | Thr 440 | Ser | Asn | Asn | Asn | Tyr 445 | Cys | His | Asn |

```
Ser  Tyr  Thr  Ala  Pro  Ile  Thr  Leu  Val  Asn  Ala  Arg  His  Leu  Tyr  Asn
     450                 455                      460
Ala  Lys  Gly  Ser  Leu  Gln  Asn  Val  Glu  Ser  Leu  Val  Ser  Thr  Val
465                      470                 475                           480
Asn  Gly  Gly  Ser  Gly  Ser  Cys  Ile  Cys  Asp  Ala  Trp  Ile  Asn  Tyr  Leu
                    485                 490                           495
Arg  Pro  Pro  Gln  Thr  Ser  Lys  Asn  Glu  Ser  Arg  Pro  Asp  Gln  Lys  Ile
               500                      505                      510
Asn  Val  Leu  Tyr  Pro  Ile  Thr  Glu  Thr  Val  Asn  Lys  Gly  Thr  Gly  Gly
          515                 520                      525
Asn  Leu  Gly  Val  Ile  Ser  Ala  Tyr  Val  Pro  Met  Glu  Leu  Val  Pro  Glu
     530                 535                      540
Asn  Val  Ile  Gly  Asp  Val  Asn  Ala  Asp  Thr  Lys  Leu  Pro  Leu  Thr  Gln
545                      550                      555                      560
Leu  Lys  Gly  Phe  Pro  Phe  Glu  Lys  Tyr  Gly  Ser  Glu  Tyr  Asn  Asn  Arg
                    565                      570                      575
Gly  Ile  Ser  Leu  Val  Arg  Glu  Trp  Ile  Asn  Gly  Asn  Asn  Ala  Val  Lys
               580                      585                 590
Leu  Ser  Asn  Ser  Gln  Ser  Val  Gly  Ile  Gln  Ile  Thr  Asn  Gln  Thr  Lys
          595                      600                 605
Gln  Lys  Tyr  Glu  Ile  Arg  Cys  Arg  Tyr  Ala  Ser  Lys  Gly  Asp  Asn  Asn
     610                      615                      620
Val  Tyr  Phe  Asn  Val  Asp  Leu  Ser  Glu  Asn  Pro  Phe  Arg  Asn  Ser  Ile
625                      630                      635                      640
Ser  Phe  Gly  Ser  Thr  Glu  Ser  Ser  Val  Val  Gly  Val  Gln  Gly  Glu  Asn
                    645                      650                      655
Gly  Lys  Tyr  Ile  Leu  Lys  Ser  Ile  Thr  Thr  Val  Glu  Ile  Pro  Ala  Gly
               660                      665                      670
Ser  Phe  Tyr  Val  His  Ile  Thr  Asn  Gln  Gly  Ser  Ser  Asp  Leu  Phe  Leu
          675                      680                 685
Asp  Arg  Ile  Glu  Phe  Val  Pro  Lys  Ile  Gln  Phe  Gln  Phe  Cys  Asp  Asn
     690                      695                 700
Asn  Asn  Leu  His  Cys  Asp  Cys  Asn  Asn  Pro  Val  Asp  Thr  Asp  Cys  Thr
705                      710                      715                      720
Phe  Cys  Cys  Val  Cys  Thr  Ser  Leu  Thr  Asp  Cys  Asp  Cys  Asn  Asn  Pro
                    725                      730                      735
Arg  Gly  Leu  Asp  Cys  Thr  Leu  Cys  Cys  Gln  Val  Glu  Asn  Gln  Leu  Pro
               740                      745                 750
Ser  Phe  Val  Thr  Leu  Thr  Asp  Leu  Gln  Asn  Ile  Thr  Thr  Gln  Val  Asn
          755                      760                 765
Ala  Leu  Val  Ala  Ser  Ser  Glu  His  Asp  Thr  Leu  Ala  Thr  Asp  Val  Ser
     770                      775                 780
Asp  Tyr  Glu  Ile  Glu  Glu  Val  Val  Leu  Lys  Val  Asp  Ala  Leu  Ser  Gly
785                 790                      795                           800
Glu  Val  Phe  Gly  Lys  Glu  Lys  Lys  Ala  Leu  Arg  Lys  Leu  Val  Asn  His
               805                      810                      815
Thr  Lys  Arg  Leu  Ser  Lys  Ala  Arg  Asn  Leu  Leu  Ile  Gly  Gly  Asn  Phe
               820                      825                 830
Asp  Asn  Leu  Asp  Ala  Trp  Tyr  Arg  Gly  Arg  Asn  Val  Val  Asn  Val  Ser
          835                      840                 845
Asp  His  Glu  Leu  Phe  Lys  Ser  Asp  His  Val  Leu  Leu  Pro  Pro  Pro  Thr
     850                      855                 860
Leu  Tyr  Ser  Ser  Tyr  Met  Phe  Gln  Lys  Val  Glu  Glu  Ser  Lys  Leu  Lys
```

|     |     |     |     |     |     |     |     |     |     |     |     |     |     |     |
|---|---|---|---|---|---|---|---|---|---|---|---|---|---|---|
| 865 |     |     |     | 870 |     |     |     | 875 |     |     |     | 880 |     |     |
| Ala | Asn | Thr | Arg | Tyr | Thr | Val | Ser | Gly | Phe | Ile | Ala | His | Ala | Glu | Asp |
|     |     |     |     | 885 |     |     |     | 890 |     |     |     | 895 |     |     |
| Leu | Glu | Ile | Val | Val | Ser | Arg | Tyr | Gly | Gln | Glu | Val | Lys | Lys | Val | Val |
|     |     |     | 900 |     |     |     | 905 |     |     |     | 910 |     |     |     |
| Gln | Val | Pro | Tyr | Gly | Glu | Ala | Phe | Pro | Leu | Thr | Ser | Arg | Gly | Ala | Ile |
|     |     | 915 |     |     |     | 920 |     |     |     | 925 |     |     |     |
| Cys | Cys | Pro | Pro | Arg | Ser | Thr | Ser | Asn | Gly | Lys | Pro | Ala | Asp | Pro | His |
|     | 930 |     |     |     | 935 |     |     |     | 940 |     |     |     |
| Phe | Phe | Ser | Tyr | Ser | Ile | Asp | Val | Gly | Thr | Leu | Asp | Val | Glu | Ala | Asn |
| 945 |     |     |     | 950 |     |     |     | 955 |     |     |     | 960 |
| Pro | Gly | Ile | Glu | Leu | Gly | Leu | Arg | Ile | Val | Glu | Arg | Thr | Gly | Met | Ala |
|     |     |     | 965 |     |     |     | 970 |     |     |     | 975 |
| Arg | Val | Ser | Asn | Leu | Glu | Ile | Arg | Glu | Asp | Arg | Pro | Leu | Lys | Lys | Asn |
|     |     |     | 980 |     |     |     | 985 |     |     |     | 990 |
| Glu | Leu | Arg | Asn | Val | Gln | Arg | Ala | Ala | Arg | Asn | Trp | Arg | Thr | Ala | Tyr |
|     |     | 995 |     |     |     | 1000 |     |     |     | 1005 |     |
| Asp | Gln | Glu | Arg | Ala | Glu | Val | Thr | Ala | Leu | Ile | Gln | Pro | Val | Leu | Asn |
|     | 1010 |     |     |     | 1015 |     |     |     | 1020 |     |
| Gln | Ile | Asn | Ala | Leu | Tyr | Glu | Asn | Glu | Asp | Trp | Asn | Gly | Ala | Ile | Arg |
| 1025 |     |     |     | 1030 |     |     |     | 1035 |     |     |     | 1040 |
| Ser | Gly | Val | Ser | Tyr | His | Asp | Leu | Glu | Ala | Ile | Val | Leu | Pro | Thr | Leu |
|     |     |     | 1045 |     |     |     | 1050 |     |     |     | 1055 |
| Pro | Lys | Leu | Asn | His | Trp | Phe | Met | Ser | Asp | Met | Leu | Gly | Glu | Gln | Gly |
|     |     |     | 1060 |     |     |     | 1065 |     |     |     | 1070 |
| Ser | Ile | Leu | Ala | Gln | Phe | Gln | Glu | Ala | Leu | Asp | Arg | Ala | Tyr | Thr | Gln |
|     |     | 1075 |     |     |     | 1080 |     |     |     | 1085 |     |
| Leu | Glu | Glu | Ser | Thr | Ile | Leu | His | Asn | Gly | His | Phe | Thr | Thr | Asp | Ala |
|     | 1090 |     |     |     | 1095 |     |     |     | 1100 |     |
| Ala | Asn | Trp | Thr | Ile | Glu | Gly | Asp | Ala | His | His | Ala | Ile | Leu | Glu | Asp |
| 1105 |     |     |     | 1110 |     |     |     | 1115 |     |     |     | 1120 |
| Gly | Arg | Arg | Val | Leu | Arg | Leu | Pro | Asp | Trp | Ser | Ser | Val | Ser | Gln |
|     |     |     | 1125 |     |     |     | 1130 |     |     |     | 1135 |
| Thr | Ile | Glu | Ile | Glu | Asn | Phe | Asp | Pro | Asp | Lys | Glu | Tyr | Gln | Leu | Val |
|     |     |     | 1140 |     |     |     | 1145 |     |     |     | 1150 |
| Phe | His | Ala | Gln | Gly | Glu | Gly | Thr | Val | Ser | Leu | Gln | His | Gly | Glu | Glu |
|     |     |     | 1155 |     |     |     | 1160 |     |     |     | 1165 |
| Gly | Glu | Tyr | Val | Glu | Thr | His | Pro | His | Lys | Ser | Ala | Asn | Phe | Thr | Thr |
|     |     | 1170 |     |     |     | 1175 |     |     |     | 1180 |     |
| Ser | His | Arg | Gln | Gly | Val | Thr | Phe | Glu | Thr | Asn | Lys | Val | Thr | Val | Glu |
| 1185 |     |     |     | 1190 |     |     |     | 1195 |     |     |     | 1200 |
| Ile | Thr | Ser | Glu | Asp | Gly | Glu | Phe | Leu | Val | Asp | His | Ile | Ala | Leu | Val |
|     |     |     | 1205 |     |     |     | 1210 |     |     |     | 1215 |
| Glu | Ala | Pro | Leu | Pro | Thr | Asp | Asp | Gln | Ser | Ser | Asp | Gly | Asn | Thr | Thr |
|     |     |     | 1220 |     |     |     | 1225 |     |     |     | 1230 |
| Ser | Asn | Thr | Asn | Ser | Asn | Thr | Ser | Met | Asn | Asn | Asn | Gln |
|     |     |     | 1235 |     |     |     | 1240 |     |     |     | 1245 |

( 2 ) INFORMATION FOR SEQ ID NO:9:

( i ) SEQUENCE CHARACTERISTICS:
        ( A ) LENGTH: 2412 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
  ( A ) ORGANISM: Bacillus thuringiensis
  ( C ) INDIVIDUAL ISOLATE: PS63B ( v i i ) IMMEDIATE SOURCE:
  ( B ) CLONE: E. coli NM522(pMYC1642) NRRL B-18961

( x i ) SEQUENCE DESCRIPTION: SEQ ID NO:9:

```
ATGACTTGTC AATTACAAGC GCAACCACTT ATTCCCTATA ACGTACTAGC AGGAGTTCCA   60
ACTAGTAATA CAGGTAGTCC AATCGGCAAT GCAGGTAATC AATTTGATCA GTTTGAGCAA  120
ACCGTTAAAG AGCTCAAGGA AGCATGGGAA GCGTTCCAAA AAAACGGAAG TTTCTCATTA  180
GCAGCTCTTG AAAAGGGATT TGATGCAGCA ATCGGAGGAG GATCCTTTGA TTATTTAGGT  240
TTAGTTCAAG CCGGCCTAGG ATTAGTTGGT ACGCTAGGCG CCGCAATCCC TGGTGTTTCA  300
GTGGCAGTGC CTCTTATTAG CATGCTTGTT GGTGTTTTTT GGCCAAAGGG CACAAACAAC  360
CAAGAAAACC TTATTACAGT TATTGATAAG GAAGTTCAGA GAATACTAGA TGAAAAGCTA  420
TCTGATCAGT TAATAAAGAA ATTGAACGCA GATTTAAATG CTTTTACGGA CCTAGTAACT  480
CGTTTGGAAG AAGTAATAAT AGATGCAACT TTCGAGAATC ACAAGCCTGT ACTACAAGTA  540
AGTAAATCAA ATTATATGAA AGTGGATTCA GCATATTTCT CAACAGGAGG TATTCTTACT  600
CTTGGCATGA GTGATTTTCT TACTGATACC TATTCAAAGC TTACCTTCCC ATTATATGTA  660
CTAGGCGCAA CTATGAAACT TTCAGCATAT CATAGTTATA TACAATTCGG AAATACATGG  720
CTTAATAAAG TTTATGATTT ATCATCAGAT GAGGGAAAAA CAATGTCGCA GGCTTTAGCA  780
CGAGCTAAAC AGCATATGCG CCAAGACATA GCATTTTATA CAAGCCAAGC TTTAAACATG  840
TTTACTGGGA ATCTCCCTTC ATTATCATCT AATAAATATG CAATTAATGA CTATAATGTA  900
TACACTCGAG CAATGGTATT GAATGGCTTA GATATAGTAG CAACATGGCC TACCCTATAT  960
CCAGATGACT ATTCGTCTCA GATAAAACTG GAGAAAACAC GCGTGATCTT TTCAGATATG 1020
GTCGGGCAAA GTGAGAGTAG AGATGGCAGC GTAACGATTA AAAATATTTT TGACAATACA 1080
GATTCACATC AACATGGATC CATAGGTCTC AATTCAATCT CTTATTTCCC AGATGAGTTA 1140
CAGAAAGCAC AACTTCGCAT GTATGATTAT AATCACAAAC CTTATTGTAC GGACTGTTTC 1200
TGCTGGCCGT ATGGAGTGAT TTTAAACTAT AACAAGAATA CCTTTAGATA TGGCGATAAT 1260
GATCCAGGTC TTTCAGGAGA CGTTCAACTC CCAGCACCTA TGAGTGTAGT TAATGCCCAA 1320
ACTCAAACAG CCCAATATAC AGATGGAGAA AACATATGGA CAGATACTGG CCGCAGTTGG 1380
CTTTGTACTC TACGTGGCTA CTGTACTACA AACTGTTTTC CAGGAAGAGG TTGTTATAAT 1440
AATAGTACTG GATATGGAGA AAGTTGCAAT CAATCACTTC CAGGTCAAAA AATACATGCA 1500
CTATATCCTT TTACACAAAC AAATGTGCTG GGACAATCAG GCAAACTAGG ATTGCTAGCA 1560
AGTCATATTC CATATGACCT AAGTCCGAAC AATACGATTG GTGACAAAGA TACAGATTCT 1620
ACGAATATTG TCGCAAAAGG AATTCCAGTG GAAAAAGGGT ATGCATCCAG TGGACAAAAA 1680
GTTGAAATTA TACGAGAGTG GATAAATGGT GCGAATGTAG TTCAATTATC TCCAGGCCAA 1740
TCTTGGGGAA TGGATTTTAC CAATAGCACA GGTGGTCAAT ATATGGTCCG CTGTCGATAT 1800
GCAAGTACAA ACGATACTCC AATCTTTTTT AATTTAGTGT ATGACGGGGG ATCGAATCCT 1860
ATTTATAACC AGATGACATT CCCTGCTACA AAAGAGACTC CAGCTCACGA TTCAGTAGAT 1920
AACAAGATAC TAGGCATAAA AGGAATAAAT GGAAATTATT CACTCATGAA TGTAAAAGAT 1980
TCTGTCGAAC TTCCATCTGG GAAATTTCAT GTTTTTTTCA CAAATAATGG ATCATCTGCT 2040
```

```
ATTTATTTAG ATCGACTTGA GTTTGTTCCT TTAGATCAAC CAGCAGCGCC AACACAGTCA    2100

ACACAACCAA TTAATTATCC TATCACAAGT AGGTTACCTC ATCGTTCCGG AGAACCACCT    2160

GCAATAATAT GGGAGAAATC AGGGAATGTT CGCGGGAATC AACTAACTAT ATCGGCACAA    2220

GGTGTTCCAG AAAATTCCCA AATATATCTT TCGGTGGGTG GCGATCGCCA AATTTTAGAC    2280

CGTAGCAACG GATTTAAATT AGTTAATTAC TCACCTACTT ATTCTTTCAC TAACATTCAG    2340

GCTAGCTCGT CAAATTTAGT AGATATTACA AGTGGTACCA TCACTGGCCA AGTACAAGTA    2400

TCTAATCTAT AA                                                        2412
```

(2) INFORMATION FOR SEQ ID NO:10:

(i) SEQUENCE CHARACTERISTICS:
        (A) LENGTH: 803 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Bacillus thuringiensis
        (C) INDIVIDUAL ISOLATE: PS63B (vii) IMMEDIATE SOURCE:
        (B) CLONE: E. coli NM522(pMY

```
Met Lys Leu Ser Ala Tyr His Ser Tyr Ile Gln Phe Gly Asn Thr Trp
225                 230                 235                 240

Leu Asn Lys Val Tyr Asp Leu Ser Ser Asp Glu Gly Lys Thr Met Ser
            245                 250                 255

Gln Ala Leu Ala Arg Ala Lys Gln His Met Arg Gln Asp Ile Ala Phe
                260                 265                 270

Tyr Thr Ser Gln Ala Leu Asn Met Phe Thr Gly Asn Leu Pro Ser Leu
        275                 280                 285

Ser Ser Asn Lys Tyr Ala Ile Asn Asp Tyr Asn Val Tyr Thr Arg Ala
    290                 295                 300

Met Val Leu Asn Gly Leu Asp Ile Val Ala Thr Trp Pro Thr Leu Tyr
305                 310                 315                 320

Pro Asp Asp Tyr Ser Ser Gln Ile Lys Leu Glu Lys Thr Arg Val Ile
                325                 330                 335

Phe Ser Asp Met Val Gly Gln Ser Glu Ser Arg Asp Gly Ser Val Thr
                340                 345                 350

Ile Lys Asn Ile Phe Asp Asn Thr Asp Ser His Gln His Gly Ser Ile
        355                 360                 365

Gly Leu Asn Ser Ile Ser Tyr Phe Pro Asp Glu Leu Gln Lys Ala Gln
    370                 375                 380

Leu Arg Met Tyr Asp Tyr Asn His Lys Pro Tyr Cys Thr Asp Cys Phe
385                 390                 395                 400

Cys Trp Pro Tyr Gly Val Ile Leu Asn Tyr Asn Lys Asn Thr Phe Arg
                405                 410                 415

Tyr Gly Asp Asn Asp Pro Gly Leu Ser Gly Asp Val Gln Leu Pro Ala
            420                 425                 430

Pro Met Ser Val Val Asn Ala Gln Thr Gln Thr Ala Gln Tyr Thr Asp
        435                 440                 445

Gly Glu Asn Ile Trp Thr Asp Thr Gly Arg Ser Trp Leu Cys Thr Leu
    450                 455                 460

Arg Gly Tyr Cys Thr Thr Asn Cys Phe Pro Gly Arg Gly Cys Tyr Asn
465                 470                 475                 480

Asn Ser Thr Gly Tyr Gly Glu Ser Cys Asn Gln Ser Leu Pro Gly Gln
            485                 490                 495

Lys Ile His Ala Leu Tyr Pro Phe Thr Gln Thr Asn Val Leu Gly Gln
            500                 505                 510

Ser Gly Lys Leu Gly Leu Leu Ala Ser His Ile Pro Tyr Asp Leu Ser
        515                 520                 525

Pro Asn Asn Thr Ile Gly Asp Lys Asp Thr Asp Ser Thr Asn Ile Val
    530                 535                 540

Ala Lys Gly Ile Pro Val Glu Lys Gly Tyr Ala Ser Ser Gly Gln Lys
545                 550                 555                 560

Val Glu Ile Ile Arg Glu Trp Ile Asn Gly Ala Asn Val Val Gln Leu
            565                 570                 575

Ser Pro Gly Gln Ser Trp Gly Met Asp Phe Thr Asn Ser Thr Gly Gly
        580                 585                 590

Gln Tyr Met Val Arg Cys Arg Tyr Ala Ser Thr Asn Asp Thr Pro Ile
    595                 600                 605

Phe Phe Asn Leu Val Tyr Asp Gly Gly Ser Asn Pro Ile Tyr Asn Gln
610                 615                 620

Met Thr Phe Pro Ala Thr Lys Glu Thr Pro Ala His Asp Ser Val Asp
625                 630                 635                 640

Asn Lys Ile Leu Gly Ile Lys Gly Ile Asn Gly Asn Tyr Ser Leu Met
```

|       |       |       |       |       |       |       |       |       | 645   |       |       |       |       | 650   |       |       |       |       | 655   |       |       |
|-------|-------|-------|-------|-------|-------|-------|-------|-------|-------|-------|-------|-------|-------|-------|-------|-------|-------|-------|-------|-------|-------|
| Asn | Val | Lys | Asp | Ser | Val | Glu | Leu | Pro | Ser | Gly | Lys | Phe | His | Val | Phe |
|  |  |  | 660 |  |  |  |  | 665 |  |  |  |  | 670 |  |  |
| Phe | Thr | Asn | Asn | Gly | Ser | Ser | Ala | Ile | Tyr | Leu | Asp | Arg | Leu | Glu | Phe |
|  |  | 675 |  |  |  |  | 680 |  |  |  |  | 685 |  |  |  |
| Val | Pro | Leu | Asp | Gln | Pro | Ala | Pro | Thr | Gln | Ser | Thr | Gln | Pro | Ile |
| 690 |  |  |  |  | 695 |  |  |  |  | 700 |  |  |  |  |
| Asn | Tyr | Pro | Ile | Thr | Ser | Arg | Leu | Pro | His | Arg | Ser | Gly | Glu | Pro | Pro |
| 705 |  |  |  |  | 710 |  |  |  |  | 715 |  |  |  |  | 720 |
| Ala | Ile | Ile | Trp | Glu | Lys | Ser | Gly | Asn | Val | Arg | Gly | Asn | Gln | Leu | Thr |
|  |  |  |  | 725 |  |  |  |  | 730 |  |  |  |  | 735 |  |
| Ile | Ser | Ala | Gln | Gly | Val | Pro | Glu | Asn | Ser | Gln | Ile | Tyr | Leu | Ser | Val |
|  |  |  | 740 |  |  |  |  | 745 |  |  |  |  | 750 |  |  |
| Gly | Gly | Asp | Arg | Gln | Ile | Leu | Asp | Arg | Ser | Asn | Gly | Phe | Lys | Leu | Val |
|  |  | 755 |  |  |  |  | 760 |  |  |  |  | 765 |  |  |  |
| Asn | Tyr | Ser | Pro | Thr | Tyr | Ser | Phe | Thr | Asn | Ile | Gln | Ala | Ser | Ser | Ser |
|  | 770 |  |  |  |  | 775 |  |  |  |  | 780 |  |  |  |  |
| Asn | Leu | Val | Asp | Ile | Thr | Ser | Gly | Thr | Ile | Thr | Gly | Gln | Val | Gln | Val |
| 785 |  |  |  |  | 790 |  |  |  |  | 795 |  |  |  |  | 800 |
| Ser | Asn | Leu |

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

| Arg | Glu | Trp | Ile | Asn | Gly | Ala | Asn |
|-----|-----|-----|-----|-----|-----|-----|-----|
| 1 |  |  |  | 5 |  |  |  |

( 2 ) INFORMATION FOR SEQ ID NO:12:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

AGARTRKWTW AATGGWGCKM A                                                            21

( 2 ) INFORMATION FOR SEQ ID NO:13:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:13:

GARTGGWTAA ATGGTRMSAA                                                            20

( 2 ) INFORMATION FOR SEQ ID NO:14:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:14:

Pro Thr Phe Asp Pro Asp Leu Tyr
1               5

( 2 ) INFORMATION FOR SEQ ID NO:15:

( i ) SEQUENCE CHARACTERISTICS:
      ( A ) LENGTH: 24 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:15:

CCNAC Y TTTK ATCCAGATSW Y TAT                24

( 2 ) INFORMATION FOR SEQ ID NO:16:

( i ) SEQUENCE CHARACTERISTICS:
      ( A ) LENGTH: 24 bases
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:16:

CCWACWTT Y G ATMCASATMW TTAT                24

( 2 ) INFORMATION FOR SEQ ID NO:17:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:17:

Ala Ile Leu Asn Glu Leu Tyr Pro Ser Val Pro Tyr Asn Val
1               5                   10

( 2 ) INFORMATION FOR SEQ ID NO:18:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:18:

Ala Ile Leu Asn Glu Leu Tyr Pro Ser Val Pro Tyr Asn Val
1               5                   10

( 2 ) INFORMATION FOR SEQ ID NO:19:

( i ) SEQUENCE CHARACTERISTICS:
      ( A ) LENGTH: 16 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:19:

```
Met Ala Thr Ile Asn Glu Leu Tyr Pro Asn Val Pro Tyr Asn Val Leu
1               5                   10                  15
```

(2) INFORMATION FOR SEQ ID NO:20:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:20:

```
Gln Leu Gln Ala Gln Pro Leu Ile Pro Tyr Asn Val Leu Ala
1               5                   10
```

(2) INFORMATION FOR SEQ ID NO:21:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:21:

```
Ala Thr Leu Asn Glu Val Tyr Pro Val Asn
1               5                   10
```

(2) INFORMATION FOR SEQ ID NO:22:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:22:

```
Val Gln Arg Ile Leu Asp Glu Lys Leu Ser Phe Gln Leu Ile Lys
1               5                   10                  15
```

(2) INFORMATION FOR SEQ ID NO:23:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:23:

GCAATTTTAA ATGAATTATA TCC                           23

(2) INFORMATION FOR SEQ ID NO:24:

(i) SEQUENCE CHARACTERISTICS:
(A) LENGTH: 17 bases
(B) TYPE: nucleic acid (C) STRANDEDNESS: single
(D) TOPOLOGY: linear (ii) MOLECULE TYPE: DNA (synthetic)

(xi) SEQUENCE DESCRIPTION: SEQ ID NO:24:

CAAYTACAAG CWCAACC    17

(2) INFORMATION FOR SEQ ID NO:25:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:25:

TTCATCTAAA ATTCTTTGWA C    21

(2) INFORMATION FOR SEQ ID NO:26:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:26:

GCWACWTTAA ATGAAGTWTA T    21

(2) INFORMATION FOR SEQ ID NO:27:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:27:

AATGAAGTWT ATCCWGTWAA T    21

(2) INFORMATION FOR SEQ ID NO:28:

(i) SEQUENCE CHARACTERISTICS:
    (A) LENGTH: 38 bases
    (B) TYPE: nucleic acid
    (C) STRANDEDNESS: single
    (D) TOPOLOGY: linear (ii) MOLECULE TYPE: DNA (synthetic)

(xi) SEQUENCE DESCRIPTION: SEQ ID NO:28:

GCAAGCGGCC GCTTATGGAA TAAATTCAAT TYKRTCWA    38

(2) INFORMATION FOR SEQ ID NO:29:

(i) SEQUENCE CHARACTERISTICS:
    (A) LENGTH: 37 bases
    (B) TYPE: nucleic acid
    (C) STRANDEDNESS: single
    (D) TOPOLOGY: linear (ii) MOLECULE TYPE: DNA (synthetic)

( x i ) SEQUENCE DESCRIPTION: SEQ ID NO:29:

AGACTGGATC CATGGCWACW ATWAATGAAT TATA Y CC    37

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:30:

Glu Ser Lys Leu Lys Pro Asn Thr Arg Tyr
1               5                   10

( 2 ) INFORMATION FOR SEQ ID NO:31:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:31:

TAACGTGTAT WCGSTTTTAA TTTWGA Y TC    29

( 2 ) INFORMATION FOR SEQ ID NO:32:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

Tyr Ile Asp Lys Ile Glu Phe Ile Pro
1               5

( 2 ) INFORMATION FOR SEQ ID NO:33:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:33:

TGGAATAAAT TCAATT Y KRT CWA    23

( 2 ) INFORMATION FOR SEQ ID NO:34:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:34:

AGGAACAAA Y TCAAKWCGRT CTA    23

( 2 ) INFORMATION FOR SEQ ID NO:35:

( i ) SEQUENCE CHARACTERISTICS:
       ( A ) LENGTH: 24 bases
       ( B ) TYPE: nucleic acid
       ( C ) STRANDEDNESS: single
       ( D ) TOPOLOGY: linear ( i i ) MOLECULE TYPE: DNA (synthetic)

( x i ) SEQUENCE DESCRIPTION: SEQ ID NO:35:

TTTAGATCGT MTTGARTTTR TWCC                                                              24

( 2 ) INFORMATION FOR SEQ ID NO:36:

( i ) SEQUENCE CHARACTERISTICS:
       ( A ) LENGTH: 5 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:36:

Ile Thr Ser Glu Asp
   1               5

( 2 ) INFORMATION FOR SEQ ID NO:37:

( i ) SEQUENCE CHARACTERISTICS:
       ( A ) LENGTH: 20 bases
       ( B ) TYPE: nucleic acid
       ( C ) STRANDEDNESS: single
       ( D ) TOPOLOGY: linear ( i i ) MOLECULE TYPE: DNA (synthetic)

( x i ) SEQUENCE DESCRIPTION: SEQ ID NO:37:

TCTCCATCTT CTGARGWAAT                                                                   20

( 2 ) INFORMATION FOR SEQ ID NO:38:

( i ) SEQUENCE CHARACTERISTICS:
       ( A ) LENGTH: 8 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:38:

Leu Asp Arg Ile Glu Phe Val Pro
   1               5

( 2 ) INFORMATION FOR SEQ ID NO:39:

( i ) SEQUENCE CHARACTERISTICS:
       ( A ) LENGTH: 731 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: YES ( x i ) SEQUENCE DESCRIPTION: SEQ ID NO:39:

Met Xaa Xaa Xaa Xaa Xaa Xaa Tyr Pro Xaa Xaa Xaa Tyr Xaa Xaa Xaa
   1               5                   10                  15

```
Xaa Xaa Xaa Xaa Xaa Xaa Xaa Xaa Xaa Xaa Xaa Xaa Xaa Xaa Xaa
            20                      25                      30
Xaa Xaa Xaa Xaa Xaa Xaa Xaa Xaa Xaa Xaa Xaa Xaa Xaa Xaa Xaa
        35                      40                      45
Xaa Xaa Xaa Xaa Xaa Xaa Xaa Xaa Xaa Xaa Xaa Xaa Xaa Xaa Xaa
    50                      55                      60
Xaa Xaa Xaa Xaa Xaa Xaa Xaa Xaa Xaa Xaa Xaa Xaa Xaa Xaa Xaa
65                      70                      75                      80
Xaa Xaa Xaa Xaa Xaa Xaa Xaa Xaa Xaa Pro Xaa Xaa Xaa Xaa Xaa
                85                      90                      95
Xaa Xaa Xaa Xaa Xaa Xaa Xaa Xaa Xaa Xaa Xaa Xaa Xaa Xaa Xaa
            100                     105                     110
Xaa Xaa Xaa Xaa Xaa Xaa Lys Xaa Xaa Xaa Xaa Xaa Xaa Xaa Xaa
        115                     120                     125
Xaa Xaa Xaa Xaa Xaa Xaa Xaa Xaa Xaa Xaa Xaa Xaa Xaa Xaa Xaa
    130                     135                     140
Xaa Xaa Xaa Xaa Xaa Xaa Xaa Xaa Xaa Xaa Xaa Xaa Xaa Xaa Xaa
145                     150                     155                     160
Xaa Xaa Xaa Xaa Xaa Xaa Xaa Xaa Xaa Xaa Xaa Xaa Xaa Xaa Xaa
                165                     170                     175
Xaa Xaa Xaa Xaa Xaa Xaa Xaa Xaa Xaa Xaa Xaa Xaa Xaa Xaa Xaa
            180                     185                     190
Xaa Xaa Xaa Xaa Xaa Xaa Xaa Xaa Xaa Xaa Xaa Xaa Xaa Xaa Xaa
        195                     200                     205
Xaa Xaa Xaa Xaa Xaa Xaa Xaa Xaa Xaa Xaa Xaa Xaa Xaa Xaa Xaa
    210                     215                     220
Xaa Xaa Xaa Xaa Xaa Glu Xaa Xaa Xaa Xaa Xaa Xaa Xaa Xaa Xaa
225                     230                     235                     240
Pro Xaa Tyr Xaa Xaa Xaa Xaa Xaa His Xaa Xaa Xaa Xaa Xaa Xaa
                245                     250                     255
Xaa Xaa Xaa Xaa Xaa Xaa Xaa Xaa Xaa Xaa Xaa Xaa Xaa Xaa Xaa
            260                     265                     270
Xaa Xaa Xaa Xaa Xaa Xaa Xaa Xaa Xaa Xaa Xaa Xaa Xaa Xaa Xaa
        275                     280                     285
Xaa Xaa Xaa Xaa Xaa Xaa Xaa Xaa Xaa Xaa Xaa Xaa Xaa Xaa Xaa
    290                     295                     300
Xaa Xaa Xaa Xaa Xaa Xaa Xaa Xaa Xaa Xaa Xaa Xaa Xaa Xaa Tyr
305                     310                     315                     320
Xaa Xaa Xaa Xaa Xaa Xaa Xaa Xaa Xaa Xaa Xaa Xaa Xaa Xaa Pro
                325                     330                     335
Xaa Xaa Xaa Xaa Xaa Xaa Tyr Xaa Xaa Xaa Xaa Xaa Xaa Xaa Xaa
            340                     345                     350
Xaa Xaa Xaa Xaa Xaa Xaa Xaa Xaa Xaa Xaa Xaa Xaa Xaa Xaa Xaa
        355                     360                     365
Xaa Xaa Xaa Xaa Xaa Xaa Xaa Xaa Xaa Xaa Xaa Xaa Xaa Xaa Xaa
    370                     375                     380
Xaa Xaa Xaa Xaa Xaa Xaa Xaa Xaa Xaa Xaa Xaa Xaa Xaa Xaa Xaa
385                     390                     395                     400
Xaa Xaa Xaa Xaa Xaa Xaa Xaa Xaa Xaa Xaa Xaa Xaa Xaa Xaa Xaa
                405                     410                     415
Xaa Xaa Xaa Xaa Xaa Xaa Xaa Xaa Xaa Xaa Xaa Xaa Xaa Xaa Xaa
            420                     425                     430
Xaa Xaa Xaa Xaa Xaa Xaa Xaa Xaa Xaa Xaa Xaa Xaa Xaa Xaa Xaa
```

-continued

|   |   |   |   |   | 435 |   |   |   |   | 440 |   |   |   |   | 445 |
|---|---|---|---|---|---|---|---|---|---|---|---|---|---|---|---|
| Xaa | Xaa 450 | Xaa | Xaa | Xaa | Xaa | Xaa 455 | Xaa | Xaa | Xaa | Xaa | Xaa 460 | Xaa | Xaa | Xaa | Xaa |
| Xaa 465 | Xaa | Xaa | Xaa | Xaa | Xaa 470 | Xaa | Xaa | Pro | Xaa | Xaa 475 | Xaa | Xaa | Xaa | Xaa | Xaa 480 |
| Xaa | Xaa | Xaa | Xaa | Xaa 485 | Xaa | Xaa | Xaa | Xaa | Xaa 490 | Xaa | Xaa | Xaa | Xaa | Xaa 495 | Xaa |
| Xaa | Xaa | Xaa | Xaa 500 | Xaa | Xaa | Xaa | Xaa | Xaa 505 | Xaa | Xaa | Xaa | Xaa | Xaa 510 | Xaa | Xaa |
| Xaa | Xaa | Xaa 515 | Xaa | Xaa | Xaa | Xaa | Xaa 520 | Xaa | Xaa | Xaa | Xaa | Xaa 525 | Xaa | Xaa | Xaa |
| Xaa | Xaa 530 | Xaa | Xaa | Xaa | Xaa | Xaa 535 | Xaa | Xaa | Xaa | Xaa | Xaa 540 | Xaa | Tyr | Xaa | Xaa |
| Xaa 545 | Xaa | Xaa | Xaa | Xaa | Xaa 550 | Xaa | Xaa | Xaa | Xaa | Xaa 555 | Xaa | Xaa | Xaa | Xaa | Xaa 560 |
| Xaa | Xaa | Xaa | Xaa | Xaa 565 | Xaa | Xaa | Xaa | Xaa | Xaa 570 | Xaa | Xaa | Xaa | Xaa | Xaa 575 | Xaa |
| Xaa | Xaa | Xaa | Xaa 580 | Xaa | Xaa | Xaa | Xaa | Xaa 585 | Xaa | Xaa | Xaa | Xaa | Xaa 590 | Xaa | Xaa |
| Xaa | Xaa | Xaa 595 | Xaa | Xaa | Xaa | Xaa | Xaa 600 | Xaa | Xaa | Xaa | Xaa | Xaa 605 | Xaa | Xaa | Xaa |
| Xaa | Xaa 610 | Xaa | Xaa | Xaa | Xaa | Xaa 615 | Xaa | Xaa | Xaa | Xaa | Xaa 620 | Xaa | Xaa | Xaa | Xaa |
| Xaa 625 | Xaa | Xaa | Xaa | Xaa | Xaa 630 | Xaa | Xaa | Xaa | Xaa | Xaa 635 | Xaa | Xaa | Tyr | Xaa | Xaa 640 |
| Xaa | Xaa | Xaa | Xaa | Pro 645 | Xaa | Xaa | Xaa | Xaa | Xaa 650 | Xaa | Xaa | Xaa | Xaa | Xaa 655 | Xaa |
| Xaa | Xaa | Xaa | Xaa 660 | Xaa | Xaa | Xaa | Xaa | Xaa 665 | Xaa | Xaa | Xaa | Xaa | Xaa 670 | Xaa | Xaa |
| Xaa | Xaa | Xaa 675 | Xaa | Xaa | Xaa | Xaa | Xaa 680 | Xaa | Xaa | Xaa | Xaa | Xaa 685 | Xaa | Tyr | Xaa |
| Xaa | Xaa 690 | Xaa | Xaa | Xaa | Xaa | Xaa 695 | Xaa | Xaa | Xaa | Xaa | Xaa 700 | Xaa | Xaa | Xaa | Xaa |
| Xaa 705 | Xaa | Xaa | Xaa | Xaa | Xaa 710 | Xaa | Xaa | Xaa | Xaa | Xaa 715 | Xaa | Xaa | Xaa | Xaa | Xaa 720 |
| Xaa | Xaa | Xaa | Xaa | Xaa 725 | Xaa | Xaa | Xaa | Pro | Xaa 730 |   |   |   |   |   |   |

*BACILLUS THURINGIENSIS* GENE ENCODING HYMENOPTERAN-ACTIVE TOXINS

CROSS-REFERENCE TO A RELATED APPLICATION

This is a continuation of application Ser. No. 07/887,980, filed May 22, 1992, now abandoned; which is a continuation-in-part of application Ser. No. 07/703,977, filed May 22, 1991, now U.S. Pat. No. 5,260,058 issued on Nov. 9, 1993, and a continuation-in-part of application Ser. No. 07/797,645, filed Nov. 25, 1991, now U.S. Pat. No. 5,268, 297 issued Dec. 7, 1993.

BACKGROUND OF THE INVENTION

The development of biological control agents as alternatives to chemical insecticides for the control of important pest species is a subject of increasing interest. Concerns for the environment and exposure of man to harmful substances in air, food and water have stimulated legislation and restrictions regarding the use of chemical pesticides, particularly for pests found in the urban environment. Control of insect pests in urban areas is highly desirable but exposure to chemical pesticides in the household and from lawns and gardens is of great concern to the public. If given a choice, most people would use a non-toxic biological control rather than a toxic chemical to control insects in the urban environment. The problem is that very few biological alternatives to chemical insecticides are available for purchase and use by the public.

*Bacillus thutingiensis* (B.t.) produces an insect toxin designated as δ-endotoxin. It is synthesized by the B.t. sporulating cell. The toxin, upon being ingested in its crystalline form by susceptible insects, is transformed into biologically active moieties by the insect gut juice proteases. The primary target is insect cells of the gut epithelium, which are rapidly destroyed.

The reported activity spectrum of B.t. covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thutingiensis* var. israelensis," *Developments in Industrial Microbiology* 22:61–76; Beegle, C. C., (1978) "Use of Entomogenous Bacteria in Agroecosystems," *Developments in Industrial Microbiology* 20:97–104. Krieg, et al. (1983) Z. ang. Ent. 96:500–508, describe a B.t. isolate named *Bacillus thuringiensis* var. tenebrionis, which is reportedly active against two beetles in the order Coleoptera. These are the Colorado potato beetle, *Leptinotarsa decemlineata*, and *Agelastica alni*. In European Patent Application No. 0 202 739 there is disclosed a novel B.t. isolate active against Coleoptera. It is known as *B. thuringiensis* var. san diego (B.t.s.d.). U.S. Pat. No. 4,966,765 discloses the coleopteran-active *Bacillus thuringiensis* isolate B.t. PS86B1.

Ants comprise a large group of insects (family Formicidac) from the taxonomic order, Hymenoptera. They are among the most common house pests. In many situations, ants are a nuisance pest. Foraging ants create problems with hygiene in hospitals and the food industry. Ants also create problems in agriculture. Damage can be caused by direct feeding on plants. Harvester and fire ants are commonly associated with this type of damage (Holldobler, B., E. O. Wilson [1990] *The Ants*, Belkap Press, Cambridge, Mass. 732 pp.) Some ants cause indirect damage by nurturing and protecting sap feeding insects such as mealybugs and aphids. Ants, particularly in the genus Solenopsis are capable of producing extremely painful stings to humans. It has been estimated that approximately 10,000 stings occur each year (Habermehl, G. G. [1981] *Venomous Animals and Their Toxins*, Springer-Verlag, N.Y., 195 pp.). The pharaoh ant (*Monomodum pharaonis*) is primarily an urban pest. However, this species can also be an agricultural pest and damage to corn has been noted (Ebeling, W. [1978] *Urban Entomology*, UC Press, Berkeley, Calif., 695 pp.).

Carpenter ants, Camponotus spp., are distributed throughout North America. Some of the more common and/or studied species include *C. toodoe* in the Pacific northwest, *C. clarithorax* in southern California, and the black, red, and Florida carpenter ants, *C. pennsylvanicus, C. noveboracensis* and *C. abdominalis*, respectively, in the east (Ebeling, W. [1978] *Urban Entomology*, Univ. Calif.: Berkeley p. 209–213). Public concern over carpenter ants has been increasing due to the greater probability of structural infestations as suburban developments extend into the forest habitats of the ants.

Pestiferous species of carpenter ants may be considered nuisance pests because of their foraging activity inside homes. More significant damage occurs when carpenter ants extend their nests into sound wood. Nesting sites may be located in live and dead trees, sometimes resulting in damage to shade trees. Nests may also be established in walls and support beams of structures, or in voids within doors, walls, and furniture. Preference for moist or decaying wood has been reported, but nesting sites are not restricted to such areas. Carpenter ant populations develop relatively slowly with colonies of 300–2,000 workers being produced over a 2-year or longer period for various species. The presence of reproductives follows this slow development since their production has been reported only from well established colonies (Hansen, L. D., R. D. Akre [1985] Biology of carpenter ants in Washington state (Hymenoptera: Formicidae: Camponotus). Melanderia 43. 62 p.; Pricer, J. L. [1908] Biol. Bull. 14:177–218). Despite the slow colony growth, large colonies with satellite colonies have been found. Worker movement occurs between the main colony and the satellites, which serve as areas for further brood development and colony expansion (Hansen and Akre [1985], supra).

Current methods for controlling structural infestations of carpenter ants include sanitation of potential and current nest sites, minimizing access to structures (eg. preventing the contact of tree branches with a structure), and the application of insecticides to repel (perimeter spray barriers) and/or eliminate carpenter ants. The use of boric acid dust in dry, wall voids is reported to be effective for up to 20 years (Hansen and Akre, supra).

Recommendations for the chemical control of established structural infestations in the home are often accompanied with warnings of possible hazards to the applicator as well as children and pets. Alternative control methods such as effective biological control agents have not been found (Akre, R. D., L. D. Hansen, A. L. Antonelli [1989] Ext. Bull. Washington State Univ. Coop. Ext. Serv. 1989 rev. no. EB 0818, 6 pp.).

A need clearly exists for a safe, effective biological control agent for carpenter ants.

Pharaoh ants, *Monomorium pharaonis*, have been described as "... the most persistent and difficult of all our house-infesting ants to control or eradicate" (Smith, M. R. [1965] USDA-ARS Tech. Bull. No. 1326, 105 pp.). It is a tropical species which has extended its range to more temperate regions by establishing colonies in heated buildings. Pharaoh ants frequently infests buildings where food is prepared, and have been found to carry pathogenic organisms (Beatson, S. H. [1972] Lancet 1:425–427).

The difficulty in controlling pharaoh ants may be attributed to their inaccessible nesting sites, rapid population growth, and dispersion of colonies. Their small size allows establishment of colonies in any suitable location, including unusual places such as between books and in stored clothing. With multiple queen colonies, and the warm (30° C.), humid (63–80% RH) conditions that favor pharaoh ants, large colonies can develop rapidly. Portions of these large colonies may disperse to form new colonies at any time, probably in response to overcrowding and unfavorable microenvironmental conditions. Unlike other ant species, pharaoh ants do not exhibit intercolony aggression. This permits the adoption of ants from other colonies and may further enhance the establishment of new colonies and reinfestations. Pharaoh ants also forage for food more than 35 m from the nest without distinct trail following, and thus make nests difficult to find and eradicate.

Control methods for pharaoh ants emphasize the use of insect growth regulators (IGR) or toxicants incorporated into baits. Properly implemented bait programs are effective, however it may take over a month to achieve control. Insecticide applications, while fast acting, usually do not eliminate colonies, and may be unacceptable in certain areas where toxic residues are a concern. In addition, insecticide applications are generally not compatible with bait programs.

A need exists for safe and effective biological control agents for pharaoh ants.

BRIEF SUMMARY OF THE INVENTION

The subject invention concerns novel *Bacillus thuringiensis* (B.t.) isolates and genes therefrom which encode novel hymenopteran-active proteins. The novel B.t. isolates, known herein as *Bacillus thuringiensis* PS140E2 (B.t. PS140E2), *Bacillus thuringiensis* PS86Q3 (B.t. PS86Q3) and *Bacillus thuringiensis* PS211B2 (B.t. PS211B2) have been shown to be active against, for example, the pharaoh ant (*Monornorium pharaonis*). Toxins of the subject invention control, for example, fire ants, carpenter ants, argentine ants, and pharaoh ants.

The subject invention also includes mutants of the above isolates which have substantially the same pesticidal properties as the parent isolate. Procedures for making mutants are well known in the microbiological art. Ultraviolet light and nitrosoguanidine are used extensively toward this end.

The subject invention also concerns novel toxins active against ants. A further aspect of the invention concerns genes coding for these formicidal toxins. The subject invention provides the person skilled in this art with a vast array of formicidal toxins, methods for using these toxins, and genes that code for the toxins. The genes or gene fragments of the invention encode *Bacillus thuringiensis* δ-endotoxins which have formicidal activity. The genes or gene fragments can be transferred to suitable hosts via a recombinant DNA vector.

One aspect of the invention is the discovery of a generalized chemical formula common to a wide range of formicidal toxins. This formula can be used by those skilled in this art to obtain and identify a wide variety of toxins having the desired formicidal activity. The subject invention concerns other teachings which enable the skilled practitioner to identify and isolate ant-active toxins and the genes which code therefor. For example, characteristic features of ant-active toxin crystals are disclosed herein. Furthermore, characteristic levels of amino acid homology can be used to characterize the toxins of the subject invention. Yet another characterizing feature pertains to immunoreactivity with certain antibodies. Also, nucleotide probes specific for genes encoding toxins with formicidal activity are described. Thus, the identification of toxins of the subject invention can be accomplished by sequencespecific motifs, overall sequence similarity, immunoreactivity, and ability to hybridize with specific probes.

In addition to the teachings of the subject invention which broadly define B.t. toxins with advantageous formicidal activity, a further aspect of the subject invention is the provision of specific formicidal toxins and the nucleotide sequences which code for these toxins. One such toxin is the gene expression product of isolate PS86Q3.

BRIEF DESCRIPTION OF THE DRAWINGS

Figure 2:
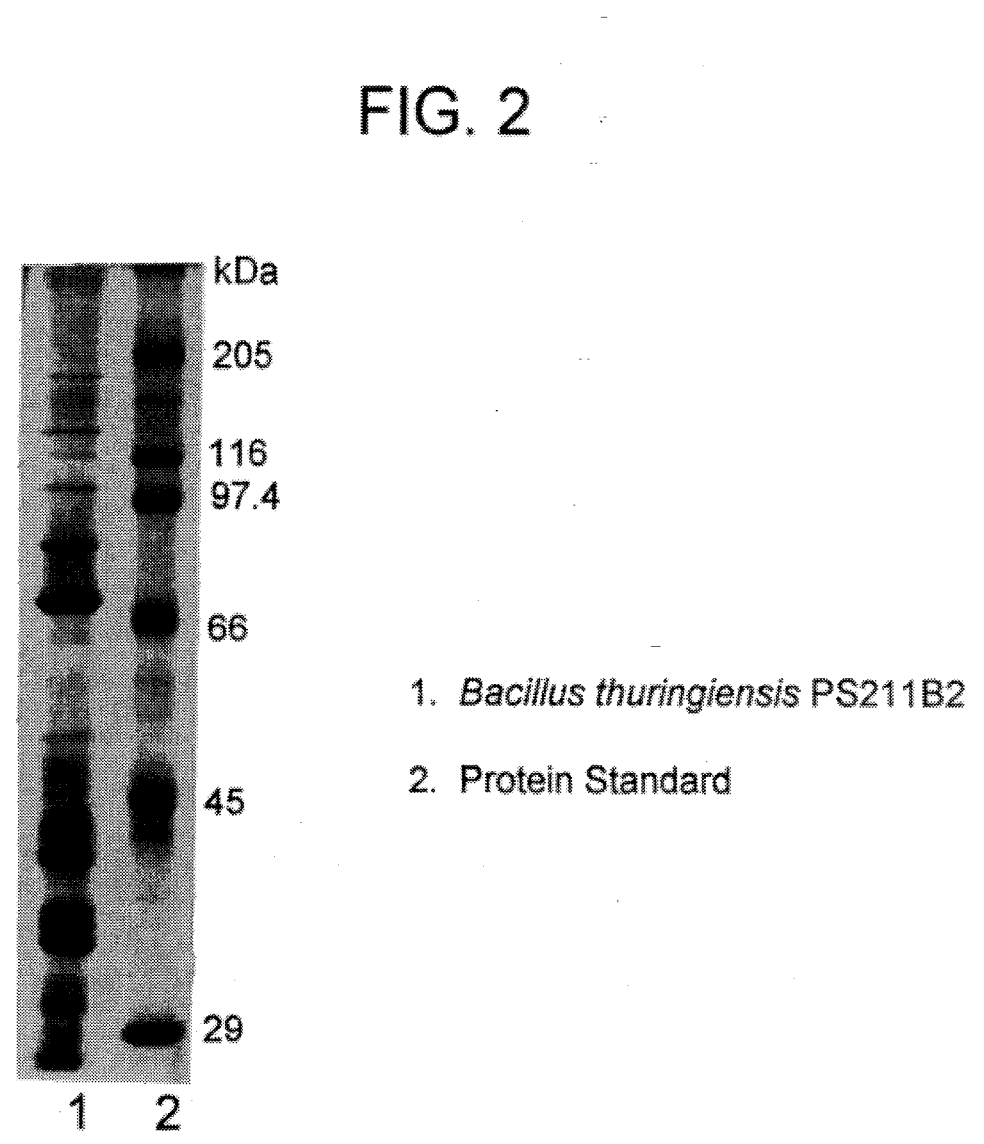

FIG. 2 is a photograph of a standard SDS polyacrylamide gel showing alkali-soluble proteins of B.t. PS211B2 compared to a protein standard.

FIG. 4 is B.t. PS86Q3; and FIG. 5 is B.t. PS211B2). Cells were embedded in an epoxy resin and stained with uranyl acetate and lead citrate.

BRIEF DESCRIPTION OF THE SEQUENCES

Figure 1:
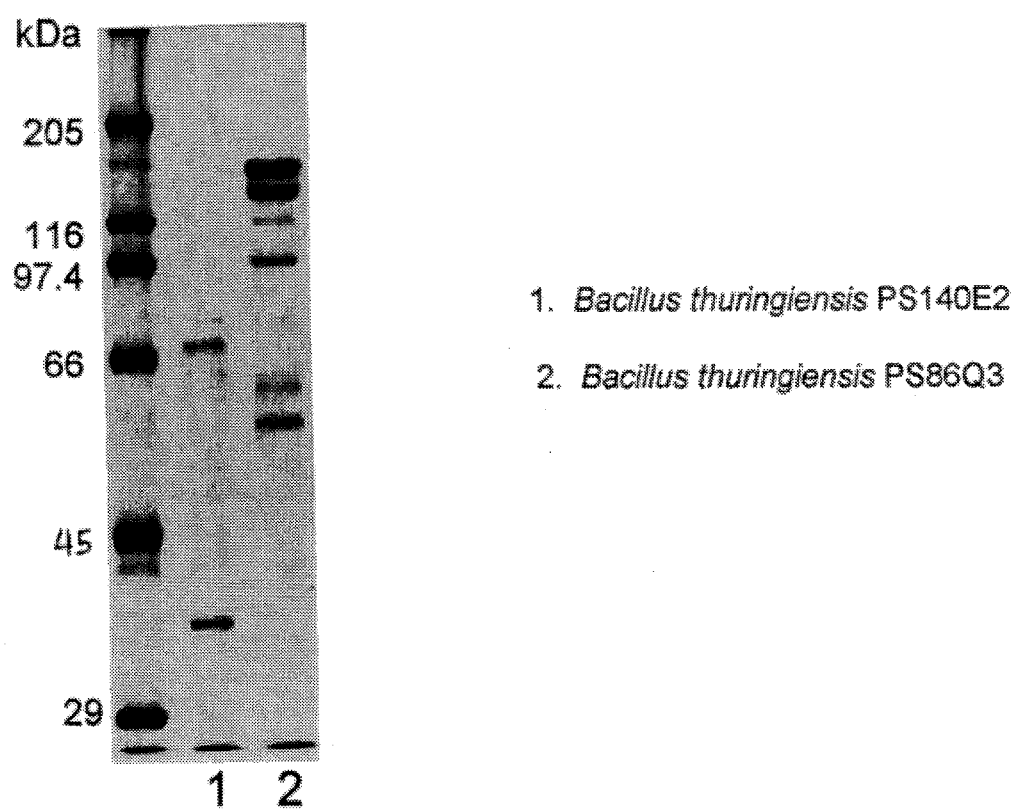
FIG. 1 is a photograph of a standard SDS polyacrylamide gel of B.t. PS140E2, arid B.t. PS86Q3.

SEQ ID NO. 1 is the nucleotide sequence of gene 17a.

SEQ ID NO. 2 is the amino acid sequence of protein 17a.

SEQ ID NO. 3 is the nucleotide sequence of gene 17b.

SEQ ID NO. 4 is the amino acid sequence of protein 17b.

SEQ ID NO. 5 is the nucleotide sequence of gene 33F2.

SEQ ID NO. 6 is the amino acid sequence of protein 33F2.

SEQ ID NO. 7 is the nucleotide sequence of gene 86Q3(a).

SEQ ID NO. 8 is the amino acid sequence of protein 86Q3(a).

SEQ ID NO. 9 is the nucleotide sequence of gene 63B.

SEQ ID NO. 10 is the amino acid sequence of protein 63B.

SEQ ID NO. 11 is the amino acid sequence of a probe which can be used according to the subject invention.

SEQ ID NO. 12 is DNA coding for the amino acid sequence of SEQ ID NO. 11.

SEQ ID NO. 13 is DNA coding for the amino acid sequence of SEQ ID NO. 11.

SEQ ID NO. 14 is the amino acid sequence of a probe which can be used according to the subject invention.

SEQ ID NO. 15 is DNA coding for the amino acid sequence of SEQ ID NO. 14.

SEQ ID NO. 16 is DNA coding for the amino acid sequence of SEQ ID NO. 14.

SEQ ID NO. 17 is the N-terminal amino acid sequence of 17a.

SEQ ID NO. 18 is the N-terminal amino acid sequence of 17b.

SEQ ID NO. 19 is the N-terminal amino acid sequence of 86Q3(a).

SEQ ID NO. 20 is the N-terminal amino acid sequence of 63B.

SEQ ID NO. 21 is the N-terminal amino acid sequence of 33F2.

SEQ ID NO. 22 is an internal amino acid sequence for 63B.

SEQ ID NO. 23 is a synthetic oligonucleotide derived from 17.

SEQ ID NO. 24 is the forward oligonucleotide primer from 63B.

SEQ ID NO. 25 is the reverse oligonucleotide primer from 63B.

SEQ ID NO. 26 is oligonucleotide probe 33F2A.

SEQ ID NO. 27 is oligonucleotide probe 33F2B.

SEQ ID NO. 28 is a reverse primer used according to the subject invention.

SEQ ID NO. 29 is an oligonucleotide derived from the N-terminal amino acid sequence of 86Q3(a) (SEQ ID NO. 19).

SEQ ID NO. 30 is the amino acid sequence coded for by an oligonucleotide used according to the subject invention (SEQ ID NO. 31).

SEQ ID NO. 31 is an oligonucleotide which codes for the amino acid sequence of SEQ ID NO. 30.

SEQ ID NO. 32 is the amino acid sequence coded for by the oligonucleotide of SEQ ID NO. 33.

SEQ ID NO. 33 is a DNA sequence coding for the peptide of SEQ ID NO. 32.

SEQ ID NO. 34 is the reverse complement primer to SEQ ID NO. 38, used according to the subject invention.

SEQ ID NO. 35 is a forward primer according to the subject invention.

SEQ ID NO. 36 is an amino acid sequence according to the subject invention.

SEQ ID NO. 37 is a reverse primer according to the subject invention.

SEQ ID NO. 38 is the nematode (NEMI) variant of region 5 of Höfte and Whiteley.

SEQ ID NO. 39 is the Generic Formula according to the subject invention.

DETAILED DISCLOSURE OF THE INVENTION

One aspect of the subject invention is the discovery of *Bacillus thudngiensis* isolates having activity against ants. The novel *Bacillus thuringiensis* isolates of the subject invention have the following characteristics in their biologically pure form:

Characteristics of B.t. PS140E2

Colony morphology—large colony, dull surface, typical B.t.

Vegetative cell morphology—typical B.t.

Culture methods—typical for B.t.

Inclusions—an elliptical coated inclusion outside the exosporium, and a long inclusion inside the exosporium Approximate molecular weight of alkali/SDS-soluble polypeptides (kDa)—78, 70, 35

Serotype—6, entomocidus.

Characteristics of B.t. pS86Q3

Colony morphology—large colony, dull surface, typical B.t.

Vegetative cell morphology—typical B.t.

Culture methods—typical for B.t.

Inclusions—long areorphic inclusion and a small inclusion, both of which remain with the spore after lysis Approximate molecular weight of alkali/SDS-soluble polypeptides (kDa)—155, 135, 98, 62, 58

Serotype—new serotype (not H-1 through H-27).

Characteristics of B.t. PS211B2

Colony morphology—large colony, dull surface, typical B.t.

Vegetative cell morphology—typical B.t.

Culture methods—typical for B.t.

Inclusions—large round amorphic inclusion with coat, and elliptical inclusion

Approximate molecular weight of alkali/SDS-soluble polypeptides (kDa)—175, 130, 100, 83, 69, 43, 40, 36, 35, 34 and 27

Serotype—6, entomocidus.

A comparison of the characteristics of *B. thuringiensis* PS140E2 (B.t. PS140E2), *B. thuringiensis* PS86Q3 (B.t. PS86Q3), *B. thuringiensis* PS211B2 (B.t. PS211B2), *B. thuringiensis* var. san diego (B.t.s.d.), and *B. thuringiensis* var. kurstaki (HD-1) is shown in Table 1.

TABLE 1

| | Comparison of *B.t.* PS140E2, *B.t.* PS86Q3, *B.t.* PS211B2, *B.t.s.d.*, and *B.t.* HD-1 | | | | |
|---|---|---|---|---|---|
| Inclusions: | *B.t.* PS140E2 Ellipse and 2 small inclusions | *B.t.* PS86Q3 1 long and 1 or 2 small inclusions | *B.t.* PS211B2 Large amorphic | *B.t.* HD-1 Bipyramid | *B.t.s.d.* Flat square |
| Approximate molecular wt. of proteins by SDS-PAGE | 78,000<br>70,000<br>35,000 | 155,000<br>135,000<br>98,000<br>62,000<br>58,000 | 175,000<br>130,000<br>100,000<br>83,000<br>69,000<br>43,000<br>40,000<br>36,000<br>35,000<br>34,000<br>27,000 | 130,000<br>68,000 | 72,000<br>64,000 |
| Host range | Hymenoptera | Hymenoptera | Hymenoptera | Lepidopteran and Coleopteran | Coleoptera (Colorado Potato Beetle |

In addition to the ant-active B.t. isolates described herein, the subject invention concerns a vast array of B.t. δ-endotoxins having formicidal activity. In addition to having formicidal activity, the toxins of the subject invention will have one or more of the following characteristics:

1. An amino acid sequence according to the generic formula disclosed herein.
2. A high degree of amino acid homology with specific toxins disclosed herein.
3. A DNA sequence encoding the toxin wherein said sequence hybridizes with probes or genes disclosed herein.
4. A nucleotide sequence which can be amplified using primers disclosed herein.
5. A crystal toxin presentation as described herein.
6. Immunoreactivity to an antibody raised to a toxin disclosed herein.

One aspect of the subject invention concerns the discovery of a generic chemical formula (hereinafter referred to as the Generic Formula) which can be used to identify toxins having activity against ants. This formula describes toxin proteins having molecular weights in excess of 130,000 kDa. The Generic Formula below covers those amino acids in the N-terminal region extending two amino acids past the invariant proline residue encountered at amino acid number 695 in the sequence of 86Q3(a). The organization of the toxins within this class is delineated by the following generic sequence motif (SEQ ID NO: 39) that is the ultimate determinant of structure and function.

Formicidal toxins according to the Generic Formula (SEQ ID NO. 39) of the subject invention are specifically exemplified herein by the toxin encoded by the gene designated 86Q3(a). Since this toxin is merely exemplary of the toxins represented by the Generic Formula (SEQ ID NO. 39) presented herein, it should be readily apparent that the subject invention further comprises equivalent toms (and nucleotide sequences coding for equivalent toxins) having the same or similar biological activity of 86Q3(a). These equivalent toxins will have amino acid homology with 86Q3(a). This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

| | | | | | |
|---|---|---|---|---|---|
| 1 | MOXLUEBYPx | BXYUBLXxxx | xxxxXXXXXX | XXXXXBXXxX | EXXXKXXXKX |
| | XxxxxxXJXX | XXBXXXXXXX | XXLXXXXXXX | XXLZBLZBxB | PXXXXXXXXX |
| 101 | XXBBXXBXXX | XXXXXXXXKX | XXLBXXBXXX | BXXBBXXXBX | XXXXXXXUXX |
| | BXZLUXXXXX | XXXOBXXXX* | XXXXxxxxxx | xxxxxxxxxX | XX*xxxxxxx |
| 201 | xxxxxXXUZX | XOXXLXXBxx | xxxxxxxXXE | XXXXXxxxXL | PXYOXBOXXH |
| | LBLXJXXLxx | xxxxxXKXXB | XXJXxBXXXK | XXLXXXLXXX | XLOBXXXBXX |
| 301 | XLXXXxXXXJ | xXZXXXXXXY | BJXBOXX*LE | BXXXXPOBEX | XXYXXxxxxx |
| | XLXXOKXLXZ | XxxxxxXXXX | BXXXXXZXXX | ZXXXXXXxXX | XXXBXXXXXX |
| 401 | XXXXBxxxxx | xxxxXXXXXX | LXXXXXXXXX | XXX*xxXXXX | Xxxxxxxxxx |
| | XXXXXXXXXX | XXXUX*XXXX | XXPLXXX*XJ | XxXXXXXXXX | XXXXXBxXXX |
| 501 | XXZXXxxxxx | xx*x*XXXXX | XXXXXXXxxx | XXXXXXXLXX | LYXXXXXXXJ |
| | XXXxXBXxBB | ZXXXXXEXXX | XXBXZXXXXX | XXBXXXXBXx | xxXXKxxxxx |
| 601 | XxxxxxxxxE | XLUZXUXBXL | XXXUXBXBXB | XXXXXXXYXL | K*KUPZXXXX |
| | XXXBXBEXXX | xUXBXXXXXX | XZXXXXXXXx | XXXXXXYXBX | ZXOxxxxxxX |
| 701 | xXLXxxxxxx | xxxXUXXXXB | BLEKLEBBPX | X | |

Numbering is for convenience and approximate location only.
Symbols used:

A = ala    G = gly    M = met    S = ser
C = cys    H = his    N = asn    T = thr
D = asp    I = ile    P = pro    V = val
E = glu    K = lys    Q = gln    W = trp
F = phe    L = leu    R = arg    Y = tyr
K = K or R
E = E or D
L = L or I
B = M, L I, V, or F
J = K, R, E, or D
O = A or T
U = N or Q
Z = G or S
X = any naturally occurring amino acid, except C.
*= any naturally occurring amino acid.
x = any naturally occurring amino acid, except C
   (or complete omission of any amino acids).

Where a stretch of wild-card amino acids are encountered (X(n) or x(n) where n>2), repetition of a given amino acid should be avoided. Similarly, P, C, E, D, K, or R utilization should be minimized.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. The information presented in the generic formulae of the subject invention provides clear guidance to the person skilled in this an in making various amino acid substitutions.

Further guidance for characterizing the formicidal toxins of the subject invention is provided in Tables 4 and 5, which demonstrate the relatedness among toxins within the formicidal toxins. These tables show a numeric score for the best matching alignment between two proteins that reflects: (1) positive scores for exact matches, (2) positive or negative scores reflecting the likelihood (or not) of one amino acid substituting for another in a related protein, and (3) negative scores for the introduction of gaps. A protein sequence aligned to itself will have the highest possible score—i.e., all exact matches and no gaps. However, an unrelated protein or a randomly generated sequence will typically have a low positive score. Related sequences have scores between the random background score and the perfect match score.

The sequence comparisons were made using the local homology algorithm of Smith and Waterman ([1981] *Advances in Applied Mathematics* 2:482–489), implemented as the program "Bestfit" in the GCG Sequence Analysis Software Package Version 7 April 1991. The sequences were compared with default parameter values (comparison table: Swgappep. Cmp, Gap weight:3.0, Length weight:0.1) except that gap limits of 250 residues were applied to each sequence compared. The program output value compared is referred to as the Quality score.

Tables 4 and 5 show the pairwise alignments between the indicated amino acids of the ant-active proteins and representatives of dipteran (CryIV; ISRH3 of Sen, K. et al. [1988] *Agric. Biol. Chem.* 52:873–878), lepidopteran and dipteran (CryIIA; CryB1 of Widner and Whiteley [1989] *J. Bacteriol.* 171:965–974), and lepidopteran (CryIA(c); Adang et al. [1981] *Gene* 36:289–300) proteins.

Table 3 shows which amino acids were compared from the proteins of interest.

TABLE 3

| Protein | Amino acids compared |
| --- | --- |
| 86Q3(a) | 1-697 |
| 63B | 1-692 |
| 33F2 | 1-618 |
| 17a | 1-677 |
| 17b | 1-678 |
| CryIV | 1-633 |
| CryIIA | 1-633 |
| CryIA(c) | 1-609 |

Table 4 shows the scores prior to adjustment for rrandom sequence scores.

TABLE 4

| | 86Q3(a) | 63B | 33F2 | 17b | 17a | CryIVA | CryIIA | CryIA(c) |
| --- | --- | --- | --- | --- | --- | --- | --- | --- |
| 86Q3(a) | 1046 | 389 | 310 | 342 | 340 | 236 | 237 | 238 |
| 63B | | 1038 | 274 | 339 | 338 | 235 | 228 | 232 |
| 33F2 | | | 927 | 323 | 322 | 251 | 232 | 251 |
| 17b | | | | 1017 | 1007 | 238 | 240 | 236 |
| 17a | | | | | 1016 | 240 | 240 | 237 |
| CryIVA | | | | | | 950 | 245 | 325 |
| CryIIA | | | | | | | 950 | 244 |
| CryIA(c) | | | | | | | | 914 |

Note that ant-active protein 86Q3(a) is more closely related to 63B, 17a, 17b, and 33F2 than it is to the CryIVA, CryIIA, and CryIA(c) toxins.

Table 5 shows the same analysis after subtraction of the average score of 50 alignments of random shuffles of the column sequences with the row sequences.

TABLE 5

| | 86Q3(a) | 63B | 33F2 | 17b | 17a | CryIVA | CryIIA | CryIA(c) |
| --- | --- | --- | --- | --- | --- | --- | --- | --- |
| 86Q3(a) | 841 | 184 | 118 | 136 | 135 | 41 | 40 | 50 |
| 63B | | 831 | 81 | 133 | 130 | 40 | 33 | 43 |
| 33F2 | | | 740 | 130 | 128 | 65 | 50 | 71 |
| 17b | | | | 811 | 798 | 42 | 44 | 47 |
| 17a | | | | | 808 | 43 | 44 | 44 |
| CryIVA | | | | | | 761 | 54 | 141 |
| CryIIA | | | | | | | 755 | 55 |
| CryIA(c) | | | | | | | | 729 |

Note that in Table 5 the same relationships hold as in Table 4, i.e., 86Q3(a)'s highest score, aside from itself, is with 63B.

This degree of relatedness provides the basis for using common or similar sequence elements from the previously-described known genes to obtain related, but non-identical genes from an ant-active isolate.

Thus, certain toxins according to the subject invention can be defined as those which have formicidal activity and have an alignment value (according to the procedures of Table 5) greater than 100 with 86Q3(a). As used herein, the term "alignment value" refers to the scores obtained using the methods described above which were used to create the scores reported in Table 5.

Figure 3:
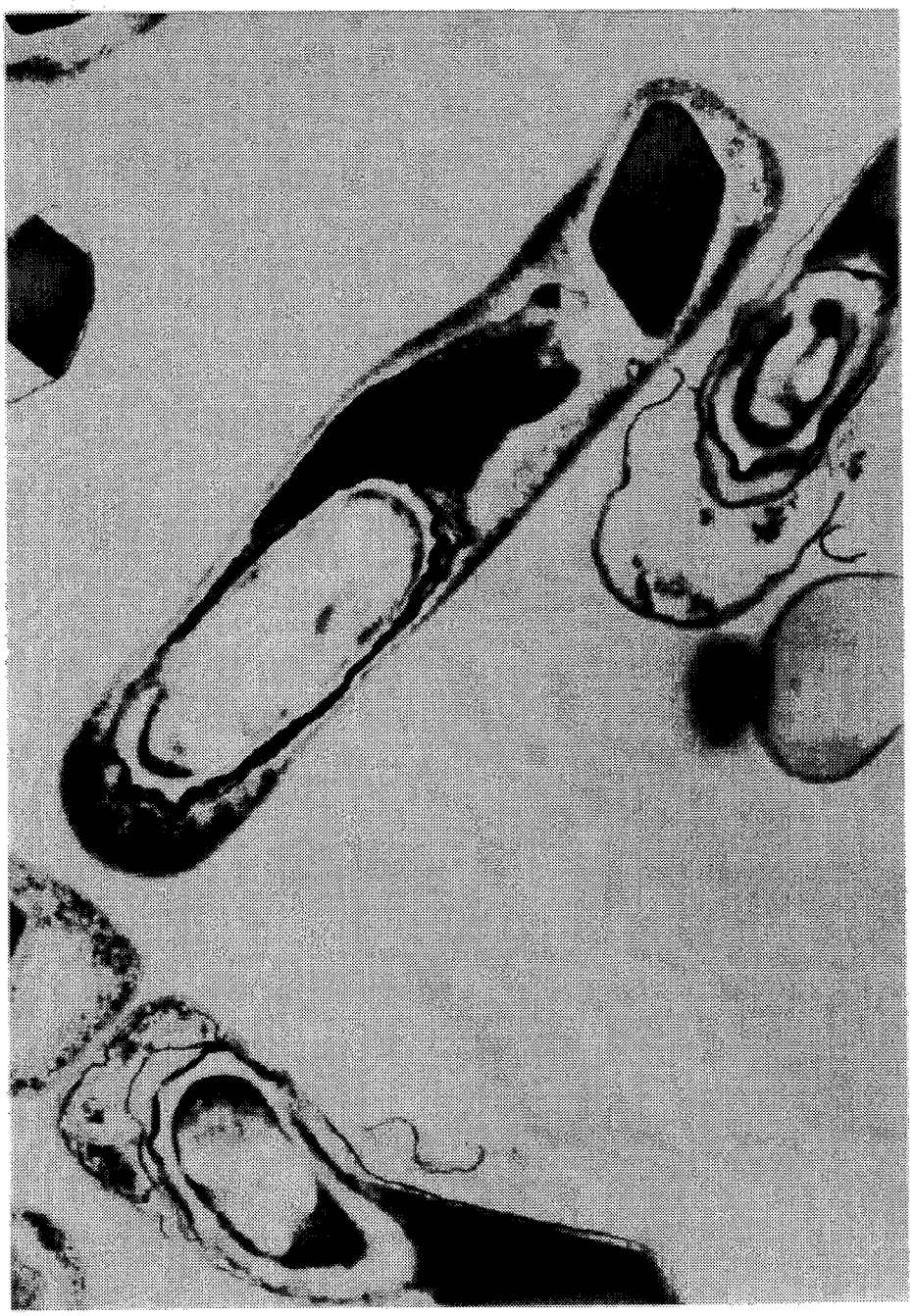
FIGS. 3–5 are transmission electron micrographs of ultrathin sections of the ant-active B.t. strains (FIG. 3 is B.t. PS14E2.

The toxins of the subject invention can also be characterized in terms of the shape and location of toxin inclusions. Inclusion type PS86Q3—Long amorphic inclusion and a small inclusion, both of which remain with the spore after lysis. See FIG. 3.

Figure 4:

PS140E2—An elliptical coated inclusion situated outside the exosporium, and a long inclusion inside the exosporium. See FIG. 4.

Figure 5:

PS211B2—Large round amorphic inclusion with coat, and an elliptical inclusion. See FIG. 5.

The genes and toxins according to the subject invention include not only the full length sequences disclosed herein but also fragments of these sequences, or fusion proteins, which retain the characteristic formicidal activity of the sequences specifically exemplified herein.

It should be apparent to a person skilled in this art that genes coding for antactive toxins can be identified and obtained through several means. The specific genes may be obtained from a culture depository as described below. These genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal13 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be located from B.t. isolates and/or DNA libraries using the teachings provided herein. There are a number of methods for obtaining the ant-active toxins of the instant invention which occur in nature. For example, antibodies to the ant-active toxins disclosed and claimed herein can be used to identify and isolate other toxins from a mixture of proteins. Specifically, antibodies may be raised to the portions of the antactive toxins which are most constant and most distinct from other B.t. toxins. These antibodies can then be used to specifically identify equivalent toxins with the characteristic formicidal activity by immunoprecipitation, enzyme linked immunoassay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying formicidal endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed test sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful, according to the subject invention, in the rapid identification of ant-active genes are (i) DNA coding for a peptide sequence whose single letter amino acid designation is "REWINGAN" ( SEQ ID NO. 11) or variations thereof which embody point mutations according to the following: position 1, R or K; position 3, W or Y; position 4, I or L; position 7, A or N; position 8, N or Q; a specific example of such a probe is "AGA(A or G)T(G or A)(G or T)(A or T)T(A or T)AATGG(A or T)GC(G or T)(A or C)A" (SEQ ID NO. 12); another example of such a probe is "GA(A or G)TGG(A or T)TAAATGGT(A or G)(A or C)(G or C)AA" (SEQ ID NO. 13);

(ii) DNA coding for a peptide sequence whose single letter amino acid designation is "PTFDPDLY" (SEQ ID NO. 14) or variations thereof which embody point mutations according to the following: position 3, F or L; position 4, D or Y; position 5, P or T; position 6, D or H; position 7, L or H or D or N; a specific example of such a probe is "CC(A or T)AC(C or T)TIT(T or G)ATCCAGAT(C or G)(T or A)(T or C)TAT" (SEQ ID NO. 15); another example of such a probe is "CC(T or A)AC(T or A)TT(T or C)GAT(C or A)CA(G or C)AT(C or A)(T or A)TTAT" (SEQ ID NO. 16);

(iii) additional useful probes for detecting ant-active B.t. genes include "GCAATTTTAA ATGAATTATA TCC" (SEQ ID NO. 23), "CAAYTACAAG CWCAACC" (SEQ ID NO. 24), "AATGAAGTWT ATCCWGTWAA T" (SEQ ID NO. 27), "GCAAGCGGCC GCTFATG-GAA TAAATTCAAT TYKRTCWA" (SEQ ID NO. 28), "AGACTGGATC CATGGCWACW ATWAAT-GAAT TATAYCC" (SEQ ID NO. 29), "TAACGTG-TAT WCGSTTTTAA TTTWGAYTC" (SEQ ID NO. 31), "TGGAATAAAT TCAATTYKRT CWA" (SEQ ID NO. 33), "AGGAACAAAY TCAAKWCGRT CTA" (SEQ ID NO. 34), and "TCTCCATCTT CTGARG-WAAT" (SEQ ID NO. 37).

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the B.t. toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser, E. T., Kezdy, F. J. [1984] *Science* 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such routants may include asporogenous host cells which also can be prepared by procedures well known in the art.

The toxin genes or gene fragments exemplified according to the subject invention can be obtained from *B. thuringiensis* (B.t.) isolates designated PS17, PS33F2, PS63B, and PS86Q3. Subcultures of the *E. coli* host harboring the toxin genes of the invention were deposited in the permanent collection of the Northern Research Laboratory, U.S. Department of Agriculture, Peoria, Ill., U.S.A. The accession numbers are as follows:

| Culture | Repository No. | Deposit Date |
| --- | --- | --- |
| B.t. PS140E2 | NRRL B-18812 | April 23, 1991 |
| B.t. PS86Q3 | NRRL B-18765 | February 6, 1991 |
| B.t. PS211B2 | NRRL B-18921 | November 15, 1991 |
| B.t. PS17 | NRRL B-18243 | July 28, 1987 |
| B.t. PS33F2 | NRRL B-18244 | July 28, 1987 |
| B.t. PS63B | NRRL B-18246 | July 28, 1987 |
| E. coli NM522 (pMYC2316)(33F2) | NRRL B-18785 | March 15, 1991 |
| E. coli NM522 (pMYC2321) | NRRL B-18770 | February 14, 1991 |
| E. coli NM522 (pMYC2317) | NRRL B-18816 | April 24, 1991 |
| E. coli NM522 (pMYC1627)(17a) | NRRL B-18651 | May 11, 1990 |
| E. coli NM522 (pMYC1628)(17b) | NRRL B-18652 | May 11, 1990 |
| E. coli NM522 (pMYC1642)(63B) | NRRL B-18961 | April 10, 1992 |
| E. coli MR618 (pMYC1647)(86Q3) | NRRL B-18970 | April 29, 1992 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The B.t. isolates of the invention can be cultured using standard art media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, liquid concentrate, granules, or other formulations by the addition of suffactants, dispersants, inert carriers and other components to facilitate handling and application for particular target pests. These formulation and application procedures are all well known in the art.

Formulated products can be sprayed or applied as baits to control hymenopteran pests. When applied with a bait, the B.t. itself may be used, or another suitable host, as described herein, may be transformed with a B.t. gene and used to express toxins. A vegetable oil or other liquid substance can be added to a bait to make it more attractive to the pests. Various attractants, including pheromone compounds, are well known to those skilled in the art and can be used as a component of the bait. The bait and toxin or toxin-producing microbe can be used as part of a trap.

The B.t. cells of the invention can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., *Animal Tissue Techniques*, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, fleezing, UV irradiation, lyophilization, and the like.

Genes encoding toxins having activity against the target susceptible pests can be isolated from the B.t. isolate of the invention by use of well known procedures.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of hymenopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobactedum tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al. (1982) *J. Bactetiol.* 150:6069; Bagdasarian et al. (1981) *Gene* 16:237; and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibdo, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans,* and the like.

The cell will usually be intact and be substantially in the proliferative form when treated, rather than in a spore form, although in some instances spores may be employed.

Treatment of the recombinant microbial cell can be done as disclosed infra. The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, baits, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95 % by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the hymenopteran pest(s), e.g., plants, soil or water, by spraying, dusting, sprinkling, baits or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates of the Invention

A subculture of a B.t. isolate can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salts Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

EXAMPLE 2

Purification of Protein and Amino Acid Sequencing

The B.t. isolates PS86Q3, PS17, PS63B, and PS33F2 were cultured as described in Example 1. The parasporal inclusion bodies were partially purified by sodium bromide (28–38%) isopycnic gradient centrifugation (Pfannenstiel, M. A., E. J. Ross, V. C. Kramer, K. W. Nickerson [1984] FEMS *Microbid. Lett.* 21:39). The proteins were bound to PVDF membranes (Millipore, Bedford, Mass.) by western blotting techniques (Towbin, H., T. Staehlelin, K. Gordon [1979] *Proc. Natl. Acad. Sci. USA* 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] *Meth. Enzymol.* 91:399). The sequences obtained were:

17a: A I L N E L Y P S V P Y N V (SEQ ID NO. 17)

17b: A I L N E L Y P S V P Y N V (SEQ ID NO. 18)

86Q3(a): M A T I N E L Y P N V P Y N V L (SEQ ID NO. 19)

63B: Q L Q A Q P L I P Y N V L A (SEQ ID NO. 20)

33F2: A T L N E V Y P V N (SEQ ID NO. 21)

In addition, internal amino acid sequence data were derived for 63B. The toxin protein was partially digested with *Staphylococcus aureus* V8 protease (Sigma Chem. Co., St. Louis, Mo.) essentially as described (Cleveland, D. W., S. C. Fischer, M. W. Kirschner, U. K. Laemmli [1977] *J. Biol. Chem.* 252:1102). The digested material was blotted onto PVDF membrane and a ca. 28 kDa limit peptide was selected for N-terminal sequencing as described above. The sequence obtained was:

63B(2) V Q R I L D E K L S F Q L I K (SEQ ID NO. 22)

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from formicidal B.t. isolates. RFLP analysis of restricted total cellular DNA using radiolabeled oligonucleotide probes has elucidated different genes or gene fragments.

EXAMPLE 3

Cloning of Novel Toxin Genes and Transformation into *Escherichia coli*

Total cellular DNA was prepared by growing the cells B.t. PS17 to a low optical density ($OD_{600}$=1.0) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCl, 20 mM NaOAc, 2.5 mM EDTA, pH=8.0) buffered gel. A Southern blot of the gel was hybridized with a [$^{32}$P]-radiolabeled oligonucleotide probe derived from the N-terminal amino acid sequence of purified 130 kDa protein from PS17. The sequence of the oligonucleotide synthesized is (GCAATTTTAAAT-GAATYATATCC) (SEQ ID NO. 23). Results showed that the hybridizing EcoRI fragments of PS17 are 5.0 kb, 4.5 kb, 2.7 kb and 1.8 kb in size, presumptively identifying at least four new ant-active toxin genes, 17d, 17b, 17a and 17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip™ ion exchange column (Schleicher and Schuel, Keene NH). The isolated Sau3A fragments were ligated into LambdaGEM-11™ (PROMEGA). The packaged phage were plated on KW251 *E. coli* cells (PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 *E. coli* cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (17b) or the 2.7 kb (17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to Sa/I-digested and dephosphorylated pBClac, an *E. coli*/B.t. shuttle vector comprised of replication origins from pBC16 and pUC19. The ligation mix was introduced by transformation into NM522 competent *E. coli* cells and plated on LB agar containing ampicillin, isopropyl-(Beta)-D-thiogalactoside(IPTG)and5-Bromo-4-Chloro-3-indolyl-(Beta)-D-galactoside (XGAL). White colonies, with putative insertions in the (Beta)-galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The PS17 toxin genes were subcloned into the shuttle vector pHT3101 (Lereclus, D. et al. [1989] *FEMS Microbiol. Lett.* 60:211–218) using standard methods for expression in B.t. Briefly, SalI fragments containing the 17a and 17b toxin genes were isolated from pMYC1629 and pMYC1627, respectively, by preparative agarose gel electrophoresis, electroelution, and concentrated, as described above. These concentrated fragments were ligated into SalI-cleaved and dephosphorylated pHT3101. The ligation mixtures were used separately to transform frozen, competent *E. coli* NM522. Plasmids from each respective recombinant *E. coli* strain were prepared by alkaline lysis and analyzed by agarose gel electrophoresis. The resulting subclones, pMYC2311 and pMYC2309, harbored the 17a and 17b toxin genes, respectively. These plasmids were transformed into the acrystalliferous B.t. strain, HD-1 cryB (Aronson, A., Purdue University, West Lafayette, Ind.), by standard electroporation techniques (Instruction Manual, Biorad, Richmond, Calif.).

Recombinant B.t. strains HD-1 cryB [pMYC2311] and [pMYC2309] were grown to sporulation and the proteins purified by NaBr gradient centrifugation as described above for the wild-type B.t. proteins.

EXAMPLE 4

Molecular Cloning of a Gene Encoding a Novel Toxin from *Bacillus thudngiensis* Strain PS63B Example 2 shows the aminoterminal and internal polypeptide sequences of the 63B toxin protein as determined by standard Edman protein sequencing. From these sequences, two oligonucleotide primers were designed using a codon frequency table assembled from B.t. genes encoding δ-endotoxins. The sequence of the forward primer (63B-A) was complementary to the predicted DNA sequence at the 5' end of the gene:

63B-A-5' CAA T/CTA CAA GCAfF CAA CC 3' (SEQ ID NO. 24) The sequence of the reverse primer (63B-INT) was complementary to the inverse of the internal predicted DNA sequence:

63B-INT-5' TTC ATC TAA AAT TCT TTG A/TAC 3' (SEQ ID NO. 25) These primers were used in standard polymerase chain reactions (Cetus Corporation) to amplify an approximately 460 bp fragment of the 63B toxin gene for use as a DNA cloning probe. Standard Southern blots of total cellular DNA from 63B were hybridized with the radiolabeled PCR probe. Hybridizing bands included an approximately 4.4 kbp XbaI fragment, an approximately 2.0 kbp HindIII fragment, and an approximately 6.4 kbp SpeI fragment.

Total cellular DNA was prepared from *Bacillus thuringiensis (B.t.) cells grown to an optical density of* 1.0 at 600 nm. The cells were recovered by centrifugation and protoplasts were prepared in lysis mix (300 mM sucrose, 25 mM Tris-HCl, 25 mM EDTA, pH=8.0) and lysozyme at a concentration of 20 mg/ml. The protoplasts were ruptured by addition of ten volumes of 0.1M NaCl, 0.1M Tris-HCl pH 8.0, and 0.1% SDS. The cellular material was quickly frozen at –70° C. and thawed to 37° C. twice. The supernatant was extracted twice with phenol/chloroform (1:1). The nucleic acids were precipitated with ethanol. To remove as much RNA as possible from the DNA preparation, RNase at final concentration of 200 μg/ml was added. After incubation at 37° C. for 1 hour, the solution was extracted once with phenol/chloroform and precipitated with ethanol.

A gene library was constructed from 63B total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, NH). The isolated NdeII fragments were ligated into BamHI-digested LambdaGEM-11 (PROMECA). The packaged phage were plated on *E. coli* KW25 1 cells (PROMECA) at a high titer and screened using the radiolabeled approximately 430 bp fragment probe amplified with the 63B-A and 63B internal primers (SEQ ID NOS. 27 and 28, respectively) by polymerase chain reaction. Hybridizing plaques were purified and rescreened at a lower plaque density. Single isolated, purified plaques that hybridized with the probe were used to infect KW25 1 cells in liquid culture for preparation of phage for DNA isolation. DNA was isolated by standard procedures (Maniatis, T., E. F. Fritsch, J. Sambrook [1982] *Molecular Cloning: A Laboratory Manual*, Cold Spring Harbor Laboratory, New York). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli*/B.t. shuttle vector comprised of pBlueScript S/K [Stratagene, San Diego, Calif.] and the replication origin from a resident B.t. plasmid [Lereclus, D. et al. (1989) *FEMS Microbiol. Lea.* 60:211–218]). The ligation mix was introduced by transformation into competent *E. coli* NM522 cells (ATCC 47000) and plated on LB agar containing ampicillin (100 µg/ml), IPTG (2%), and XGAL (2%). White colonies, with putative restriction fragment insertions in the (Beta)-galactosidase gene of pHTBlueII, were subjected to standard rapid plasmid purification procedures (Maniatis et al., supra). Plasmids ere analyzed by SalI digestion and agarose gel electrophoresis. The desired plasmid construct, pMYC1641, contains an approximately 14 kb SalI insert.

For subcloning, preparative amounts of DNA were digested with XbaI and electrophoresed on an agarose gel. The approximately 4.4 kbp band containing the toxin gene was excised from the gel, electroeluted from the gel slice, and purified by ion exchange chromatography as above. This fragment was ligated into XbaI cut pHTBlueII and the resultant plasmid was designated pMYC1642.

EXAMPLE 5

Cloning of a Novel Toxin Gene From B.t. PS33F2 and Transformation into *Escherichia coli*

Total cellular DNA was prepared from B.t. PS33F2 cells grown to an optical density, at 600 nm, of 1.0. Cells were pelleted by centrifugation and resuspended in protoplast buffer (20 mg/ml lysozyme in 0.3M sucrose, 25 mM Tris-Cl [pH 8.0], 25 mM EDTA). After incubation at 37° C., for 1 hour, protoplasts were lysed by the addition of nine volumes of a solution of 0.1M NaCl, 0.1% SDS, 0.1M Tris-Cl followed by two cycles of fleezing and thawing. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE) and RNase was added to a final concentration of 50 µg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Plasmid DNA was extracted from protoplasts prepared as described above. Protoplasts were lysed by the addition of nine volumes of a solution of 10 mM Tris-Cl, 1 mM EDTA, 0.085 N NaOH, 0.1% SDS, pH=8.0. SDS was added to 1% final concentration to complete lysis. One-half volume of 3M KOAc was then added and the cellular material was precipitated overnight at 4° C. After centrifugation, the DNA was precipitated with ethanol and plasmids were purified by isopycnic centrifugation on cesium chloride-ethidium bromide gradients.

Restriction Fragment Length Polymorphism (RFLP) analyses were performed by standard hybridization of Southern blots of PS33F2 plasmid and total cellular DNA with $^{32}$P-labelled oligonucleotide probes designed to the N-terminal amino acid sequence disclosed in Example 2.

Probe 33F2A: 5' GCAfF ACA/T TTA AAT GAA GTAE TAT 3' (SEQ ID NO. 26)

Probe 33F2B: 5' AAT GAA GTAfF TAT CCA/T GTA/T AAT 3' (SEQ ID NO. 27)

Hybridizing bands included an approximately 5.85 kbp EcoRI fragment. Probe 33F2A and a reverse PCR primer were used to amplify a DNA fragment of approximately 1.8 kbp for use as a hybridization probe for cloning the 33F2 toxin gene. The sequence of the reverse primer was:

5' GCAAGCGGCCGCTTATGGAAAAATTCAATT C/T T/G A/G TC T/A A 3' (SEQ ID NO. 28).

A gene library was constructed from 33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene NH). The EcoRI inserts were ligated into EcoRI-digested pHTBlueII (an *E. coli/B. thuringiensis* shuttle vector comprised of pBluescript S/K [Stratagene] and the replication origin from a resident B.t. plasmid (Lereclus, D. et al. [1989] *FEMS Microbial. Lett.* 60:211–218]). The ligation mixture was transformed into frozen, competent NM522 cells (ATCC 47000). Transformants were plated on LB agar containing ampicillin, isopropyl-(Beta)-D-thiogalactoside (IPTG), and 5-bromo-4-chloro-3-indolyl-(Beta)-D-galactoside (XGAL). Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp Eco4RI insert; the toxin gene residing on this DNA fragment (33F2a) is novel compared to the DNA sequences of other toxin genes encoding formicidal proteins.

Plasmid pMYC2316 was introduced into the acrystalliferous (Cry-) B.t. host, HD-1 CryB (A. Aronson, Purdue University, West Lafayette, Ind.) by electroporation. Expression of an approximately 120–140 kDa crystal protein was verified by SDS-PAGE analysis. Crystals were purified on NaBr gradients (M. A. Pfannenstiel et al. [1984] *FEMS Microbiol. Lett.* 21:39) for determination of toxicity of the cloned gene product to Pratylenchus spp.

EXAMPLE 6

Cloning of a Novel Toxin Gene from B.t. Isolate PS86Q3

Total cellular DNA was prepared from *Bacillus thuringiensis* (B.t.) cells grown to an optical density of 1.0 at 600 nm. The cells were recovered by centrifugation and protoplasts were prepared in lysis mix (300 mM sucrose, 25 mM Tris-HCl, 25 mM EDTA, pH=8.0) containing lysozyme at a concentration of 20 mg/ml. The protoplasts were ruptured by addition of ten volumes of 0.1M NaCl, 0.1% SDS, 0.1M Tris-Cl, pH=8.0. The cleared lysate was quickly frozen at −70° C. and thawed to 37° C. twice. The supernate was extracted twice with phenol:chloroform (1:1). The pellet was resuspended in 10 mM Tris-Cl, 1 mM EDTA, pH=8.0 (TE), and RNase was added to a final concentration of 50 µg/ml. After incubation at 37° C. for one hour, the solution was extracted once with phenol:chloroform (1:1) and then with TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Total cellular DNA from isolate PS86Q3 was used as template for polymerase chain reaction (PCR) analysis according to protocols furnished by Perkin Elmer Cetus. An oligonucleotide derived from the N-terminal amino acid sequence of the toxin protein was used as a 5' primer. The sequence of this oligonucleotide is:

5'-AGACTGGATCCATGGC(A or T)AC(A or T)AT(A or T)AATGAATTATA (T or C)CC-3' (SEQ ID NO. 29).

An oligonucleotide coding for the amino acid sequence "ESKLKPNTRY" (SEQ ID NO. 30) can be used as the reverse 3' primer. The sequence of this oligonucleotide can be: "5'-TAACGTGTAT(A or T)CG(C or G)TTTTAATTT(T or A)GA(C or T)TC-3'" (SEQ ID NO. 31).

The reverse "YIDKIEFIP" (SEQ ID NO. 32) oligonucleotide was also used as a reverse 3' primer in conjunction with the above mentioned 5' primer. The sequence of the reverse primer can be: "5'-TGGAATAAATTCAATF(C or T)(T or G)(A or G)TC(T or A)A-3'" (SEQ ID NO. 33).

Amplification with the 5' primer and SEQ ID NO. 31 generates an approximately 2.3 kbp DNA fragment and an approximately 4.3 kbp DNA fragment. Amplification with the 5' primer and SEQ ID NO. 33 generates an approximate 1.8 kbp DNA fragment and an approximately 3.7 kbp DNA fragment. The approximately 2.3 kbp fragment was radiolabeled with $^{32}P$ and used as a hybridization probe to generate restriction fragment polymorphism (RFLP) patterns and to screen recombinant phage libraries.

A Southern blot of total cellular DNA digested with EcoRV was probed with the radiolabeled 2.3 kbp probe described above. The resultant RFLP includes 9.5 kbp, 6.4 kbp, and 4.5 kbp hybridizing fragments.

A gene library was constructed from PS86Q3 total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, NH). The isolated NdeII fragments were ligated into BamHI-digested LambdaGEM-11 (PROMEGA). The packaged phage were plated on *E. coli* KW25 1 cells (PROMEGA) at a high titer and screened using the radiolabeled probe described above. Hybridizing plaques were purified and rescreened at a lower plaque density. Single isolated, purified plaques that hybridized with the probe were used to infect KW251 cells in liquid culture for preparation of phage for DNA isolation. DNA was isolated by standard Zprocedures (Maniatis et al., supra). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli*/B.t. shuttle vector comprised of pBluescript S/K [Stratagene, San Diego, Calif.] and the replication origin from a resident B.t. plasmid (Lereclus et al. [1989], supra). The ligation mix was introduced by transformation into competent *E. coli* NM522 cells (ATCC 47000) and plated on LB agar containing ampicillin, IPTG, and XGAL. White colonies, with putative restriction fragment insertions in the (Beta)-galactosidase gene of pHT-BlueII, were subjected to standard rapid plasmid purification procedures (Maniatis et al., supra). Plasmid DNA was analyzed by SalI digestion and agarose gel electrophoresis. The desired plasmid construct, pMYC1647, contains an approximately 12 kb SalI insert.

Plasmid pMYC1647 was introduced by electroporation into an acrystalliferous (Cry⁻) B.t., HD-1 CryB (A. I. Aronson, Purdue University) host to yield MR515, a recombinant B.t. clone of 86Q3(a). Expression of an approximately 155 kDa protein was verified by SDS-PAGE. Spores and crystals were removed from broth cultures and were used for determination of toxicity to pharaoh ants.

EXAMPLE 7

Activity of the B.t. Toxin Protein and Gene Product Against Ants

2Broths were tested for the presence of β-exotoxin by a larval house fly bioassay (Campbell, D. P., Dieball, D. E., Bracket, J. M. [1987] "Rapid HPLC assay for the β-exotoxin of *Bacillus thutingiensis*," *J. Agric. Food Chem.* 35:156–158). Only isolates which tested free of β-exotoxin were used in the assays against ants.

A bait was made consisting of 10% *Bacillus thuringiensis* isolates of the invention and Crosse and Blackwell mint apple jelly. Approximately 100 ants were placed in each plastic test chamber replicate with the baits. Control experiments were performed with untreated mint apple jelly. Each test was replicated a minimum of 10 times. Mortality was assessed at 7, 14 and 21 days after introduction of the bait to the ants. Results are shown below:

TABLE 6

Toxicity of *B. thuringienis* Isolates to the Pharaoh Ant (*Monomorium pharaonis*)

| B.t. Isolate | Percent Mortality |
|---|---|
| PS140E2 | 91 |
| PS 86Q3 | 84 |
| Control | 11 |
| PS211B2 | 90.0 |
| Control | 3.8 |

EXAMPLE 8

Activity Against Pharaoh Ants

Mint apple jelly containing 10% B.t. (100,000 ppm) was fed to 5 replicates of approximately 100 worker ants for 21 days. Total mortality (in %) over the test period is compared to control.

TABLE 7

Three week mortality (%) on pharaoh ant workers.

| Sample | Rate ppm | % Mortality |
|---|---|---|
| MR515 | 100000 | 40.1 |
| 86Q3 | 100000 | 29.2 |
| 211B2 | 100000 | 58.5 |
| MAJ | Blank | 25.0 |
| Control | Blank | 14.4 |

MR515 = a recombinant *B.t.* clone of 86Q3(a) gene, 10% in MAJ (Example 6)
86Q3 = spray dried powder of *B.t.* PS86Q3, 10% in MAJ
211B2 = spray dried power of *B.t.* PS211B2, 10% in MAJ
MAJ = Mint apple jelly, Crosse & Blackwell
Control = rearing diet of water, frozen flies, mealworms/honey agar

TABLE 8

Three week mortality (%) on pharaoh ant workers.

| Sample | Rate ppm | % Mortality |
| --- | --- | --- |
| 140E2 | 50000 | 100.0 |
| 86Q3 | 50000 | 99.6 |
| 211B2 | 50000 | 100.0 |
| MAJ | Blank | 75.3 |
| Control | Blank | 39.0 |

140E2 = 5% 140E2 purified protein in MAJ
86Q3 = 5% 86Q3 purified protein in MAJ
211B2 = 5% 211B2 purified protein in MAJ
MAJ = Mint apple jelly, Crosse & Blackwell
Control = rearing diet of water, frozen flies, mealworms/honey agar

EXAMPLE 9

Cloning of Novel Ant-Active Genes Using Generic Oligonucleotide Primers

The formicidal gene of a new formicidal B.t. can be obtained from DNA of the strain by performing the standard polymerase chain reaction procedure as in Example 6 using the oligonucleotides of SEQ ID NO. 33 or AGGAACAAAY-TCAAKWCGRTCTA (SEQ ID NO. 34) as reverse primers and SEQ ID NO. 12, SEQ ID NO. 13, SEQ ID NO. 15, SEQ ID NO. 16, SEQ ID NO. 23, SEQ ID NO. 27, SEQ ID NO. 29, or SEQ ID NO. 24 as forward primers. The expected PCR fragments would be approximately 330 to 600 bp with either reverse primer and SEQ ID NO. 12 or SEQ ID NO. 13, 1000 to 1400 bp with either reverse primer and SEQ ID NO. 15 or SEQ ID NO. 16, and 1800 to 2100 bp with either reverse primer and any of the three N-terminal primers, SEQ ID NO. 27, SEQ ID NO. 23, SEQ ID NO. 29, and SEQ ID NO. 24. Alternatively, a complement from the primer family described by SEQ ID NO. 12 and SEQ ID NO. 13 can be used as reverse primer with SEQ ID NO. 15, SEQ ID NO. 16, SEQ ID NO. 23, SEQ ID NO. 27, SEQ ID NO. 29, or SEQ ID NO. 24 as forward primers. The expected PCR fragments would be approximately 650 to 1000 bp with SEQ ID NO. 15 or SEQ ID NO. 16, and 1400 to 1800 bp for the four N-terminal primers (SEQ ID NO. 27, SEQ ID NO. 23, SEQ ID NO. 29, and SEQ ID NO. 24).

As another alternative, the reverse primer SEQ ID NO. 31 can be used with any of the four N-terminal forward primers to yield fragments of approximately 2550–3100 bp; 1750–2150 bp with the forward primers SEQ ID NOS. 15 or 16; 850–1400 bp with SEQ ID NOS. 12 or 13; and 550–1050 bp with the forward primer (TFTAGATCGT(A or C)TTGA(G or A)TTT(A or G)T(A or T)CC (SEQ ID NO. 35).

As yet another alternative, the ITSED (SEQ ID NO 36) reverse primer (TCTCCATCTTCFGA(G or A)G(T or A)AAT) (SEQ ID NO. 37) can be used with the N-terminal forward primers (SEQ ID NO. 23, SEQ ID NO. 24, SEQ ID NO. 27, and SEQ ID NO. 29) to yield fragments of approximately 3550–4050 bp; 2600–3100 bp with forward primers SEQ ID NOS. 15 or 16; 1800–2400 bp with forward primers SEQ ID NOS. 12 or 13; and 1500–2050 bp with forward primer SEQ ID NO. 35.

Amplified DNA fragments of the indicated sizes can be radiolabeled and used as probes to clone the entire gene as in Example 6.

EXAMPLE 10

Insertion of Toxin Gene Into Plants

One aspect of the subject invention is the transformation of plants with genes coding for a formicidal toxin. The transformed plants are resistant to attack by ants.

Genes coding for formicidal toxins, as disclosed herein, can be inserted into plant cells using a variety of techniques which are well known in the art. For example, a large number of cloning vectors comprising a replication system in E. coli and a marker that permits selection of the transformed cells are available for preparation for the insertion of foreign genes into higher plants. The vectors comprise, for example, pBR322, pUC series, M13mp series, pACYC184, etc. Accordingly, the sequence coding for the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobactedum rhizogenes* as transformation agent, fusion, injection, or electroporation as well as other possible methods. If agrobactefia are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or

*Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 11

Cloning of Novel *B. thuringiensis* Genes Into Insect Viruses

A number of viruses are known to infect insects. These viruses include, for example, baculoviruses and entomopoxviruses. In one embodiment of the subject invention, ant-active genes, as described herein, can be placed with the genome of the insect virus, thus enhancing the pathogenicity of the virus. Methods for constructing insect viruses which comprise B.t. toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A host transformed to express a nucleotide sequence encoding a toxin having activity against ant pests and having the amino acid sequence shown in SEQ ID NO. 8.

2. The host, according to claim 1, transformed to express the nucleotide sequence shown in SEQ ID NO. 7.

3. An isolated polynucleotide sequence comprising DNA encoding the amino acid sequence shown in SEQ ID NO. 8.

4. The polynucleotide, according to claim 3, wherein said DNA has the sequence shown in SEQ ID NO. 7.

* * * * *

UNITED STATES PATENT AND TRADEMARK OFFICE
CERTIFICATE OF CORRECTION

PATENT NO.   : 5,616,495
DATED        : April 1, 1997
INVENTOR(S)  : Payne, et al

It is certified that error appears in the above-identified patent and that said Letters Patent is hereby corrected as shown below:

Column 1, line 31: "*thutingiensis*" should read --*thuringiensis*--;

line 44: "*thutingiensis*" should read --*thuringiensis*--;

lines 58-59: "Formicidac" should read --Formicidae--.

Column 2, line 7: "*Monomodum*" should read --*Monomorium*--;

line 13: "*C. toodoe*" should read --*C. modoc*--.

Column 3, line 44: "*Monornoriurn*" should read --*Monomorium*--.

Column 4, line 4: "hornology" should read --homology--;

line 23: "arid" should read --and--.

Column 6, line 4: "*thudngiensis*" should read --*thuringiensis*--.

Column 7, #601, 2nd line, 3rd Col: "XZXXXXXXXx" should read --XZXXXXXXZx--

Column 8, line 7: "toms" should read --toxins--.

Column 9, line 14: "an" should read --art--.

UNITED STATES PATENT AND TRADEMARK OFFICE
CERTIFICATE OF CORRECTION

PATENT NO. : 5,616,495
DATED : April 1, 1997
INVENTOR(S) : Payne, et al

It is certified that error appears in the above-identified patent and that said Letters Patent is hereby corrected as shown below:

Column 10, line 3: "CryIIA;" should read --CryIIA;--;

line 4: "CryIA(c);" should read --CryIA(c);--;

line 22: "rrandom" should read --random--.

Column 11, line 29: "antactive" should read --ant-active-- line 38: "Bal13" should read --*Bal*31--;

line 52: "antactive" should read --ant-active--.

Column 12, line 62: "homology" should read --homology--;

line 63: "homology" should read --homology--;

line 66: "greater than and" should read --greater than 75%; and--.

Column 13, lines 12-13: "R or K;" should read --R or K;--;

line 25: "(C or T)TIT(T or G)" should read --(C or T)TTT(T or G)--;

line 35: "GCTFATG" should read --GCTTATG--.

Column 14, lines 2-3: "routants" should read --mutants--.

UNITED STATES PATENT AND TRADEMARK OFFICE
CERTIFICATE OF CORRECTION

PATENT NO. : 5,616,495
DATED : April 1, 1997
INVENTOR(S) : Payne, et al

It is certified that error appears in the above-identified patent and that said Letters Patent is hereby corrected as shown below:

Column 15, line 34: "fleezing," should read --freezing,--.

Column 16, line 3: "Streptornyces," should read --*Streptomyces*,--;

line 4: "Rhizobium, Rhodopseudornonas" should read --*Rhizobium, Rhodopseudomonas*--;

line 11: "*Agrobactedum*" should read --*Agrobacterium*--.

Column 17, line 59: "*J. Bactetiol.*" should read --*J. Bacteriol.*.--.

Column 20, line 14: "*Microbid. Lett.*" should read --Microbiol. Lett.--.

Column 21, line 11: "GAATYATATCC" should read --GAATTATATCC--;

line 41: "Sa/I" should read --*SaI*I--.

Column 22, line 28: "CAA T/CTA CAAGCAfF" should read --CAA T/CTA CAA GCA/T--.

Column 22, line 43: "*cells grown to an optical density of*" should read --cells grown to an optical density of-- line 63: (PROMECA)." should read --(PROMEGA).--;

UNITED STATES PATENT AND TRADEMARK OFFICE
CERTIFICATE OF CORRECTION

PATENT NO. : 5,616,495
DATED : April 1, 1997
INVENTOR(S) : Payne, et al

It is certified that error appears in the above-identified patent and that said Letters Patent is hereby corrected as shown below:

Column 22, line 64: "KW25 1" should read --KW251--;

line 65: "(PROMECA)" should read --(PROMEGA)--.

Column 23, line 4: "KW25 1" should read --KW251--;

line 17: "*Microbiol. Lea.*" should read --*Microbiol. Lett.*--;

line 46: "fleezing" should read --freezing--.

Column 24, lines 6-7: "5' GCAfF ACA/T TTA AAT GAA GTAE TAT 3' (SEQ ID NO. 26)" should read --5' GCA/T ACA/TTTA AAT GAAGTA/TTAT 3' (SEQ ID NO. 26)--.

line 8: "5' AAT GAA GTAfF" should read --5' AAT GAA GTA/T--;

line 15: "5' GCAAGCGGCCGCTTATGGAAAAATTCAATT C/T" should read --5' GCAAGCGGCCGCTTATGGAATAAATTCAATT C/T--.

Column 25, lines 17-18: "(C or G) TITTAATTT(T or A)" should read --(C or G) TTTTAATTT(T or A)--;

line 22: "5'-TGGAATAAATTCAATF(C or T)" should read --5'-TGGAATAAATTCAATT(C or T)--;

UNITED STATES PATENT AND TRADEMARK OFFICE
CERTIFICATE OF CORRECTION

PATENT NO. : 5,616,495
DATED : April 1, 1997
INVENTOR(S) : Payne, et al

It is certified that error appears in the above-identified patent and that said Letters Patent is hereby corrected as shown below:

Column 25, line 45: "KW25 1" should read --KW251--;

line 51: "Zprocedures" should read --procedures--.

Column 26, line 16: "2Broths were" should read --Broths were--;

line 20: "*thutingiensis*" should read --*thuringiensis*--.

Column 27, line 47: "(TFTAGATCGT(A or" should read --(TTTAGATCGT(A or--;

line 51: "(TCTCCATCTTCFGA(G or" should read --(TCTCCATCTTCTGA(G or--.

Column 28, line 44: "*Agrobactedum*" should read --*Agrobacterium*--;

line 46: "agrobactefia" should read --agrobacteria--.

Signed and Sealed this

Sixteenth Day of June, 1998

BRUCE LEHMAN

*Attest:*

*Attesting Officer*     *Commissioner of Patents and Trademarks*